US011253516B2

(12) United States Patent
Lee et al.

(10) Patent No.: US 11,253,516 B2
(45) Date of Patent: Feb. 22, 2022

(54) N2,N4-DIPHENYLPYRIMIDINE-2,4-DIAMINE DERIVATIVE, METHOD FOR PREPARING SAME, AND PHARMACEUTICAL COMPOSITION CONTAINING SAME AS ACTIVE INGREDIENT FOR PREVENTION OR TREATMENT OF CANCER

(71) Applicant: Korea Research Institute of Chemical Technology, Daejeon (KR)

(72) Inventors: Kwangho Lee, Daejeon (KR); Inji Shin, Daejeon (KR); Gildon Choi, Daejeon (KR); Chong Hak Chae, Daejeon (KR); Hyeon Jeong Choe, Daejeon (KR); Myoung Eun Jung, Daejeon (KR); Byeong Uk Jeon, Boryeong-Si (KR); Byoung Chul Cho, Seoul (KR); Chae Won Park, Seoul (KR); Hwan Kim, Seoul (KR); Krishna Babu Duggirala, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 6 days.

(21) Appl. No.: 16/622,057

(22) PCT Filed: Jun. 12, 2018

(86) PCT No.: PCT/KR2018/006644
§ 371 (c)(1),
(2) Date: Dec. 12, 2019

(87) PCT Pub. No.: WO2018/230934
PCT Pub. Date: Dec. 20, 2018

(65) Prior Publication Data
US 2020/0179384 A1  Jun. 11, 2020

(30) Foreign Application Priority Data

Jun. 13, 2017 (KR) .................. 10-2017-0073907
Nov. 3, 2017 (KR) .................. 10-2017-0146241

(51) Int. Cl.
*A61K 31/506* (2006.01)
*A61K 31/5377* (2006.01)
*A61K 45/06* (2006.01)
*A61P 35/00* (2006.01)
*C07D 413/12* (2006.01)
*C07D 401/14* (2006.01)
*C07D 413/14* (2006.01)
*C07D 401/12* (2006.01)

(52) U.S. Cl.
CPC ........ *A61K 31/506* (2013.01); *A61K 31/5377* (2013.01); *A61K 45/06* (2013.01); *A61P 35/00* (2018.01); *C07D 401/12* (2013.01); *C07D 401/14* (2013.01); *C07D 413/12* (2013.01); *C07D 413/14* (2013.01)

(58) Field of Classification Search
CPC .. A61K 31/506; A61K 31/5377; A61K 45/06; A61K 35/00; C07D 413/12; C07D 401/14; C07D 413/14; C07D 401/12
See application file for complete search history.

(56) References Cited

U.S. PATENT DOCUMENTS

| 7,893,074 B2 * | 2/2011 | Garcia-Echeverria ...................... A61P 31/18 514/275 |
| 9,012,462 B2 | 4/2015 | Wang et al. |
| 2008/0176881 A1 | 7/2008 | Michellys et al. |
| 2011/0098280 A1 | 4/2011 | Garcia-Echeverria et al. |

FOREIGN PATENT DOCUMENTS

| KR | 20150102252 A | 9/2015 |
| KR | 2015/0145176 A | 12/2015 |
| KR | 20170015848 A | 2/2017 |
| KR | 20170027757 A | 3/2017 |
| WO | WO-2009127642 A2 | 10/2009 |
| WO | WO-2015130014 A1 | 9/2015 |
| WO | WO-2015/176010 A1 | 11/2015 |
| WO | WO-2016027904 A1 | 2/2016 |

OTHER PUBLICATIONS

Choe et al., "Structure-Activity Relationship Study of 2,4-Dianilinpoyrimidine Containing Methanesulfonamide (TRE-069) as Potent and Selective Epidermal Growth Factor Receptor T790M/C797S Mutant Inhibitor for Anticancer Treatment," Bulletin Kor Chem Soc 38:1353-1357 (2017).
Galatsis et al., "Chapter Four—Development of LRRK2 Kinase Inhibitors for Parkinson's Disease," Ann Reps Med Chem 49:43-58 (2014).
Galkin et al., "Identification of NVP-TAE684, a potent, selective, and efficacious inhibitor of NPM-ALK," PNAS, 104(1):270-275 (2007).
International Search Report and Written Opinion for International Application No. PCT/KR2018/006644 dated Sep. 10, 2018.

(Continued)

*Primary Examiner* — Tracy Vivlemore
*Assistant Examiner* — Ebenezer O Sackey
(74) *Attorney, Agent, or Firm* — Foley Hoag LLP; David P. Halstead

(57) ABSTRACT

The present invention relates to a N2,N4-diphenylpyrimidin-2,4-diamine derivative, a method for preparing the same, and a pharmaceutical composition for the prevention or treatment of cancer, containing the same as an active ingredient. The derivative shows a relatively weak EGFR activity inhibitory effect on wild-type EGFR, a high inhibitory ability on EGFR mutation, and a high inhibitory ability on even FLT3 and FLT3 mutation, and thus, can be effectively used for the treatment of cancer with EGFR mutation or cancer with FLT3 or a mutation thereof, and the derivative shows a synergy effect at the time of combination administration, and thus can be effectively used for the treatment of combination administration.

20 Claims, 7 Drawing Sheets

(56) References Cited

OTHER PUBLICATIONS

Kavanagh et al., "The development of CNS-active LRRK2 inhibitors using property-directed optimisation," Bioorganic & Medicinal Chemistry Letters, 23:3690-3696 (2013).
Marsilje et al., "Synthesis, Structure-Activity Relationships and In Vivo Efficacy of the Novel Potent and Selective Anaplastic Lymphoma Kinase (ALK) Inhibitor LDK378 Currently in Phase 1 and 2 Clinical Trials," Journal of Medicinal Chemistry, 1-58 (2013).
Mori et al., "The Selective Anaplastic Lymphoma Receptor Tyrosine Kinase Inhibitor ASP3026 Induces Tumor Regression and Prolongs Survival in Non-Small Cell Lung Cancer Model Mice," Mol Cancer Ther, 13(2):329-340 (2014).
Ramsden et al., "Chemoproteomics-Based Design of Potent LRRK2-Selective Lead Compounds That Attenuate Parkinson's Disease-Related Toxicity in Human Neurons," ACS Chemical Biology, 6:1021-1028 (2011).
Zhang et al., "Characterization of TAE684 as a potent LRRK2 kinase inhibitor," Bioorganic & Medicinal Chemistry Letters, 22:1864-1869 (2012).
Zhou et al., "Discovery of selective 2,4-diaminopyrimidine-based photoaffinity probes for glyoxalase I," MedChemComm, 5:352-357 (2014).

\* cited by examiner

N2,N4-DIPHENYLPYRIMIDINE-2,4-DIAMINE DERIVATIVE, METHOD FOR PREPARING SAME, AND PHARMACEUTICAL COMPOSITION CONTAINING SAME AS ACTIVE INGREDIENT FOR PREVENTION OR TREATMENT OF CANCER

RELATED APPLICATIONS

This application is a U.S. National Stage Application of International Application No. PCT/KR2018/006644 filed Jun. 12, 2018, which claims the benefit of priority to Korean Application No. 10-2017-0146241 filed Nov. 3, 2017 and Korean Application No. 10-2017-0073907 filed Jun. 13, 2017. The contents of PCT/KR2018/006644 are hereby incorporated by reference in their entireties.

TECHNICAL FIELD

The present invention relates to a N2,N4-diphenylpyrimidin-2,4-diamine derivative, a method for preparing the same, and a pharmaceutical composition for the prevention or treatment of cancer, containing the same as an active ingredient.

BACKGROUND ART

The occurrence of cancers is related to a number of environmental factors including chemical substances, radiation, virus, and changes of oncogenes, tumor suppressor genes, genes associated with apoptosis and DNA repair and the like. Recently, the molecular mechanism of cancers is to be understood, and thus, this makes a targeted anticancer therapy, which is a new therapy, become available.

Targeted therapeutic agents are generally prepared to show an effect by targeting molecules that cancer cells characteristically have. The molecular targets are genes associated with signal transduction pathway of cancer cells, angiogenesis, cellular matrix, cell cycle regulator, apoptosis and the like. An important targeted therapeutic agent used in the current therapy includes signal transduction pathway inhibitors, including tyrosine kinase inhibitors, and angiogenesis inhibitors and the like.

It has been found that a protein tyrosine kinase plays an important role in a number of malignant tumors. In particular, it is known that epidermal growth factor receptor (EGFR), which is a receptor tyrosine kinase of ErbB family, is abnormally activated in a number of epithelial cell tumors including non-small cell lung carcinoma (NSCLC), breast cancer, glioma, squamous cell carcinoma of head and neck, colorectal cancer, rectal adenocarcinoma, head and neck cancer, gastric cancer, and prostate cancer; and the activation of the above EGFR-tyrosine kinase causes a persistent cell proliferation, invasion of the surrounding tissue, remote metastasis, and angiogenesis, and increases a cell survival.

Specifically, the EGFR, which is one of tyrosine kinase receptors of ErbB family (EGFR, HER-2, ErbB-3, and ErbB-4), is a transmembrane tyrosine kinase that has an extracellular ligand-binding domain and an intracellular domain including a tyrosine kinase domain. If a ligand binds to a receptor forming homodimer or heterodimer, a tyrosine kinase in a cell is activated, and a signal stimulated by EGFR as such activates phosphatidylinositol 3-kinase (PI3K)/AKT/mTOR, RAS/RAF/MAPK, and JAK/STAT signal transduction pathway (Nat Rev Cancer 2007; 7:169-81).

In particular, EGFR is overexpressed in at least a half of non-small cell lung cancer (NSCLC), and thus, a number of studies have been carried out in which EGFR is a target of a therapy. EGFR TKIs (tyrosine kinase inhibitors), which inhibit an activity of EGFR tyrosine kinase, have been developed, and representative drugs include Gefitinib (IRESSA™) erlotinib (TARCEVA™), lapatinib (TYKERB™, TYVERB™).

On the other hand, it was reported that, in 2004, an activating mutation of EGFR is correlated with a response to gefitinib therapy in non-small cell lung cancer (NSCLC) (Science [2004] Vol. 304, 1497-500 and New England Journal of Medicine [2004] Vol. 350, 2129-39).

Specifically, it is known that the above EGFR mutation is largely classified into a sensitizing mutation and a resistant mutation, and a deletion of exon 19 and a L858R point mutation of exon 21 are the most important sensitizing mutations and make up about 85 to 90 percent of a sensitizing mutation, and an exon 19 del mutation is more sensitizing to the TKI. On the other hand, it is known that a T790M point mutation of exon 20 is the most important resistant mutation and is found in at least 50 percent of acquired resistant patients (Clin Cancer Res 2006; 12:6494-6501).

Somatic mutations identified hitherto include an in-frame deletion in exon 19 or an insertion in exon 20, as well as, a point mutation in which a single nucleic acid residue is modified within an expressed protein (for example, L858R, G719S, G719C, G719A, L861Q) (Fukuoka et al. JCO 2003; Kris et al JAMA 2003; and Shepherd et al NEJM 2004).

Despite an early clinical effect of gefitinib/erlotinib in NSCLC patients with a EGFR mutation, a progressive cancer develops in most patients in the end while these patients are receiving a therapy of these drugs. In an early study of recurred samples, a secondary EGFR mutation, T790M, was identified, which made gefitinib and erlotinib to be ineffective inhibitors of EGFR kinase activity (Kobayashi et al NEJM 2005 and Pao et al PLOS Medicine 2005). It has been proved in the follow-up study that the EGFR T790M mutation was found in approximately 50 percent ($^{24}/_{48}$) of tumors derived from patients who acquired a resistance against gefitinib or erlotinib (Kosaka et al CCR 2006; Balak et al CCR 2006; and Engelman et al Science 2007). The secondary genetic modification is caused in a position similar to a 'gatekeeper' residue and a secondary resistance allele associated with the same in patients to be treated with a kinase inhibitor (for example, T3151 within ABL in imatinib resistant CML).

It has been known for a long time that EGFR_del19 or EGFR_L858R, which is an EGFR mutation, is a major cause of non-small cell lung cancer and head and neck cancer, and IRESSA and TARCEVA, which are therapeutic drugs of the cancers, were developed and are currently used in clinical trials. However, when such drugs were administered for cancer patients, an acquired resistance caused by an EGFR secondary mutation based on the structure of the drug was observed. In addition, it was found that this was actually a major cause of drug resistance. If first generation inhibitors of EGFR have been used for about ten months in average, an acquired resistance, which is a T790M mutation positioned in a gatekeeper of EGFR kinase, occurs to prevent first generation inhibitors of EGFR exerting a medicinal effect. That is, EGFR_del19_T790M or EGFR_L858R_T790M double mutation occurs to prevent conventional therapeutic agents exerting a medicinal effect.

On the basis of these facts, it is imperative to develop the second generation and third generation drugs having a superior medicinal effect and a new structure.

For the last five years, various third generation new drug candidates showing an effect on an EGFR T790M double mutation are under development, and clinical studies are in progress. AZD9291 developed by AstraZeneca, a multinational pharmaceutical company, is the most promising drug. However, it was reported that after approximately ten months passed, another resistance against AZD9291 also occurred to lose the medicinal effect of AZD9291. In particular, it was reported that resistance caused by triple mutation including C797S occurred (Thress et al, Nature Medicine 2015).

Thus, there is a need for the development of an inhibitor showing a higher inhibition on EGFR of specific activating or resistant mutant form while showing a relatively low inhibition on WT EGFR.

Thus, while the prevent inventors were trying to develop a cancer therapeutic agent inhibiting an EGFR multiple mutation, the prevent inventors found that a N2,N4-diphenylpyrimidin-2,4-diamine derivative according to the present invention shows a relatively low inhibition on wild-type EGFR and a high inhibitory ability on EGFR mutation, and thus, can be effectively used for the prevention or treatment of cancer. On the basis of the above findings, the present invention has been completed.

DETAILED DESCRIPTION OF THE INVENTION

Technical Problem

It is an object of the present invention to provide a N2,N4-diphenylpyrimidin-2,4-diamine derivative, an optical isomer thereof or a pharmaceutically acceptable salt thereof.

It is another object of the present invention to provide a method for preparing the N2,N4-diphenylpyrimidin-2,4-diamine derivative.

It is another object of the present invention to provide a pharmaceutical composition for the prevention or treatment of cancer, containing the N2,N4-diphenylpyrimidin-2,4-diamine derivative, an optical isomer thereof, or a pharmaceutically acceptable salt thereof as an active ingredient.

It is another object of the present invention to provide a health functional food composition for the prevention or amelioration of cancer, containing the N2,N4-diphenylpyrimidin-2,4-diamine derivative, an optical isomer thereof, or a pharmaceutically acceptable salt thereof as an active ingredient.

Solution to Problem

In order to accomplish the above objects, the present invention provides a compound represented by Formula 1:

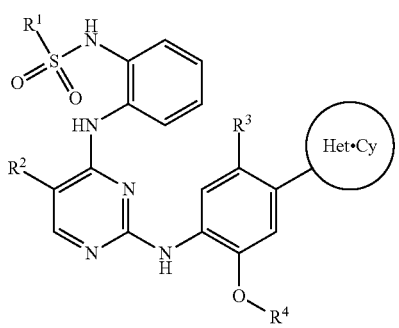

(1)

in which, $R^1$ is $CH_3$ or $NH_2$, $R^2$ is hydrogen, halogen, methoxy, or methyl unsubstituted or substituted with one or more halogens;

$R^3$ is hydrogen, halogen, or straight or branched $C_{1-6}$alkyl;

$R^4$ is straight or branched $C_{1-6}$alkyl; and

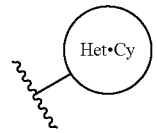

is an unsubstituted or substituted 5- to 7-membered heterocycloalkyl comprising one or more heteroatoms selected from the group consisting of N, O, and S, wherein the substituted heterocycloalkyl may be substituted with one or more substituents selected from the group consisting of straight or branched $C_{1-3}$ alkyl, straight or branched hydroxy$C_{1-3}$alkyl, acetyl, amine unsubstituted or substituted with one or more straight or branched $C_{1-3}$alkyl, and unsubstituted or substituted piperidinyl or piperazinyl, and the substituted piperidinyl or piperazinyl may be substituted with one or more substituents selected from the group consisting of straight or branched $C_{1-3}$alkyl, straight or branched hydroxy$C_{1-3}$alkyl, acetyl, and straight or branched $C_{1-5}$alkoxycarbonyl, an optical isomer thereof or a pharmaceutically acceptable salt thereof.

In addition, the present invention provides a method for preparing the compound represented by Formula 1, comprising a step of reacting a compound represented by Formula 2 and a compound represented by Formula 3 to prepare the compound represented by Formula 1, as indicated in Reaction Scheme 1:

[Reaction Scheme 1]

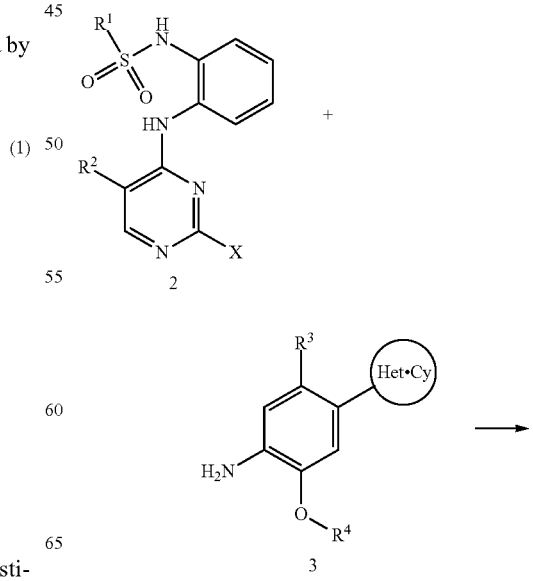

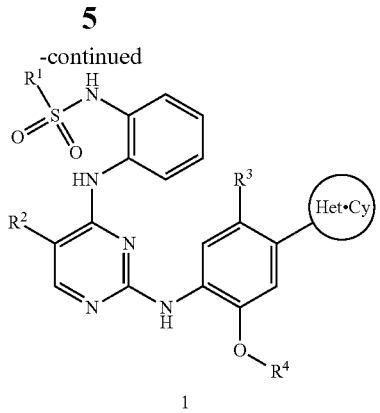

in which, $R^1$, $R^2$, $R^3$, $R^4$, and

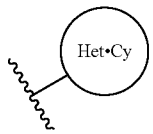

are as defined in Formula 1 above; and

X is halogen.

Furthermore, the present invention provides a pharmaceutical composition for the prevention or treatment of cancer, containing the compound represented by Formula 1, optical isomer thereof, or pharmaceutically acceptable salt thereof as an active ingredient.

In addition, the present invention provides a health functional food for the prevention or amelioration of cancer, containing the compound represented by Formula 1, optical isomer thereof, or pharmaceutically acceptable salt thereof as an active ingredient.

In addition, the present invention provides a method for the prevention or treatment of cancer, comprising a step of administering a pharmaceutical composition or a health functional food composition containing the compound represented by Formula 1 or pharmaceutically acceptable salt thereof as an active ingredient to a subject in need thereof.

In addition, the present invention provides a use of a pharmaceutical composition or a health functional food composition containing the compound represented by Formula 1 or pharmaceutically acceptable salt thereof in the prevention or treatment of cancer.

Effect of Invention

The N2,N4-diphenylpyrimidin-2,4-diamine derivative according to the present invention shows a relatively weak EGFR activity inhibitory effect on wild-type EGFR, a high inhibitory ability on EGFR mutation, and a high inhibitory ability on even fms-like tyrosine kinase 3 (FLT3) and FLT3 mutation, and thus, can be effectively used for the treatment of cancer with EGFR mutation or cancer with FLT3 or a mutation thereof, and the derivative shows a synergy effect at the time of combination administration, and thus, can be effectively used for the treatment of combination administration.

BEST EMBODIMENT FOR WORKING THE INVENTION

Figure 1:
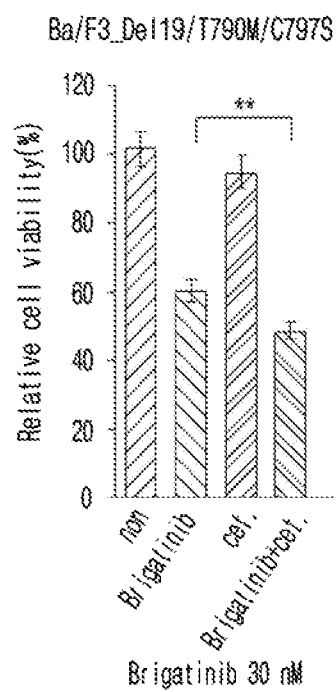
FIG. 1 is a graph showing a relative cell viability at the time of the administration of brigatinib in combination with cetuximab to Ba/F3 Del19/T790M/C797S cell line (calculated by sigmaplot's t-test (**P<0.001, *P>0.01)).

Hereinafter, the present invention will be described in detail.

The present invention provides a compound represented by Formula 1:

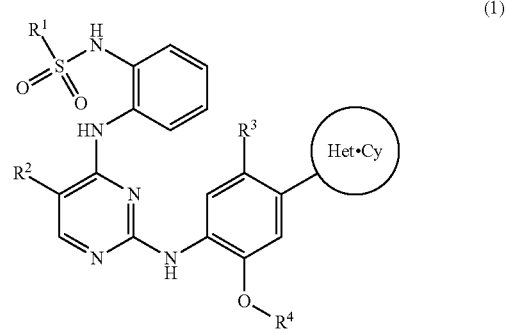

in which, $R^1$ is $CH_3$ or $NH_2$, $R^2$ is hydrogen, halogen, methoxy, or methyl unsubstituted or substituted with one or more halogens;

$R^3$ is hydrogen, halogen, or straight or branched $C_{1-6}$alkyl;

$R^4$ is straight or branched $C_{1-6}$alkyl; and

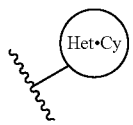

is an unsubstituted or substituted 5- to 7-membered heterocycloalkyl comprising one or more heteroatoms selected from the group consisting of N, O, and S, wherein the substituted heterocycloalkyl may be substituted with one or more substituents selected from the group consisting of straight or branched $C_{1-3}$alkyl, straight or branched hydroxy$C_{1-3}$alkyl, acetyl, amine unsubstituted or substituted with one or more straight or branched $C_{1-3}$alkyl, and unsubstituted or substituted piperidinyl or piperazinyl, and the substituted piperidinyl or piperazinyl may be substituted with one or more substituents selected from the group consisting of straight or branched $C_{1-3}$alkyl, straight or branched hydroxy$C_{1-3}$alkyl, acetyl, and straight or branched $C_{1-5}$alkoxycarbonyl, an optical isomer thereof or a pharmaceutically acceptable salt thereof.

$R^1$ may be $CH_3$.

$R^1$ may be $NH_2$.

$R^2$ may be hydrogen, F, Cl, Br, methoxy, or methyl unsubstituted or substituted with one or more fluoro;

$R^3$ may be hydrogen, F, Cl, or straight or branched $C_{1-3}$alkyl; and $R^4$ may be straight or branched $C_{1-3}$alkyl.

$R^2$ may be hydrogen, Cl, Br, methyl, $CF_3$, or methoxy;

$R^3$ may be hydrogen or methyl; and $R^4$ may be methyl.

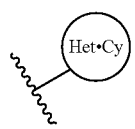

is unsubstituted or substituted 5- or 6-membered heterocycloalkyl comprising one or more heteroatoms selected from the group consisting of N, O, and S, wherein the substituted heterocycloalkyl may be substituted with one or more substituents selected from the group consisting of methyl, ethyl, hydroxymethyl, hydroxyethyl, acetyl, amine unsubstituted or substituted with one or more methyl, and unsubstituted or substituted piperidinyl or piperazinyl, and the substituted piperidinyl or piperazinyl may be substituted with one or more substituents selected from the group consisting of methyl, ethyl, hydroxymethyl, hydroxyethyl, acetyl, and tert-butoxy carbonyl.

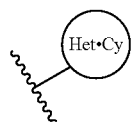

is unsubstituted or substituted 5- or 6-membered heterocycloalkyl comprising one or more heteroatoms selected from the group consisting of N and O, wherein the substituted heterocycloalkyl may be substituted with one or more substituents selected from the group consisting of methyl, hydroxyethyl, acetyl, $-NH_2$, $-N(CH_3)_2$, and unsubstituted or substituted piperidinyl or piperazinyl, and the substituted piperidinyl or piperazinyl may be substituted with one or more substituents selected from the group consisting of methyl, hydroxyethyl, acetyl, and tert-butoxycarbonyl.

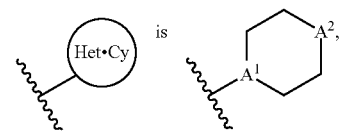

wherein $A^1$ is CH or N, and $A^2$ is NH, O, CH—$R^5$, or N—$R^5$, with the proviso that if A1 is CH, then $A^2$ is not CH—$R^5$, wherein $R^5$ is independently hydrogen, methyl, hydroxyethyl, acetyl, $-NH_2$, $-N(CH_3)_2$,

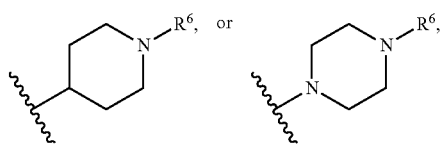

and $R^6$ may be independently hydrogen, methyl, hydroxyethyl, acetyl or tert-butoxycarbonyl.

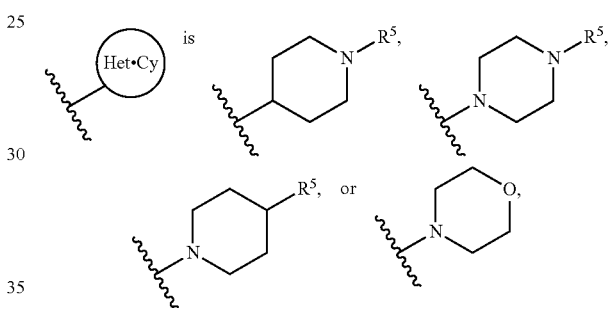

wherein $R^5$ is independently hydrogen, methyl, hydroxyethyl, acetyl, $-NH_2$, $-N(CH_3)_2$,

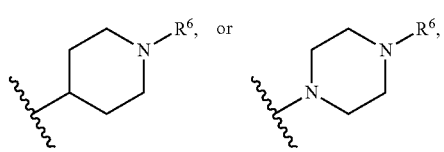

and $R^6$ may be independently hydrogen, methyl, hydroxyethyl, acetyl, or tert-butoxycarbonyl.

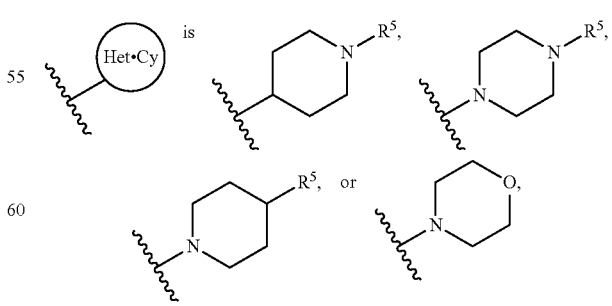

wherein $R^5$ may be hydrogen, methyl, hydroxyethyl, acetyl, $-NH_2$, $-N(CH_3)_2$,

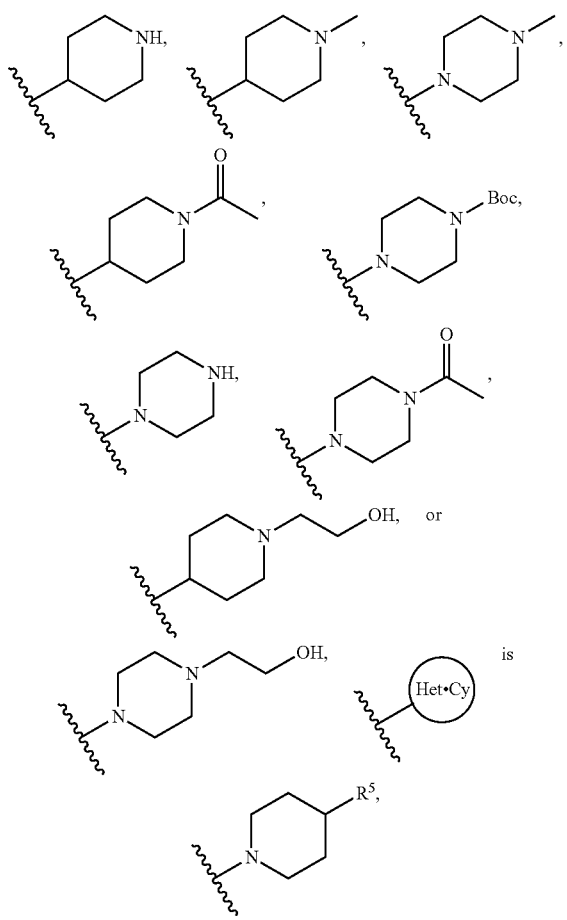

wherein $R^5$ is independently —NH(CH$_3$) or

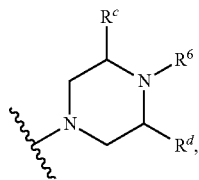

wherein $R^c$ and $R^d$ is independently hydrogen, and $R^6$ may be methyl.

Examples of the compound represented by Formula 1 according to the present invention include the following compounds:

<1> N-(2-((5-chloro-2-((2-methoxy-4-(piperidin-4-yl)phenyl)amino)pyrimidin-4-yl)amino)phenyl) methanesulfonamide;
<2> N-(2-((5-chloro-2-((2-methoxy-5-methyl-4-(piperidin-4-yl)phenyl)amino)pyrimidin-4-yl)amino)phenyl)methanesulfonamide;
<3> N-(2-((5-bromo-2-((2-methoxy-4-(piperidin-4-yl)phenyl)amino)pyrimidin-4-yl)amino)phenyl) methanesulfonamide;
<4> N-(2-((5-methoxy-2-((2-methoxy-4-(piperidin-4-yl)phenyl)amino)pyrimidin-4-yl)amino)phenyl)methanesulfonamide;
<5> N-(2-((2-((2-methoxy-4-(piperazin-1-yl)phenyl)amino)-5-(trifluoromethyl)pyrimidin-4-yl)amino)phenyl)methmethanesulfonamide;
<6> 4-(4-((5-chloro-4-((2-(sulfamoylamino)phenyl)amino)pyrimidin-2-yl)amino)-3-methoxyphenyl)piperidine;
<7> 4-(4-((5-bromo-4-((2-(sulfamoylamino)phenyl)amino)pyrimidin-2-yl)amino)-3-methoxyphenyl)piperidine;
<8> N-(2-((2-((2-methoxy-4-(piperidin-4-yl)phenyl)amino))-5-methylpyrimidin-4-ylamino)phenyl)methanesulfonamide;
<9> N-(2-((2-((2-methoxy-4-(piperidin-4-yl)phenyl)amino)pyrimidin-4-yl)amino)phenyl)methane sulfonamide;
<10> N-(2-((5-chloro-2-((2-methoxy-4-(4-(4-methylpiperazin-1-yl)piperidin-1-yl)phenyl)amino)pyrimidin-4-yl)amino)phenyl)methanesulfonamide;
<11> N-(2-((5-chloro-2-((4-(4-(dimethylamino)piperidin-1-yl)-2-methoxyphenyl)amino)pyrimidin-4-yl)amino)phenyl)methanesulfonamide;
<12> N-(2-((5-chloro-2-((2-methoxy-4-(1-methylpiperidin-4-yl)phenyl)amino)pyrimidin-4-yl)amino)phenyl)methanesulfonamide;
<13> N-(2-((5-chloro-2-((4-(1-(2-hydroxyethyl)piperidin-4-yl)-2-methoxyphenyl)amino)pyrimidin-4-yl)amino)phenyl)methanesulfonamide;
<14> N-(2-((5-chloro-2-((4-(1'-(2-hydroxyethyl)-[1,4'-bipiperidin]-4-yl)-2-methoxyphenyl)amino)pyrimidin-4-yl)amino)phenyl)methanesulfonamide;
<15> N-(2-((2-((4-(1-acetylpiperidin-4-yl)-2-methoxyphenyl)amino)-5-chloropyrimidin-4-yl)amino)phenyl)methanesulfonamide;
<16> N-(2-((2-((4-([1,4'-bipiperidin]-4-yl)-2-methoxyphenyl)amino)-5-chloropyrimidin-4-yl)amino)phenyl)methanesulfonamide;
<17> N-(2-((5-chloro-2-((2-methoxy-4-(1'-methyl-[1,4'-bipiperidin]-4-yl)phenyl)amino)pyrimidin-4-yl)amino)phenyl)methanesulfonamide;
<18> N-(2-((2-((4-(1'-acetyl-[1,4'-bipiperidin]-4-yl)-2-methoxyphenyl)amino)-5-chloropyrimidin-4-yl)amino)phenyl)methanesulfonamide;
<19> N-(2-((2-((4-(4-(4-acetylpiperazin-1-yl)piperidin-1-yl)-2-methoxyphenyl)amino)-5-chloropyrimidin-4-yl)amino)phenyl)methanesulfonamide;
<20> tert-butyl 4-(1-(4-((5-chloro-4-((2-(methylsulfonamido)phenyl)amino)pyrimidin-2-yl)amino)-3-methoxyphenyl)piperidin-4-yl)piperazine-1-carboxylate;
<21> N-(2-((5-chloro-2-((2-methoxy-4-(4-(piperazin-1-yl)piperidin-1-yl)phenyl)amino)pyrimidin-4-yl)amino)phenyl)methanesulfonamide;
<22> N-(2-((5-chloro-2-((4-(4-(4-(2-hydroxyethyl)piperazin-1-yl)piperidin-1-yl)-2-methoxyphenyl) amino)pyrimidin-4-yl)amino)phenyl)methanesulfonamide;
<23> N-(2-((5-chloro-2-((2-methoxy-4-(piperazin-1-yl)phenyl)amino)pyrimidin-4-yl)amino)phenyl) methanesulfonamide;
<24> N-(2-((2-((4-(4-(1-acetylpiperidin-4-yl)piperazin-1-yl)-2-methoxyphenyl)amino)-5-chloropyrimidin-4-yl)amino)phenyl)methanesulfonamide;
<25> N-(2-((5-chloro-2-((2-methoxy-4-(4-(1-methylpiperidin-4-yl)piperazin-1-yl)phenyl)amino)pyrimidin-4-yl)amino)phenyl)methanesulfonamide;
<26> tert-butyl 4-(4-(4-((5-chloro-4-((2-(methylsulfonamido)phenyl)amino)pyrimidin-2-yl)amino)-3-methoxyphenyl)piperazin-1-yl)piperidine-1-carboxylate;
<27> N-(2-((5-chloro-2-((2-methoxy-4-(4-(piperidin-4-yl)piperazin-1-yl)phenyl)amino)pyrimidin-4-yl)amino)phenyl)methanesulfonamide;
<28> N-(2-((5-chloro-2-((2-methoxy-4-(4-methylpiperazin-1-yl)phenyl)amino)pyrimidin-4-yl)amino)phenyl)methanesulfonamide;

<29> 4-(4-((5-chloro-4-((2-(sulfamoylamino)phenyl)amino)pyrimidin-2-yl)amino)-3-methoxyphenyl)piperazine;
<30> 4-(4-((5-bromo-4-((2-(sulfamoylamino)phenyl)amino)pyrimidin-2-yl)amino)-3-methoxyphenyl)piperazine;
<31> N-(2-((2-((2-methoxy-4-(piperazin-4-yl)phenyl)amino)-5-(trifluoromethyl)pyrimidin-4-yl)amino)phenyl)methanesulfonamide;
<32> N-(2-((5-chloro-2-((2-methoxy-4-morpholinophenyl)amino)pyrimidin-4-yl)amino)phenyl)methanesulfonamide;
<33> N-(2-((5-chloro-2-((4-(4-((3R,5S)-3,5-dimethylpiperazin-1-yl)piperidin-1-yl)-2-methoxy phenyl)amino)pyrimidin-4-yl)amino)phenyl)methanesulfonamide;
<34> N-(2-((5-chloro-2-((2-methoxy-4-(4-morpholinopiperidin-1-yl)phenyl)amino)pyrimidin-4-yl) amino)phenyl)methanesulfonamide;
<35> N-(2-((5-chloro-2-((2-methoxy-4-(4-(pyrrolidin-1-yl)piperidin-1-yl)phenyl)amino)pyrimidin-4-yl)amino)phenyl)methanesulfonamide;
<36> (N-(2-((5-chloro-2-((4-(4-(dimethylamino)piperidin-1-yl)-2-methoxy phenyl)amino)pyrimidin-4-yl)amino)phenyl)sulfamoyl)carbamate;
<37> (N-(2-((5-chloro-2-((2-methoxy-4-(4-(4-methylpiperazin-1-yl)piperidin-1-yl)phenyl)amino)pyrimidin-4-yl)amino)phenyl)sulfamoyl)carbamate;
<38> N-(2-((2-((4-(4-aminopiperidin-1-yl)-2-methoxyphenyl)amino)-5-chloropyrimidin-4-yl)amino)phenyl)methanesulfonamide;
<39> N-(1-(4-((5-chloro-4-((2-(methylsulfonamido)phenyl)amino)pyrimidin-2-yl)amino)-3-methoxyphenyl)piperidin-4-yl)acetamide;
<40> N-(2-((5-chloro-2-((2-methoxy-4-(4-(methylamino)piperidin-1-yl)phenyl)amino)pyrimidin-4-yl)amino)phenyl)methanesulfonamide;
<41> N-(2-((5-chloro-2-((4-(4-((2-hydroxy ethyl)amino)piperidin-1-yl)-2-methoxyphenyl)amino)pyrimidin-4-yl)amino)phenyl)methanesulfonamide;
<42> N-(2-((5-chloro-2-((2-methoxy-4-((2-methoxy ethyl)amino)piperidin-1-yl)phenyl)amino)pyrimidin-4-yl)amino)phenyl)methanesulfonamide; and
<43> N-(2-((5-chloro-2-((4-(4-((2-(dimethylamino)ethyl)amino)piperidin-1-yl)-2-methoxyphenyl)amino)pyrimidin-4-yl)amino)phenyl)methanesulfonamide.

The compound represented by Formula 1 of the present invention may be used in form of a pharmaceutically acceptable salt, and an acid addition salt formed by a pharmaceutically acceptable free acid is useful as a salt. The acid addition salt is obtained from inorganic acids, such as hydrochloric acid, nitric acid, phosphoric acid, sulfuric acid, hydrobromic acid, hydroiodic acid, nitrous acid, phosphorous acid and the like, nontoxic organic acids, such as aliphatic mono- and dicarboxylate, phenyl-substituted alkanoate, hydroxy alkanoate and alkandioate, aromatic acids, aliphatic and aromatic sulfonic acids and the like, organic acids, such as acetate, benzoic acid, citric acid, lactic acid, maleic acid, gluconic acid, methanesulfonic acid, 4-toluenesulfonic acid, tartaric acid, fumaric acid and the like. Types of such pharmaceutically nontoxic salts include sulfate, pyrosulfate, bisulfate, sulfite, bisulfite, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzene sulfonate, toluene sulfonate, chlorobenzene sulfonate, xylene sulfonate, phenylacetate, phenylpropionate, phenylbutyrate, citrate, lactate, β-hydroxybutyrate, glycolate, malate, tartrate, methane sulfonate, propane sulfonate, naphthalene-1-sulfonate, naphthalene-2-sulfonate, mandelate and the like.

The acid addition salt according to the present invention may be prepared by a conventional method, and, for example, it may be prepared by dissolving the derivative of Formula 1 in an organic solvent, such as methanol, ethanol, acetone, methylene chloride, acetonitrile and the like, adding an organic acid or an inorganic acid, filtering the resulting precipitate, and drying, or it may be prepared by distilling a solvent and an acid in excess amount under reduced pressure, then drying, and crystallizing under an organic solvent.

In addition, a pharmaceutically acceptable metal salt may be prepared by using a base. An alkali metal or alkaline earth metal salt is obtained, for example, by dissolving the compound in an alkali metal hydroxide or alkaline earth metal hydroxide solution in excess amount, filtering the undissolved compound salt, evaporating the filtrate, and drying. In this case, a sodium, potassium, or calcium salt is pharmaceutically suitable for preparing a metal salt. In addition, the corresponding salt is obtained by reacting an alkali metal or alkaline earth metal salt with an appropriate silver salt (for example, silver nitrate).

Furthermore, the present invention includes all the compound represented by Formula 1 and pharmaceutically acceptable salt thereof, as well as, a solvate, an optical isomer, a hydrate and the like that can be prepared therefrom.

In addition, the present invention provides a method for preparing the compound represented by Formula 1, comprising a step of reacting a compound represented by Formula 2 and a compound represented by Formula 3 to prepare the compound represented by Formula 1, as indicated in Reaction Scheme 1:

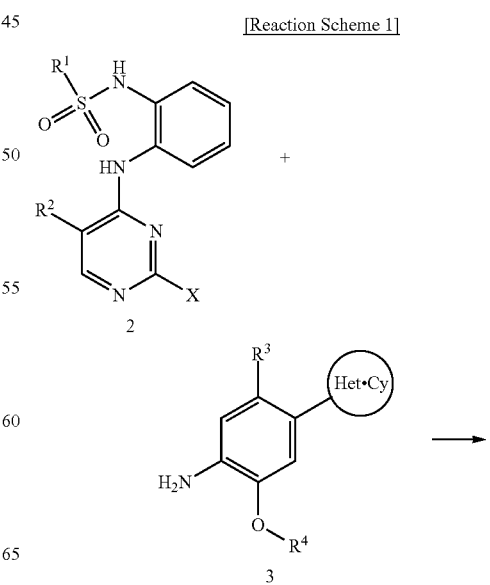

[Reaction Scheme 1]

13

-continued

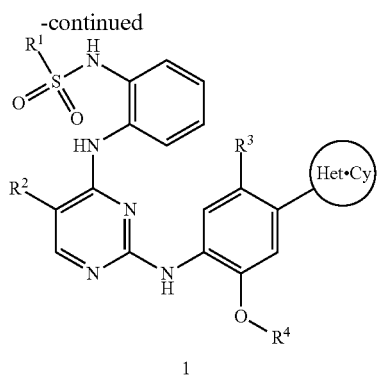

1 in which, $R^1$, $R^2$, $R^3$, $R^4$, and

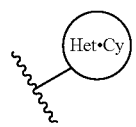

are as defined in Formula 1 of claim 1; and

X is halogen.

Hereinafter, the preparation method represented by Reaction Scheme 1 above will be described in detail.

In a method for preparing the compound according to the present invention represented by Reaction Scheme 1 above, Step 1 is a step of reacting a compound represented by Formula 2 and a compound represented by Formula 3 to prepare the compound represented by Formula 1. Specifically, it is a step of reacting a halogen of a compound represented by Formula 2 and a primary amine of a compound represented by Formula 3 to form the compound represented by Formula 1.

The reaction in Reaction Scheme 1 above is not particularly limited if the condition of the reaction is a condition under which an amine bond can be formed by binding a halogen and an amine.

The present invention uses an acid condition, and the acid used in the present invention is, but not limited to, hydrochloric acid.

In addition, as in the preparation method of Reaction Scheme 2 below, a sulfonamide can be introduced before the performance of the reaction of binding a halogen and an amine in Reaction Scheme 1, or a sulfonamide can be introduced after the performance of the reaction of binding a halogen and an amine without the introduction of a sulfonamide.

Solvents available in Reaction Scheme 1 above include, but are not particularly limited to, lower alcohols including isopropanol, methanol, ethanol, propanol, and butanol; tetrahydrofuran (THF); dioxane; ether solvents including ethyl ether, 1,2-dimethoxyethane and the like; dimethylformamide (DMF), dimethyl sulfoxide (DMSO), methylene chloride, dichloroethane, water, acetonitrile, benzene sulfonate, toluene sulfonate, chlorobenzene sulfonate, xylene sulfonate, ethyl acetate, phenylacetate, phenylpropionate, phenylbutyrate, citrate, lactate, hydroxybutyrate, glycolate, malate, tartrate, methane sulfonate, propane sulfonate, naphthalene-1-sulfonate, naphthalene-2-sulfonate, mandelate, acetonitrile and the like, which may be used alone or in combination herewith. A lower alcohol solvent is used in the present invention, but not limited hereto.

In addition, the compound represented by Formula 1 according to the present invention, wherein $R^1$ is $NH_2$, may be prepared by the preparation method comprising a step of reacting a compound represented by Formula 4 and a compound represented by Formula 3 to prepare a compound represented by Formula 5 (Step 1);

a step of reducing the compound represented by Formula 5 obtained in Step 1 above through a reduction reaction to prepare a compound represented by Formula 6 (Step 2);

a step of reacting the compound represented by Formula 6 obtained in Step 2 above with a compound represented by Formula 7 to prepare a compound represented by Formula 8 (Step 3); and a step of reacting the compound represented by Formula 8 obtained in Step 3 above to prepare the compound represented by Formula 1 (Step 4), as indicated in Reaction Scheme 2:

[Reaction Scheme 2]

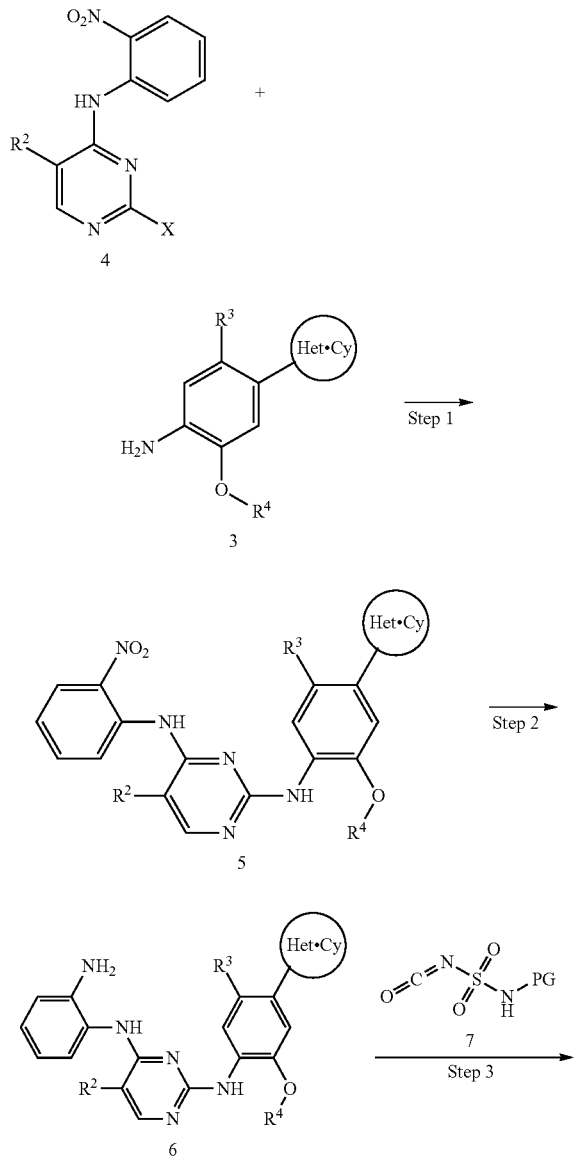

-continued

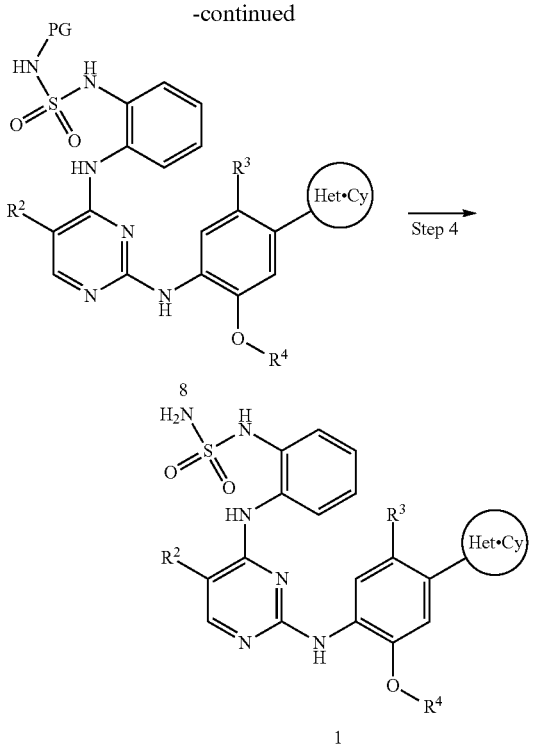

in which, $R^2$, $R^3$, $R^4$, and

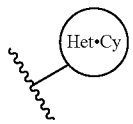

are as defined in Formula 1 above;

X is halogen; and

PG is an amine protecting group selected from the group consisting of t-butyloxycarbonyl (Boc), carbobenzyloxy (Cbz), 9-fluorenylmethyloxycarbonyl (Fmoc), acetyl (Ac), benzoyl (Bz), benzyl (Bn), p-methoxybenzyl (PMB), 3,4-dimethoxybenzyl (DMPM), p-methoxyphenyl (PMP), tosyl (Ts), 2,2,2-trichloroethoxycarbonyl (Troc), 2-trimethylsilylethoxycarbonyl (Teoc), and aryloxycarbonyl (Alloc).

Hereinafter, the preparation method represented by Reaction Scheme 2 above will be described in detail.

In the preparation method represented by Reaction Scheme 2 above according to the present invention, Step 1 above is a step of reacting a compound represented by Formula 4 and a compound represented by Formula 3 to prepare a compound represented by Formula 5. Specifically, it is a step of reacting a halogen of a compound represented by Formula 4 and a primary amine of a compound represented by Formula 3 to form a compound represented by Formula 5.

The reaction of Step 1 above is not particularly limited if the condition of the reaction is a condition under which an amine bond can be formed by binding a halogen and an amine.

The present invention uses an acid condition, and the acid used in the present invention is, but not limited to, hydrochloric acid.

Solvents available in Step 1 above include, but are not particularly limited to, lower alcohols including isopropanol, methanol, ethanol, propanol, and butanol; tetrahydrofuran (THF); dioxane; ether solvents including ethyl ether, 1,2-dimethoxyethane and the like; dimethylformamide (DMF), dimethyl sulfoxide (DMSO), methylene chloride, dichloroethane, water, acetonitrile, benzene sulfonate, toluene sulfonate, chlorobenzene sulfonate, xylene sulfonate, ethyl acetate, phenylacetate, phenylpropionate, phenylbutyrate, citrate, lactate, hydroxybutyrate, glycolate, malate, tartrate, methane sulfonate, propane sulfonate, naphthalene-1-sulfonate, naphthalene-2-sulfonate, mandelate, acetonitrile and the like, which may be used alone or in combination herewith. A lower alcohol solvent is used in the present invention, but not limited hereto.

In the preparation method represented by Reaction Scheme 2 above according to the present invention, Step 2 above is a step of reducing the compound represented by Formula 5 obtained in Step 1 above through a reduction reaction to prepare a compound represented by Formula 6. Specifically, it is a step of reducing a nitro of a compound represented by Formula 5 to a primary amine through a reduction reaction to form a compound represented by Formula 6.

The reduction reaction may be carried out by the publicly known method.

In the preparation method represented by Reaction Scheme 2 above according to the present invention, Step 3 above is a step of reacting the compound represented by Formula 6 obtained in Step 2 above with a compound represented by Formula 7 to prepare a compound represented by Formula 8. Specifically, it is a step of reacting a primary amine of a compound represented by Formula 6 with a chloro of tert-butyl chlorosulfonylcarbamate represented by Formula 7 to form a compound represented by Formula 8 in which a sulfonyl group is introduced.

In this case, the compound represented by Formula 7 above may be used either by purchasing as a commercially available product or by preparing by the publicly known method.

In the present invention, it is prepared by using chlorosulfonyl isocyanate and t-butanol, but not limited hereto.

Solvents available in Step 3 above include, but are not particularly limited to, lower alcohols including isopropanol, methanol, ethanol, propanol, and butanol; tetrahydrofuran (THF); dioxane; ether solvents including ethyl ether, 1,2-dimethoxyethane and the like; dimethylformamide (DMF), dimethyl sulfoxide (DMSO), methylene chloride, dichloroethane, water, acetonitrile, benzene sulfonate, toluene sulfonate, chlorobenzene sulfonate, xylene sulfonate, ethyl acetate, phenylacetate, phenylpropionate, phenylbutyrate, citrate, lactate, hydroxybutyrate, glycolate, malate, tartrate, methane sulfonate, propane sulfonate, naphthalene-1-sulfonate, naphthalene-2-sulfonate, mandelate, acetonitrile and the like, which may be used alone or in combination herewith.

In the preparation method represented by Reaction Scheme 2 above according to the present invention, Step 4 above is a step of reacting the compound represented by Formula 8 obtained in Step 3 above to prepare the compound represented by Formula 1. Specifically, it is a step of deprotecting an amine protecting group bound to an amine of sulfonyl in the compound represented by Formula 8 to obtain a compound represented by Formula 1.

The deprotecting reaction may be carried out by using a conventional deprotecting reaction condition.

The present invention uses an acid condition, and hydrochloric acid, sulfuric acid, methanesulfonic acid, trifluoroacetic acid and the like may be used as the acid.

In addition, solvents available in the above reaction include tetrahydrofuran, dioxane, dichloromethane, ether solvents, such as 1,2-dimethoxyethane and the like; aromatic hydrocarbon solvents, such as benzene, toluene, xylene and the like; alcohol solvents, such as methanol, ethanol and the like; dimethylformamide (DMF), dimethyl sulfoxide, acetonitrile, water and the like, which may be used alone or in combination herewith.

Furthermore, the present invention provides a pharmaceutical composition for the prevention or treatment of cancer, containing the compound represented by Formula 1, optical isomer thereof, or pharmaceutically acceptable salt thereof as an active ingredient.

In this case, the cancer is one or more selected from the group consisting of pseudomyxoma, intrahepatic cholangiocarcinoma, hepatoblastoma, liver cancer, thyroid cancer, colon cancer, testis cancer, myelodysplastic syndrome, glioblastoma, oral cancer, lip cancer, mycosis fungoides, acute myeloid leukemia, acute lymphocytic leukemia, basal cell carcinoma, epithelial ovarian cancer, ovarian seminoma, male breast cancer, brain cancer, pituitary adenoma, multiple myeloma, gallbladder cancer, cholangiocarcinoma, colorectal cancer, chronic myeloid leukemia, chronic lymphocytic leukemia, retinoblastoma, choroidal melanoma, ampullar of vater cancer, bladder cancer, peritoneal cancer, parathyroid cancer, adrenal cancer, nasal and paranasal cavity cancer, non-small cell lung cancer, tongue cancer, astrocytoma, small cell lung cancer, pediatric brain cancer, pediatric lymphoma, pediatric leukemia, small intestine cancer, meningioma, esophageal cancer, glioma, renal pelvis cancer, renal cancer, heart cancer, duodenal cancer, malignant soft tissue cancer, malignant bone cancer, malignant lymphoma, malignant mesothelioma, malignant melanoma, eye cancer, vulvar cancer, ureteral cancer, urethral cancer, cancer of unknown primary site, gastric lymphoma, gastric cancer, gastric carcinoid, gastrointestinal stromal tumor, Wilms' tumor, breast cancer, sarcoma, penile cancer, pharyngeal cancer, gestational choriocarcinoma, cervical cancer, endometrial cancer, uterine sarcoma, prostate cancer, metastatic bone cancer, metastatic brain cancer, mediastinal cancer, rectal cancer, rectal carcinoid, vaginal cancer, spinal cancer, vestibular schwannoma, pancreatic cancer, salivary gland cancer, Kaposi's sarcoma, Paget's disease, tonsillar cancer, squamous cell cancer, adenocarcinoma of lung, lung cancer, squamous cell lung cancer, skin cancer, anal cancer, rhabdomyosarcoma, laryngeal cancer, pleura cancer, hematologic malignancy, and thymic cancer, and the cancer may be a cancer with a mutation expressed on one or more selected from the group consisting of EGFR, anaplastic lymphoma kinase (ALK), focal adhesion kinase (FAK), fms-like tyrosine kinase 3 (FLT3), Janus kinase 3 (JAK3), tyrosine-protein kinase KIT (KIT), and polo-like kinase 4 (PLK4).

In this case, the EGFR mutation may be one or more selected from the group consisting of EGFR del19, EGFR del19/T790M, EGFR del19/T790M/C797S, EGFR L858R, EGFR L858R/T790MS, and EGFR L858R/T790M/C797S.

In this case, the FLT3 mutation may be one or more selected from the group consisting of FLT3(D835H), FLT3(D835V), FLT3(D835Y), FLT3(ITD), FLT3(ITD,D835V), FLT3(ITD,F691L), FLT3(K663Q), FLT3(N841I), and FLT3(R834Q).

A pharmaceutical composition for the prevention or treatment of cancer, containing the compound represented by Formula 1, optical isomer thereof, or pharmaceutically acceptable salt thereof as an active ingredient can be used either by the administration as an individual therapeutic agent or by the administration in combination with other anticancer agent in use.

A pharmaceutical composition for the prevention or treatment of cancer, containing the compound represented by Formula 1, optical isomer thereof, or pharmaceutically acceptable salt thereof as an active ingredient can enhance an anticancer effect by the administration in combination with an anticancer agent.

The compound represented by Formula 1 of the present invention shows a relatively weak EGFR activity inhibitory effect on wild-type EGFR, a selectively high inhibitory ability on EGFR mutation, and particularly, a high inhibitory ability on EGFR del19/T790M/C797S or EGFR L858R/T790M/C797S, which is a triple mutation (see Experimental Example 1 and Table 4).

The compound represented by Formula 1 of the present invention shows a selectively high inhibitory ability on EGFR mutation in Ba/F3 cell line, and particularly, a high inhibitory ability on EGFR del19, which is a single mutation (see Experimental Example 2 and Table 5).

The compound represented by Formula 1 of the present invention shows a selectively superior inhibitory ability on a kinase associated with cancer, particularly, FLT 3 kinase, which is a kinase associated with hematologic malignancy, and a high inhibitory ability on wild-type FLT3, as well as, FLT3(D835H), FLT3(D835V), FLT3(D835Y), FLT3(ITD), FLT3(ITD,D835V), FLT3(ITD,F691L), FLT3(K663Q), FLT3(N841I), FLT3(R834Q), which are mutation forms (see Experimental Example 3 and Table 6).

It can be seen that the compound represented by Formula 1 of the present invention shows a lower cell viability on Ba/F3 Del19/T790M/C797S cell line with EGFR triple mutation when administered alone than a conventional drug, and shows a remarkably decreased cell viability when administered in combination with a conventional drug than when administered alone, and thus, shows a superior cancer cell apoptosis ability on a cell line with EGFR triple mutation even when administered alone, as well as, shows a remarkably elevated anticancer effect when administered in combination with a conventional drug. In particular, it can be seen that the compound represented by Formula 1 of the present invention shows a cell viability decreased by at least 20% than when administering brigatinib, which is a conventional drug in use, in combination with a conventional drug, and thus, shows a superior anticancer effect than brigatinib (see Experimental Example 4 and FIGS. 1 to 4).

It can be seen that the compound represented by Formula 1 of the present invention shows a concentration-dependent activity in pERK, pAKT, pS6, which is EGFR sub-signal, even when administered alone, as well as, shows a superior activity when administered in combination with a conventional drug. In particular, it can be seen that the compound represented by Formula 1 of the present invention shows a superior activity than when administering brigatinib, which is a conventional drug in use, in combination with a conventional drug, and thus, shows a superior anticancer effect than brigatinib (see Experimental Example 4 and FIGS. 5 to 7).

Therefore, the compound represented by Formula 1 according to the present invention shows a high inhibitory ability on EGFR mutation, and thus, can be effectively used for the treatment of cancer with EGFR mutation, such as EGFR del19, EGFR del19/T790M, EGFR del19/T790M/C797S, EGFR L858R, EGFR L858R/T790MS, EGFR L858R/T790M/C797S and the like. In particular, the compound represented by Formula 1 according to the present invention shows a remarkably superior inhibitory ability on EGFR del19/T790M/C797S or EGFR L858R/T790M/C797S, which is a triple mutation, and thus, can be effectively used for the treatment of cancer with EGFR del19/T790M/C797S or EGFR L858R/T790M/C797S.

In addition, the compound represented by Formula 1 according to the present invention shows a high inhibitory ability on FLT 3 and mutation thereof, such as FLT3 (D 835H), FLT3(D835V), FLT3(D835Y), FLT3 (ITD), FLT3 (ITD,D835V), FLT3(ITD,F691L), FLT3(K663Q), FLT3 (N841I), or FLT3(R834Q), and thus, can be effectively used for the treatment of cancer associated with an activity of FLT 3 or a mutation form of FLT 3, particularly hematologic malignancy.

In addition, the compound represented by Formula 1 according to the present invention shows a synergy effect when administered in combination with a conventional drug, and thus, can be effectively used when administered in combination with a conventional drug.

The compound represented by Formula 1 or pharmaceutically acceptable salt thereof may be administered in various oral and parenteral formulations upon clinical administration. It is prepared by using diluents or excipients, such as fillers, bulking agents, binders, wetting agents, disintegrating agents, surfactants and the like, which are generally used in the formulation. Solid formulations for oral administration include tablets, pills, powders, granules, capsules and the like. These solid formulations are prepared by mixing at least one or more excipients, for example, starch, calcium carbonate, sucrose or lactose, gelatin and the like to one or more compounds. Furthermore, in addition to simple excipients, lubricants such as magnesium stearate, talc and the like are also used. Liquid formulations for oral administration include suspensions, oral solutions, emulsions, syrups and the like. In addition to simple diluents, such as water and liquid paraffin, which are commonly used, various excipients, for example wetting agents, sweetening agents, perfuming agents, preservatives and the like may be included. Formulations for parenteral administration include sterilized aqueous solutions, non-aqueous solvents, suspensions, emulsions. Propylene glycol, polyethylene glycol, vegetable oils, such as olive oil, injectable ester, such as ethyl oleate and the like can be used as non-aqueous solvents, suspending solvents.

A pharmaceutical composition containing the compound represented by Formula 1 or pharmaceutically acceptable salt thereof as an active ingredient may be parenterally administered, and parenteral administration is by infusion methods of subcutaneous injection, intravenous injection, intramuscular injection, or intrathoracic injection.

In this case, in order to formulate the formulations for parenteral administration, the compound represented by Formula 1 or pharmaceutically acceptable salt thereof is mixed with a stabilizer or buffer in water to prepare a solution or suspension, and it may be manufactured in an ampoule or vial unit dosage form. The composition may be sterilized and/or contain preservatives, stabilizers, wetting agents or emulsifying accelerators, adjuvants, such as salts and/or buffers for regulating osmotic pressure and the like, and other therapeutically useful substances, and may be formulated according to a conventional method of mixing, granulation, or coating method.

Formulations for oral administration include, for example, tablets, pills, hard/soft capsules, solutions, suspensions, emulsions, syrups, granules, elixirs, troches and the like. These formulations contain, in addition to an active ingredient, diluents (for example, lactose, dextrose, sucrose, mannitol, sorbitol, cellulose, and/or glycine) and glidants (for example, silica, talc, stearic acid and magnesium or calcium salt thereof, and/or polyethylene glycol). The tablets may contain binders, such as magnesium aluminum silicate, starch paste, gelatin, methylcellulose, sodium carboxymethylcellulose, and/or polyvinylpyrrolidine and the like, and may contain, where appropriate, disintegrating agents, such as starch, agar, alginic acid or sodium salt thereof and the like, or effervescent mixtures and/or absorbents, colorants, flavoring agents, and sweetening agents.

In addition, the present invention provides a health functional food for the prevention or amelioration of cancer, containing the compound represented by Formula 1, optical isomer thereof, or pharmaceutically acceptable salt thereof as an active ingredient.

The cancer is one or more selected from the group consisting of pseudomyxoma, intrahepatic cholangiocarcinoma, hepatoblastoma, liver cancer, thyroid cancer, colon cancer, testis cancer, myelodysplastic syndrome, glioblastoma, oral cancer, lip cancer, mycosis fungoides, acute myeloid leukemia, acute lymphocytic leukemia, basal cell carcinoma, epithelial ovarian cancer, ovarian seminoma, male breast cancer, brain cancer, pituitary adenoma, multiple myeloma, gallbladder cancer, cholangiocarcinoma, colorectal cancer, chronic myeloid leukemia, chronic lymphocytic leukemia, retinoblastoma, choroidal melanoma, ampullar of vater cancer, bladder cancer, peritoneal cancer, parathyroid cancer, adrenal cancer, nasal and paranasal cavity cancer, non-small cell lung cancer, tongue cancer, astrocytoma, small cell lung cancer, pediatric brain cancer, pediatric lymphoma, pediatric leukemia, small intestine cancer, meningioma, esophageal cancer, glioma, renal pelvis cancer, renal cancer, heart cancer, duodenal cancer, malignant soft tissue cancer, malignant bone cancer, malignant lymphoma, malignant mesothelioma, malignant melanoma, eye cancer, vulvar cancer, ureteral cancer, urethral cancer, cancer of unknown primary site, gastric lymphoma, gastric cancer, gastric carcinoid, gastrointestinal stromal tumor, Wilms' tumor, breast cancer, sarcoma, penile cancer, pharyngeal cancer, gestational choriocarcinoma, cervical cancer, endometrial cancer, uterine sarcoma, prostate cancer, metastatic bone cancer, metastatic brain cancer, mediastinal cancer, rectal cancer, rectal carcinoid, vaginal cancer, spinal cancer, vestibular schwannoma, pancreatic cancer, salivary gland cancer, Kaposi's sarcoma, Paget's disease, tonsillar cancer, squamous cell cancer, adenocarcinoma of lung, lung cancer, squamous cell lung cancer, skin cancer, anal cancer, rhabdomyosarcoma, laryngeal cancer, pleura cancer, and thymic cancer; and more preferably, the cancer may be a cancer with mutation on one or more selected from the group consisting of EGFR, ALK, FAK, FLT3, JAK3, KIT, and PLK4.

The compound represented by Formula 1 according to the present invention shows a high inhibitory ability on EGFR mutation, and thus, can be added to health functional foods, such as foods, beverages and the like, as a health functional food composition for the prevention or amelioration of cancer, particularly cancer with EGFR mutation.

The compound represented by Formula 1 according to the present invention may be added to foods as it is, or may be used with other foods or food ingredients, and may be appropriately used according to conventional methods. The mixing amount of the active ingredient may be suitably determined depending on the purpose of use thereof (for the prevention or amelioration). Generally, the amount of the compound in health foods may be added in 0.1 to 90 parts by weight of a total weight of foods. However, the amount may be less than the above range in case of long-term ingestion for health and hygiene, or for health regulation, and the active ingredient may be also used in amount more than the above range because there is no problem in regard to safety.

In addition, the health functional beverage composition of the present invention may contain, in addition to the above compound as an essential ingredient in the indicated ratio, other ingredients, which are not particularly limited. The health functional beverage composition of the present invention may contain various flavoring agents or natural carbohydrates and the like as additional ingredients, as conventional beverages have. Examples of the aforementioned natural carbohydrates are conventional sugars, such as monosaccharides, for example glucose, fructose and the like; disaccharides, for example maltose, sucrose and the like; and polysaccharides, for example dextrin, cyclodextrin and the like, and sugar alcohols, such as xylitol, sorbitol, erythritol and the like. As flavoring agents in addition to those described above, natural flavoring agents (thaumatin, stevia extract (for example, rebaudioside A, glycyrrhizin and the like) and synthetic flavoring agents (saccharin, aspartame and the like) can be effectively used. The ratio of the natural carbohydrate is generally about 1 to 20 g per 100 g of the composition of the present invention, preferably about 5 to 12 g.

Furthermore, the health functional beverage composition of the present invention may contain, in addition to those described above, various nutrients, vitamins, minerals (electrolytes), flavoring agents, such as synthetic flavoring agents and natural flavoring agents and the like, colorants and enhancers (cheese, chocolate and the like), pectic acids and salts thereof, alginic acids and salts thereof, organic acids, protective colloidal thickening agents, pH adjusting agents, stabilizers, preservatives, glycerin, alcohol, carbonating agents used in carbonated beverages and the like. Besides, the health functional beverage composition of the present invention may contain fruit flesh for the preparation of natural fruit juice and fruit juice beverage and vegetable beverage.

In addition, the present invention provides a method for the prevention or treatment of cancer, comprising a step of administering a pharmaceutical composition or a health functional food composition containing the compound represented by Formula 1 or pharmaceutically acceptable salt thereof as an active ingredient to a subject in need thereof.

In addition, the present invention provides a use of a pharmaceutical composition or a health functional food composition containing the compound represented by Formula 1 or pharmaceutically acceptable salt thereof in the prevention or treatment of cancer.

Embodiment for Working the Invention

Hereinafter, the present invention will be described in detail through the Examples and Experimental Examples.

However, the following Examples and Experimental Examples are only illustrations of the present invention, and the contents of the present invention are not limited to the following Examples and Experimental Examples.

The compounds of Example 1 and 2 were prepared according to Reaction Example 1 below.

[Reaction Example 1]

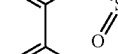

In which, $R^3$=H indicates the compound of Example 1, and $R^3$=CH$_3$ indicates the compound of Example 2.

<Example 1> Preparation of N-(2-((5-chloro-2-((2-methoxy-4-(piperidin-4-yl)phenyl)amino)pyrimidin-4-yl)amino)phenyl)methanesulfonamide Step 1: Preparation of N-(2-((2, 5-dichloropyrimidin-4-yl)amino)phenyl)methanesulfonamide N-(2-aminophenyl)methanesulfonamide (18.6 mg, 0.1 mmol), 2,4,5-trichloropyrimidine (14 μL, 0.12 mmol), and DIPEA (diisopropyl ethyl amine, 38 μL, 0.22 mmol) were mixed with isopropyl alcohol (1 mL). The above reaction mixture was stirred overnight at 60° C. The above mixture was concentrated under reduced pressure. The residue was purified by silica gel flash column chromatography (CH$_2$Cl$_2$/EtOAc, 5:1) to obtain N-(2-((2,5-dichloropyrimidin-4-yl)amino)phenyl)methanesulfonamide (15 mg, white solid) in a yield of 42%.

$^1$H NMR (300 MHz, CDCl$_3$) δ 8.38 (br s, 1H), 8.24 (s, 1H), 8.05 (d, J=7.5 Hz, 1H), 7.46-7.37 (m, 2H), 7.31-7.29 (m, 1H), 6.56 (s, 1H), 3.08 (s, 3H); LC-MS calcd for C$_1$H$_{10}$Cl$_2$N$_4$O$_2$S 332.0, found 333.0 (M+H$^+$)

Step 2: Preparation of N-(2-((5-chloro-2-((2-methoxy-4-(piperidin-4-yl)phenyl)amino)pyrimidin-4-yl)amino)phenyl) methanesulfonamide To n-butanol (1 mL) of N-(2-((2,5-dichloropyrimidin-4-yl)amino)phenyl)methanesulfonamide (5.0 mg, 0.015 mmol) and tert-butyl 4-(4-amino-3-methoxyphenyl)piperidine-1-carboxylate (5.0 mg, 0.016 mmol) was added a dioxane solution (0.15 mL, 0.012 mmol) of 0.08 N HCl. The above reaction mixture was stirred overnight at 95° C. The above mixture was concentrated under reduced pressure, and the residue was purified by prep-HPLC to obtain N-(2-((5-chloro-2-((2-methoxy-4-(piperidin-4-yl)phenyl)amino)pyrimidin-4-yl)amino)phenyl) methanesulfonamide (2.2 mg, white solid) in a yield of 30%.

$^1$H NMR (500 MHz, CD$_3$OD) δ 8.12 (s, 1H), 7.81 (d, J=8.8 Hz, 1H), 7.63-7.60 (m, 1H), 7.54-7.52 (m, 1H), 7.41-7.36 (m, 2H), 6.93 (s, 1H), 6.70 (d, J=7.5 Hz, 1H), 3.90 (s, 3H), 3.53 (d, J=12.6 Hz, 2H), 3.18-3.13 (m, 2H), 2.96 (s, 3H), 2.93-2.88 (m, 1H), 2.11-2.08 (m, 2H), 1.95-1.88 (m, 2H); LC-MS calcd for C$_{23}$H$_{27}$ClN$_6$O$_3$S 502.2, found 503.2 (M+H$^+$)

<Example 2> Preparation of N-(2-((5-chloro-2-((2-methoxy-5-methyl-4-(piperidin-4-yl)phenyl)amino)pyrimidin-4-yl) amino)phenyl)methanesulfonamide The same manner as in Example 1 above was performed to obtain N-(2-((5-chloro-2-((2-methoxy-5-methyl-4-(piperidin-4-yl)phenyl)amino)pyrimidin-4-yl)amino)phenyl) methanesulfonamide (28 mg, 30%).

$^1$H NMR (300 MHz, CD$_3$OD) δ 8.16 (s, 1H), 7.74 (d, J=7.8 Hz, 1H), 7.57 (dd, J=7.8, 1.5 Hz, 1H), 7.43 (td, J=7.8, 1.5 Hz, 1H), 7.36 (td, J=7.8, 1.5 Hz, 1H), 7.32 (s, 1H), 6.91 (s, 1H), 3.89 (s, 3H), 3.55 (d, J=12.6 Hz, 2H), 3.27-3.14 (m, 3H), 2.97 (s, 3H), 2.16 (s, 3H), 2.00-1.97 (m, 4H); LC-MS calcd for C$_{24}$H$_{29}$ClN$_6$O$_3$S 516.2, found 516.8 (M+H$^+$)

The compound of Example 3 was prepared according to Reaction Example 2 below.

<Example 3> Preparation of N-(2-((5-bromo-2-((2-methoxy-4-(piperidin-4-yl)phenyl)amino)pyrimidin-4-yl)amino)phenyl)methanesulfonamide Step 1: Preparation of N-(2-((5-bromo-2-chloropyrimidin-4-yl)amino)phenyl)methanesulfonamide The same manner as in Step 1 of Example 1 above was performed to obtain N-(2-((5-bromo-2-chloropyrimidin-4-yl)amino)phenyl)methanesulfonamide (25 mg, 30%).

$^1$H NMR (300 MHz, CDCl$_3$) δ 8.35 (s, 1H), 8.03 (dd, J=8.3, 1.0 Hz, 1H), 7.46-7.38 (m, 2H), 7.31-7.26 (m, 1H), 6.57 (s, 1H), 3.08 (s, 3H); LC-MS calcd for C$_{11}$H$_{10}$BrClN$_4$O$_2$S 375.9, found 376.9 (M+H$^+$)

Step 2: Preparation of N-(2-((5-bromo-2-((2-methoxy-4-(piperidin-4-yl)phenyl)amino)pyrimidin-4-yl)amino)phenyl) methanesulfonamide The same manner as in Step 2 of Example 1 above was performed to obtain N-(2-((5-bromo-2-((2-methoxy-4-(piperidin-4-yl)phenyl)amino)pyrimidin-4-yl)amino)phenyl) methanesulfonamide (13 mg, 37%).

$^1$H NMR (300 MHz, CD$_3$OD) δ 8.11 (s, 1H), 7.65 (d, J=7.5 Hz, 1H), 7.42 (dd, J=7.8, 1.3 Hz, 1H), 7.33-7.21 (m, 3H), 6.85 (s, 1H), 6.61 (d, J=7.9 Hz, 1H), 3.77 (s, 3H), 3.43 (d, J=12.7 Hz, 2H), 3.08-3.01 (m, 2H), 2.86 (s, 3H), 2.83-2.77 (m, 1H), 1.99-1.80 (m, 4H); LC-MS calcd for C$_{23}$H$_{27}$BrN$_6$O$_3$S 546.1, found 546.7 (M+H$^+$)

The compound of Example 4 was prepared according to Reaction Example 3 below.

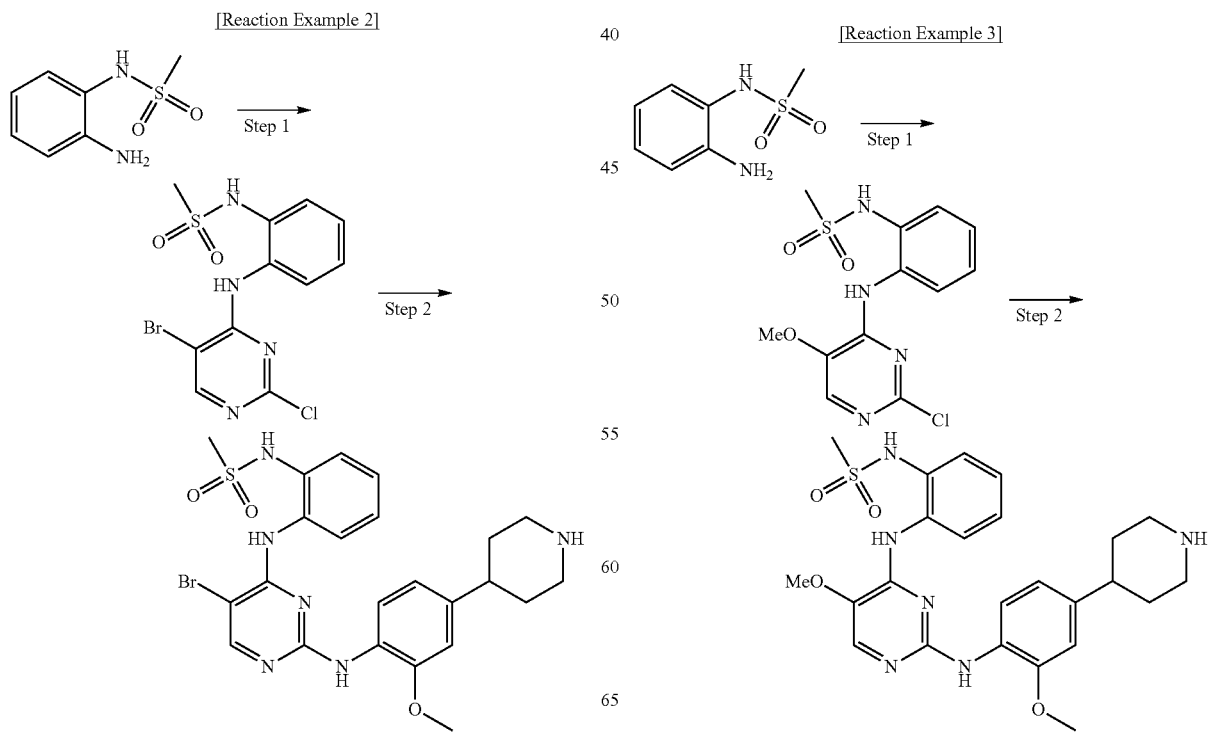

<Example 4> Preparation of N-(2-((5-methoxy-2-((2-methoxy-4-(piperidin-4-yl)phenyl)amino)pyrimidin-4-yl)amino) phenyl)methanesulfonamide Step 1: Preparation of N-(2-((2-chloro-5-methoxy pyrimidin-4-yl)amino)phenyl)methanesulfonamide The same manner as in Step 1 of Example 1 above was performed to obtain N-(2-((2-chloro-5-methoxypyrimidin-4-yl)amino)phenyl)methanesulfonamide (6 mg, 8%).

$^1$H NMR (300 MHz, CDCl$_3$) δ 7.98-7.95 (m, 2H), 7.79 (s, 1H), 7.45 (dd, J=7.9, 0.8 Hz, 1H), 7.38 (td, J=7.4, 1.0 Hz, 1H), 6.67 (s, 1H), 4.02 (s, 3H), 3.08 (s, 3H); LC-MS calcd for C$_{12}$H$_{13}$ClN$_4$O$_3$S 328.0, found 328.9 (M+H$^+$)

Step 2: Preparation of N-(2-((5-methoxy-2-((2-methoxy-4-(piperidin-4-yl)phenyl)amino)pyrimidin-4-yl)amino)phenyl)methanesulfonamide The same manner as in Step 2 of Example 1 above was performed to obtain N-(2-((5-methoxy-2-((2-methoxy-4-(piperidin-4-yl)phenyl)amino)pyrimidin-4-yl)amino)phenyl)methanesulfonamide (5.5 mg, 58%).

$^1$H NMR (300 MHz, CD$_3$OD) δ 7.87-7.84 (m, 1H), 7.53 (s, 1H), 7.51-7.45 (m, 2H), 7.39-7.34 (m, 2H), 6.98 (d, J=1.5 Hz, 1H), 6.78 (dd, J=8.3, 1.5 Hz, 1H), 3.99 (s, 3H), 3.89 (s, 3H), 3.55-3.51 (m, 2H), 3.20-3.11 (m, 2H), 2.97 (s, 3H), 2.94-2.90 (m, 1H), 2.21-1.90 (m, 4H); LC-MS calcd for C$_{24}$H$_{30}$N$_6$O$_4$S 498.2, found 498.8 (M+H$^+$)

The compound of Example 5 was prepared according to Reaction Example 4 below.

[Reaction Example 4]

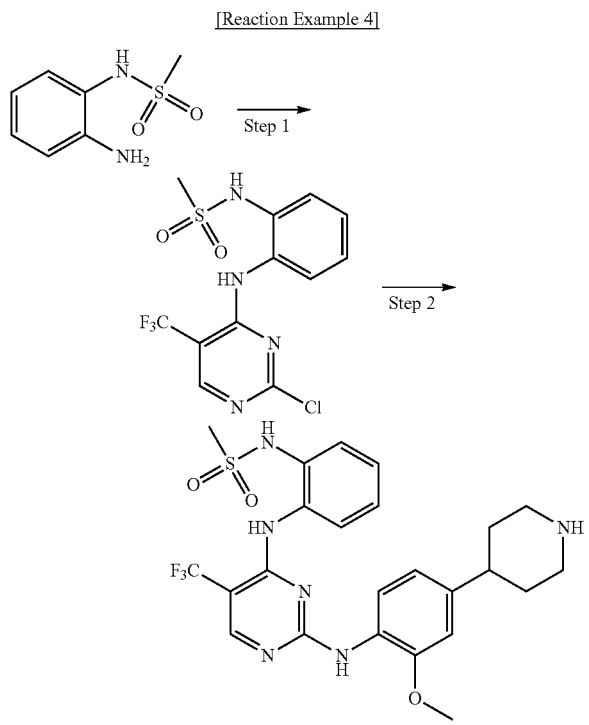

<Example 5> Preparation of N-(2-((2-((2-methoxy-4-(piperazin-1-yl)phenyl)amino)-5-(trifluoromethyl)pyrimidin-4-yl) amino)phenyl)methanesulfonamide Step 1: Preparation of N-(2-((2-chloro-5-(trifluoromethyl)pyrimidin-4-yl)amino)phenyl)methanesulfonamide The same manner as in Step 1 of Example 1 above was performed to obtain N-(2-((2-chloro-5-(trifluoromethyl)pyrimidin-4-yl)amino)phenyl)methanesulfonamide (199 mg, 18%).

$^1$H NMR (300 MHz, CDCl$_3$) δ 8.47 (s, 1H), 8.23 (br s, 1H), 7.92 (d, J=7.8 Hz, 1H), 7.46-7.28 (m, 3H), 6.27 (br s, 1H), 3.05 (s, 3H); LC-MS calcd for C$_{12}$H$_{10}$ClF$_3$N$_4$O$_2$S 366.0, found 366.8 (M+H$^+$)

Step 2: Preparation of N-(2-((2-((2-methoxy-4-(piperidin-4-yl)phenyl)amino)-5-(trifluoromethyl)pyrimidin-4-yl)amino)phenyl)methanesulfonamide The same manner as in Step 2 of Example 1 above was performed to obtain N-(2-((2-((2-methoxy-4-(piperidin-4-yl)phenyl)amino)-5-(trifluoromethyl)pyrimidin-4-yl)amino)phenyl)methanesulfonamide (15 mg, 31%).

$^1$H NMR (300 MHz, CD$_3$OD) δ 8.38 (s, 1H), 7.60 (d, J=7.8 Hz, 1H), 7.48 (dd, J=7.8, 1.8 Hz, 1H), 7.42-7.29 (m, 3H), 6.89 (s, 1H), 6.60 (br s, 1H), 3.83 (s, 3H), 3.49 (dd, J=10.2, 3.3 Hz, 2H), 3.11 (td, J=12.9, 3.3 Hz, 2H), 2.89-2.85 (m, 4H), 2.04-1.81 (m, 4H); LC-MS calcd for C$_{24}$H$_{27}$F$_3$N$_6$O$_3$S 536.2, found 536.8 (M+H$^+$)

The compound of Example 6 was prepared according to Reaction Example 5 below.

[Reaction Example 5]

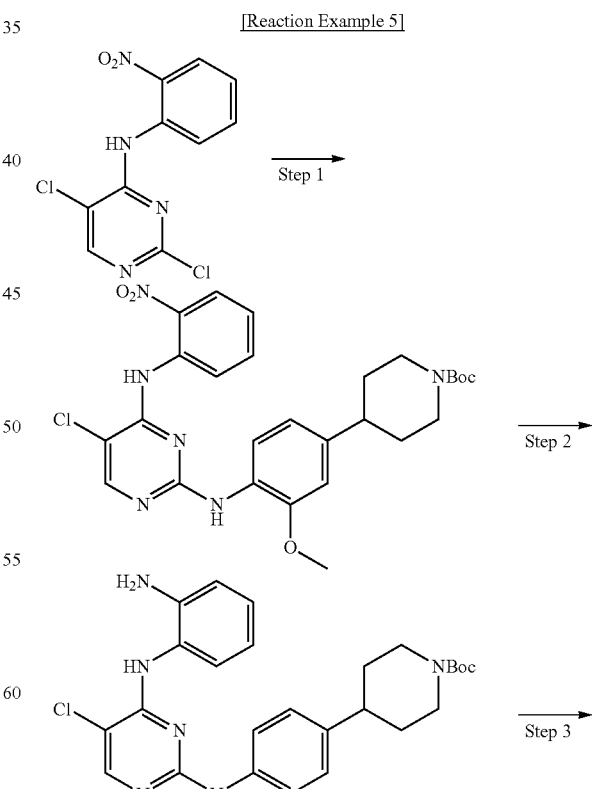

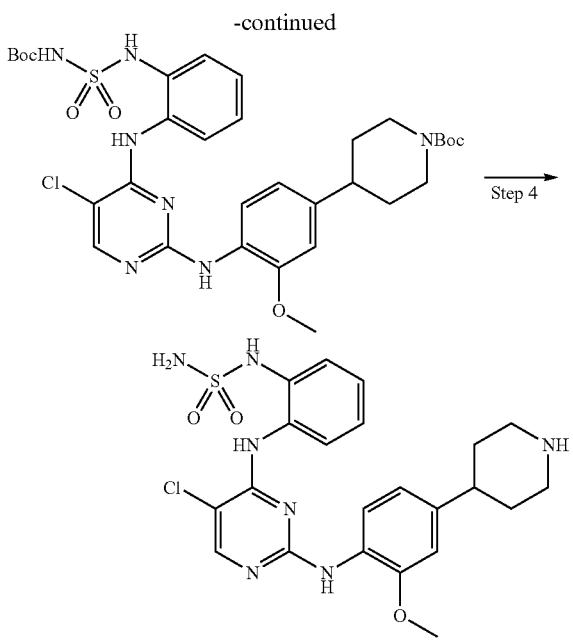

<Example 6> Preparation of 4-(4-((5-chloro-4-((2-(sulfamoylamino)phenyl)amino)pyrimidin-2-yl)amino)-3-methoxyphenyl)piperidine Step 1: Preparation of tert-butyl 4-(4-((5-chloro-4-((2-nitrophenyl)amino)pyrimidin-2-yl)amino)-3-methoxy phenyl)piperidine-1-carboxylate To n-butanol (10 mL) of 2,5-dichloro-N-(2-nitrophenyl) pyrimidin-4-amine (1.0 g, 3.5 mmol) and tert-butyl 4-(4-amino-3-methoxyphenyl)piperidine-1-carboxylate (1.1 g, 3.5 mmol) was added a 1,4-dioxane solution (0.7 mL, 2.8 mmol) of 4 N HCl. The above reaction mixture was stirred overnight at 95° C. The above reactant was concentrated under reduced pressure. To the residual solution concentrated under reduced pressure was added $CH_2Cl_2$ (10 mL), and di-tert-butyl dicarbonate (1.2 g, 5.3 mmol) and $Et_3N$ (0.98 mL, 7.0 mmol) were added at 0° C. and stirred overnight at ambient temperature. The above mixture was diluted in methylene chloride (200 mL), was washed with a saturated $NaHCO_3$ aqueous solution (100 mL), and then, was washed with water (100 mL). The above organic layer was dried over anhydrous $MgSO_4$ and concentrated under vacuum to obtain tert-butyl 4-(4-((5-chloro-4-((2-nitrophenyl)amino)pyrimidin-2-yl)amino)-3-methoxy phenyl)piperidine-1-carboxylate (1.0 g) in a yield of 57%.

$^1$H NMR (300 MHz, $CDCl_3$) δ 10.61 (s, 1H), 8.95 (d, J=8.5 Hz, 1H), 8.29 (dd, J=8.4, 1.4 Hz, 1H), 8.23 (s, 1H), 8.15 (d, J=8.1 Hz, 1H), 7.67-7.61 (m, 1H), 7.50 (s, 1H), 7.22-7.17 (m, 1H), 6.81-6.77 (m, 2H), 4.31-4.25 (m, 2H), 3.92 (s, 3H), 2.83 (t, J=12.2 Hz, 2H), 2.65 (dt, J=12.1, 3.4 Hz, 1H), 1.88-1.84 (m, 2H), 1.72-7.62 (m, 2H), 1.51 (s, 9H); LC-MS calcd for $C_{27}H_{31}ClN_6O_5$ 554.2, found 555.0 (M+H$^+$)

Step 2: Preparation of tert-butyl 4-(4-((4-((2-aminophenyl)amino)-5-chloropyrimidin-2-yl)amino)-3-methoxy phenyl)piperidine-1-carboxylate Tert-butyl 4-(4-((5-chloro-4-((2-nitrophenyl)amino)pyrimidin-2-yl)amino)-3-methoxy phenyl)piperidine-1-carboxylate (1.4 g, 2.4 mmol) obtained in Step 1 above, iron powder (0.68 g, 12 mmol), and $NH_4Cl$ (0.65 g, 12 mmol) were added to THF/$H_2O$ (1:1, 24 mL). The above reaction mixture was stirred for 1 hour at 60° C. After completion of the reaction, the above reaction mixture was filtered through celite and concentrated under vacuum. The above residue was washed with water and filtered to obtain tert-butyl 4-(4-((4-((2-aminophenyl)amino)-5-chloropyrimidin-2-yl)amino)-3-methoxyphenyl)piperidine-1-carboxylate (0.50 g) in a yield of 53% without a separate purification process.

LC-MS calcd for $C_{27}H_{33}ClN_6O_3$ 524.2, found 525.0 (M+H$^+$)

Step 3: Preparation of tert-butyl 4-(4-((4-((2-4N-(tert-butoxycarbonyl)sulfamoyl)amino)phenyl)amino)-5-chloropyrimidin-2-yl)amino)-3-methoxyphenyl)piperidine-1-carboxylate To an anhydrous methylene chloride (1 mL) solution of chlorosulfonyl isocyanate (8.7 μL, 0.1 mmol) was added dropwise anhydrous methylene chloride (1 mL) of t-butanol (9.5 uL, 0.1 mmol) at 0° C. The above mixture was stirred for 30 minutes at 0° C., and $Et_3N$ (16 uL, 0.11 mmol) was added and stirred for 30 minutes at 0° C. The above reaction solution was added slowly at 0° C. to a methylene chloride (1 mL) solution of tert-butyl 4-(4-((4-((2-aminophenyl)amino)-5-chloropyrimidin-2-yl)amino)-3-methoxyphenyl)piperidine-1-carboxylate (26 mg, 0.05 mmol) obtained in Step 2 above. The above mixture was stirred for 3 hours at ambient temperature. The above reaction mixture was diluted in methylene chloride (20 mL) and washed with water (10 mL). The above organic layer was dried over anhydrous $MgSO_4$ and concentrated under vacuum. The residue was purified by silica gel flash column chromatography ($CH_2Cl_2$/EtOAc, 5:1) to obtain tert-butyl 4-(4-((4-((2-4N-(tert-butoxycarbonyl)sulfamoyl)amino)phenyl)amino)-5-chloropyrimidin-2-yl)amino)-3-methoxyphenyl)piperidine-1-carboxylate (17 mg, white solid) in a yield of 49%.

$^1$H NMR (300 MHz, $(CD_3)_2SO$) δ 8.13 (s, 1H), 7.97-7.92 (m, 1H), 7.89-7.85 (m, 1H), 7.71 (d, J=7.8 Hz, 1H), 7.26-7.13 (m, 3H), 6.88 (s, 1H), 6.67 (d, J=8.3 Hz, 1H), 4.08 (d, J=12.3 Hz, 2H), 3.80 (s, 3H), 2.86-2.72 (m, 2H), 2.68-2.58 (m, 1H), 1.74 (d, J=12.3 Hz, 2H), 1.57-1.46 (m, 2H), 1.42 (s, 9H), 1.39 (s, 9H); LC-MS calcd for $C_{32}H_{42}ClN_7O_7S$ 703.3, found 704.8 (M+H$^+$)

Step 4: Preparation of 4-(4-((5-chloro-4-((2-(sulfamoylamino)phenyl)amino)pyrimidin-2-yl)amino)-3-methoxyphenyl)piperidine $CH_2Cl_2$/trifluoroacetic acid (1:1, 1 mL) of tert-butyl 4-(4-((4-((2-((N-(tert-butoxycarbonyl)sulfamoyl)amino)phenyl)amino)-5-chloropyrimidin-2-yl)amino)-3-methoxyphenyl)piperidine-1-carboxylate (4 mg, 0.006 mmol) obtained in Step 3 above was stirred for 2 hours at ambient temperature. To the above reaction mixture was added 1,4-dioxane (10 μL) of 4 N HCl. The above reaction mixture was concentrated under vacuum to obtain 4-(4-(5-chloro-4-((2-(sulfamoylamino)phenyl)amino)pyrimidin-2-yl)amino)-3-methoxy phenyl)piperidine (4.2 mg, white solid) in a quantitative yield.

$^1$H NMR (300 MHz, CD$_3$OD) δ 8.13 (s, 1H), 7.83 (d, J=7.6 Hz, 1H), 7.53 (d, J=8.3 Hz, 2H), 7.39-7.27 (m, 2H), 6.98 (s, 1H), 6.78 (d, J=8.0 Hz, 1H), 3.89 (s, 3H), 3.53 (d, J=12.3 Hz, 2H), 3.16 (t, J=12.0 Hz, 2H), 2.94 (m, 1H), 2.12 (m, 2H), 2.02-1.91 (m, 2H); LC-MS calcd for C$_{22}$H$_{26}$ClN$_7$O$_3$S 503.2, found 503.8 (M+H$^+$)

The compound of Example 7 was prepared according to Reaction Example 6 below.

[Reaction Example 6]

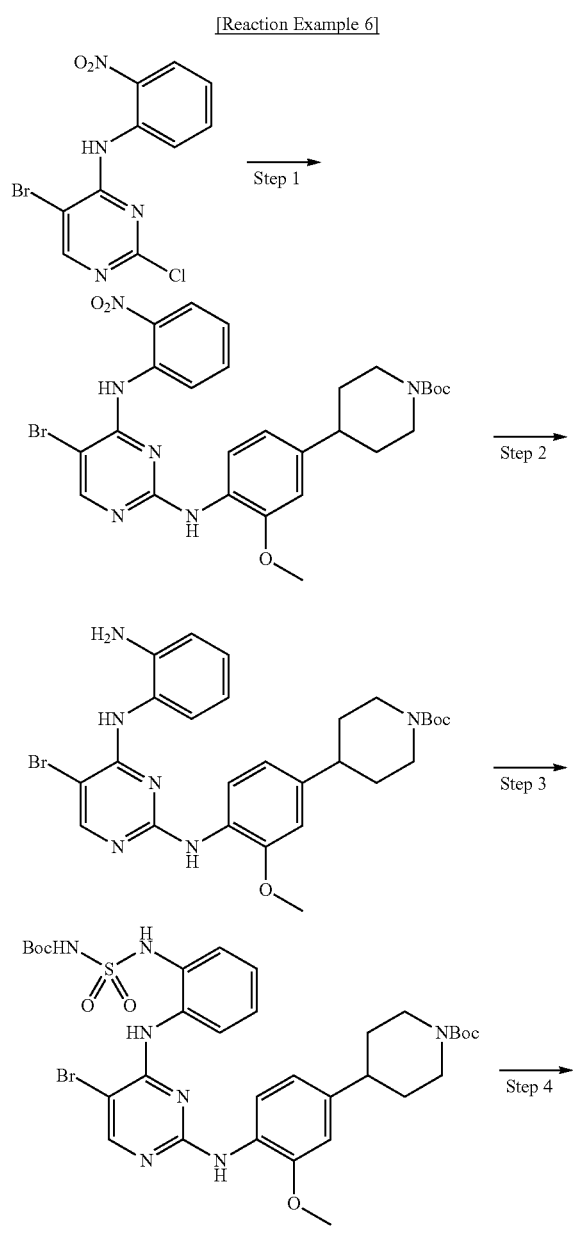

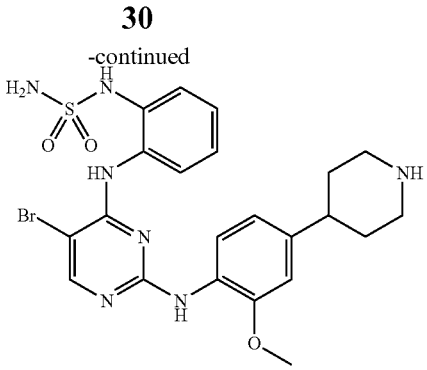

<Example 7> Preparation of 4-(4-((5-bromo-4-((2-(sulfamoylamino)phenyl)amino)pyrimidin-2-yl)amino)-3-methoxy phenyl)piperidine Step 1: Preparation of tert-butyl 4-(4-((5-bromo-4-((2-nitrophenyl)amino)pyrimidin-2-yl)amino)-3-methoxyphenyl)piperidine-1-carboxylate The same manner as in Step 1 of Example 6 above was performed to obtain tert-butyl 4-(4-((5-bromo-4-((2-nitrophenyl)amino)pyrimidin-2-yl)amino)-3-methoxy phenyl)piperidine-1-carboxylate (68 mg, 58%).

$^1$H NMR (300 MHz, CDCl$_3$) δ 10.52 (s, 1H), 8.90 (d, J=8.7 Hz, 1H), 8.29 (s, 1H), 8.26 (dd, J=8.4, 1.0 Hz, 1H), 8.12 (d, J=8.6 Hz, 1H), 7.62 (t, J=7.5 Hz, 1H), 7.52 (s, 1H), 7.18 (t, J=7.5 Hz, 1H), 6.78-6.76 (m, 2H), 4.27 (d, J=11.2 Hz, 2H), 3.91 (s, 3H), 2.82 (t, J=12.3 Hz, 2H), 2.68-2.60 (m, 1H), 1.85 (d, J=12.3 Hz, 2H), 1.71-1.57 (m, 2H), 1.50 (s, 9H); LC-MS calcd for C$_{27}$H$_{31}$BrN$_6$O$_5$ 598.2, found 599.7 (M+H$^+$)

Step 2: Preparation of tert-butyl 4-(4-((4-((2-aminophenyl)amino)-5-bromopyrimidin-2-yl)amino)-3-methoxy phenyl)piperidine-1-carboxylate The same manner as in Step 2 of Example 6 above was performed to obtain tert-butyl 4-(4-((4-((2-aminophenyl)amino)-5-bromopyrimidin-2-yl)amino)-3-methoxy phenyl)piperidine-1-carboxylate (60 mg, 94%).

LC-MS calcd for C$_{27}$H$_{33}$BrN$_6$O$_3$ 568.2, found 569.8 (M+H$^+$)

Step 3: Preparation of tert-butyl 4-(4-(5-bromo-4-((2-4N-(tert-butoxy carbonyl)sulfamoyl)amino)phenyl)amino)pyrimidin-2-yl)amino)-3-methoxy phenyl)piperidine-1-carboxylate The same manner as in Step 3 of Example 6 above was performed to obtain tert-butyl 4-(4-((5-bromo-4-((2-4N-(tert-butoxy carbonyl)sulfamoyl)amino)phenyl)amino)pyrimidin-2-yl)amino)-3-methoxyphenyl)piperidine-1-carboxylate (30 mg, 70%).

$^1$H NMR (500 MHz, CD$_3$OD) δ 8.12 (s, 1H), 7.93 (d, J=8.0 Hz, 1H), 7.80 (d, J=8.1 Hz, 1H), 7.42 (d, J=8.0 Hz, 1H), 7.34 (t, J=7.2 Hz, 1H), 7.27 (t, J=8.1 Hz, 1H), 6.83 (s, 1H), 6.61 (d, J=8.0 Hz, 1H), 4.22 (d, J=13.0 Hz, 2H), 3.87 (s, 3H), 2.89-2.86 (m, 2H), 2.70-2.65 (m, 1H), 1.81 (d, J=12.3 Hz, 2H), 1.63-1.57 (m, 2H), 1.50 (s, 9H), 1.49 (s, 9H); LC-MS calcd for C$_{32}$H$_{42}$BrN$_7$O$_7$S 747.2, found 749.6 (M+H$^+$)

Step 4: Preparation of 4-(4-((5-bromo-4-((2-(sulfa-moylamino)phenyl)amino)pyrimidin-2-yl)amino)-3-methoxyphenyl)piperidine The same manner as in Step 4 of Example 6 above was performed to obtain 4-(4-((5-bromo-4-((2-(sulfamoylamino)phenyl)amino)pyrimidin-2-yl)amino)-3-methoxyphenyl)piperidine (24 mg, quantitative yield).

$^1$H NMR (300 MHz, CD$_3$OD) δ 8.21 (s, 1H), 7.85-7.83 (m, 1H), 7.53-7.27 (m, 5H), 6.99 (s, 1H), 6.80-6.78 (m, 1H), 3.89 (s, 3H), 3.54 (d, J=12.3 Hz, 2H), 3.21-3.12 (m, 2H), 2.99-2.90 (m, 1H), 2.10 (d, J=13.4 Hz, 2H), 2.02-1.87 (m, 2H); LC-MS calcd for C$_{22}$H$_{26}$BrN$_7$O$_3$S 547.1, found 547.7 (M+H$^+$)

The compound of Example 8 was prepared according to Reaction Example 7 below.

[Reaction Example 7]

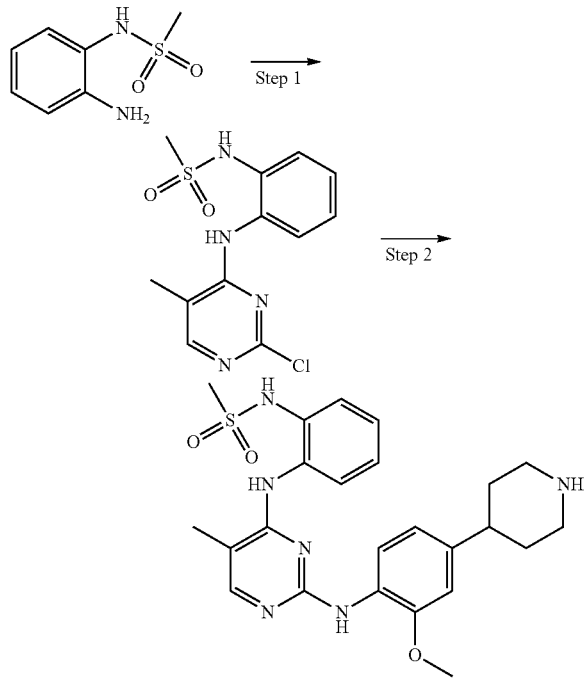

<Example 8> Preparation of N-(2-((2-((2-methoxy-4-(piperidin-4-yl)phenyl)amino))-5-methylpyrimidin-4-ylamino)phenyl)methanesulfonamide Step 1: Preparation of N-(2-((2-chloro-5-methylpyrimidin-4-yl)amino)phenyl)methanesulfonamide The same manner as in Step 1 of Example 1 above was performed to obtain N-(2-((2-chloro-5-methylpyrimidin-4-yl)amino)phenyl)methanesulfonamide in a yield of 26%.

$^1$H NMR (300 MHz, CDCl$_3$) δ 9.37 (s, 1H), 8.62 (s, 1H), 8.21 (sd, J=0.9 Hz, 1H), 7.64-7.60 (m, 1H), 7.49-7.45 (m, 1H), 7.32-7.24 (m, 2H), 2.97 (s, 3H), 2.17 (sd, J=0.9 Hz, 1H); LC-MS calcd for C$_{12}$H$_{13}$ClN$_4$O$_2$S 312.0, found 312.9 (M+H$^+$)

Step 2: Preparation of N-(2-((2-((2-methoxy-4-(piperidin-4-yl)phenyl)amino))-5-methylpyrimidin-4-ylamino)phenyl)methanesulfonamide The same manner as in Step 2 of Example 1 above was performed to obtain N-(2-((2-((2-methoxy-4-(piperidin-4-yl)phenyl)amino))-5-methylpyrimidin-4-ylamino)phenyl)methanesulfonamide in a yield of 65%.

$^1$H NMR (300 MHz, CD$_3$OD) δ 9.54 (br s, 1H), 9.49 (br s, 1H), 9.26 (sd, J=3.6 Hz, 1H), 8.75 (br s, 1H), 8.58 (br s, 1H), 7.89 (s, 1H), 7.54 (dd, J=8.4, 3.3 Hz, 1H), 7.45 (dd, J=8.4, 3.0 Hz, 1H), 7.41-7.35 (m, 1H), 7.32-7.23 (m, 2H), 6.88 (s, 1H), 6.52 (sd, J=5.7 Hz, 1H), 3.80 (s, 3H), 3.38 (d, J=12.6 Hz, 2H), 3.05-2.76 (m, 6H), 2.18 (s, 3H), 1.92-1.75 (m, 4H); LC-MS calcd for C$_{24}$H$_{30}$N$_6$O$_3$S 482.2, found 483.0 (M+H$^+$)

The compound of Example 9 was prepared according to Reaction Example 8 below.

[Reaction Example 8]

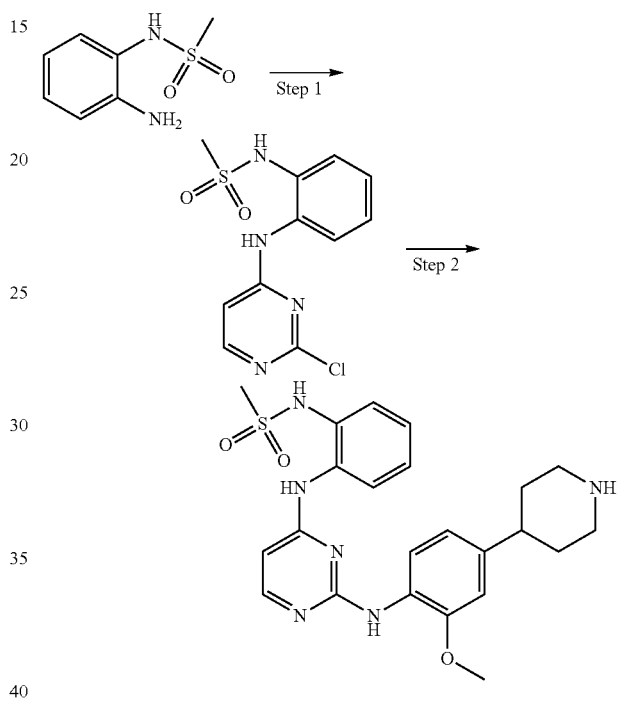

<Example 9> Preparation of N-(2-((2-((2-methoxy-4-(piperidin-4-yl)phenyl)amino)pyrimidin-4-yl)amino)phenyl)methanesulfonamide Step 1: Preparation of N-(2-((2-chloropyrimidin-4-yl)amino)phenyl)methanesulfonamide The same manner as in Step 1 of Example 1 above was performed to obtain N-(2-((2-chloropyrimidin-4-yl)amino)phenyl)methanesulfonamide (white solid) in a yield of 47%.

$^1$H NMR (300 MHz, CDCl$_3$) δ 9.28 (s, 1H), 9.13 (s, 1H), 8.12 (d, J=6.0 Hz, 1H), 7.56-7.44 (m, 2H), 7.29-7.23 (m, 2H), 6.67 (d, J=5.7 Hz, 1H), 2.97 (s, 3H); LC-MS calcd for C$_{11}$H$_{11}$ClN$_4$O$_2$S 298.0, found 298.9 (M+H$^+$)

Step 2: Preparation of N-(2-((2-((2-methoxy-4-(piperidin-4-yl)phenyl)amino)pyrimidin-4-yl)amino)phenyl)methane sulfonamide The same manner as in Step 2 of Example 1 above was performed to obtain N-(2-((2-((2-methoxy-4-(piperidin-4-yl)phenyl)amino)pyrimidin-4-yl)amino)phenyl)methane sulfonamide in a yield of 65%.

$^1$H NMR (300 MHz, CD$_3$OD) δ 10.27 (s, 1H), 9.74 (s, 1H), 9.26 (s, 1H), 8.78 (d, J=10.8 Hz, 1H), 8.59 (d, J=10.8 Hz, 1H), 7.96 (d, J=7.2 Hz, 1H), 7.54-7.46 (m, 3H), 7.36-7.21 (m, 2H), 6.93 (s, 1H), 6.66 (d, J=8.1 Hz, 1H), 6.47 (br s, 1H), 3.82 (s, 3H), 3.39 (d, J=12.6 Hz, 2H), 3.06-2.95 (m,

5H), 2.87-2.79 (m, 1H), 1.95-1.78 (m, 4H); LC-MS calcd for C$_{23}$H$_{28}$N$_6$O$_3$S 468.2, found 469.0 (M+H$^+$)

The compound of Example 10 was prepared according to Reaction Example 9 below.

[Reaction Example 9]

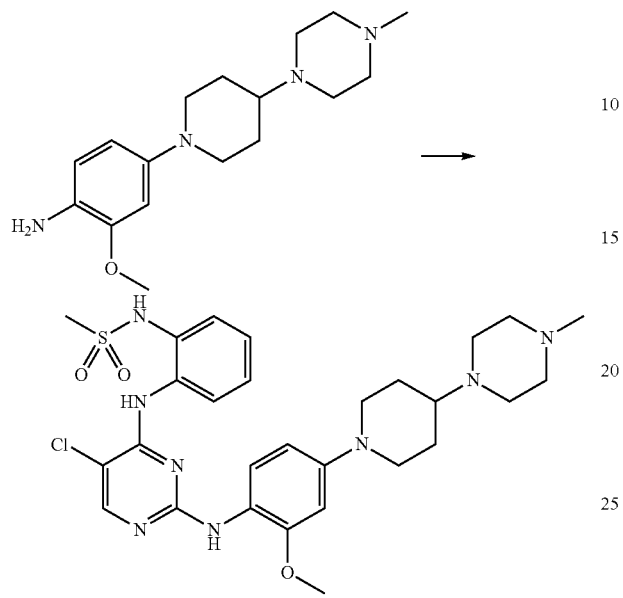

<Example 10> Preparation of N-(2-((5-chloro-2-((2-methoxy-4-(4-(4-methylpiperazin-1-yl)piperidin-1-yl)phenyl)amino)pyrimidin-4-yl)amino)phenyl)methanesulfonamide The same manner as in Step 2 of Example 1 above was performed to obtain N-(2-((5-chloro-2-((2-methoxy-4-(4-(4-methylpiperazin-1-yl)piperidin-1-yl)phenyl)amino)pyrimidin-4-yl)amino)phenyl)methanesulfonamide (51.3 mg, 57%).

$^1$H NMR (300 MHz, CD$_3$OD) δ 8.10 (s, 1H), 7.74 (dd, J=7.4, 2.2 Hz, 1H), 7.53 (dd, J=7.4, 2.1 Hz, 1H), 7.48 (d, J=8.7 Hz, 1H), 7.43 (td, J=7.4, 1.9 Hz, 1H), 7.36 (td, J=7.5, 1.9 Hz, 1H), 6.92 (sd, J=2.5 Hz, 1H), 6.67 (dd, J=8.9, 2.5 Hz, 1H), 3.88 (s, 3H), 3.82 (d, J=12.4 Hz, 2H), 3.43 (br s, 4H), 3.24-3.04 (m, 7H), 2.96 (s, 3H), 2.92 (s, 3H), 2.19 (d, J=12.7, 2H), 1.99-1.86 (m, 2H); LC-MS calcd C$_{25}$H$_{37}$ClN$_8$O$_3$S 600.2, found 601.0 (M+H$^+$)

The compound of Example 11 was prepared according to Reaction Example 10 below.

[Reaction Example 10]

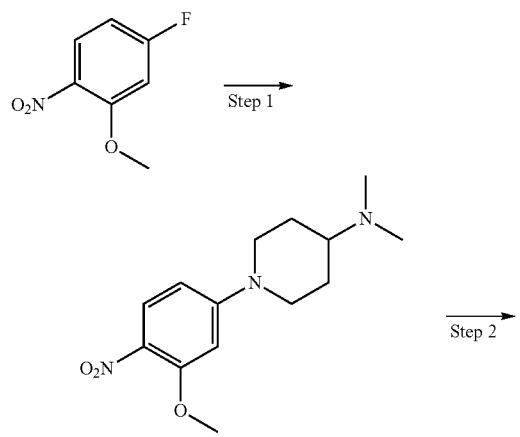

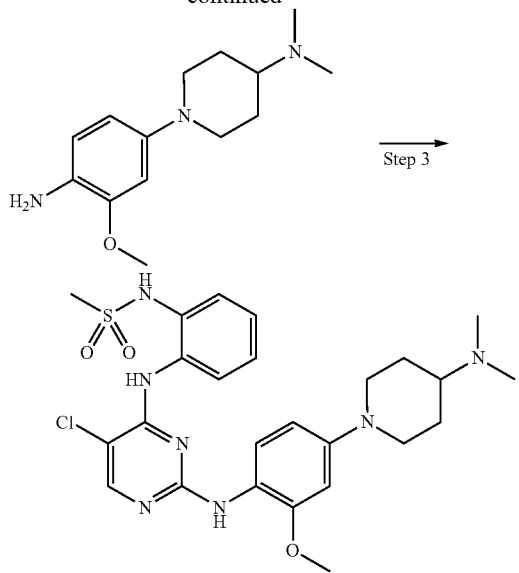

<Example 11> Preparation of N-(2-((5-chloro-2-((4-(4-(dimethylamino)piperidin-1-yl)-2-methoxyphenyl)amino)pyrimidin-4-yl)amino)phenyl)methanesulfonamide Step 1: Preparation of 1-(3-methoxy-4-nitrophenyl)-N,N-dimethylpiperidin-4-amine The reaction tube containing DMF (30 mL) of a mixture of 4-fluoro-2-methoxy-1-nitrobenzene (5.00 g, 29.22 mmol), N,N-dimethylpiperidin-4-amine (6.53 g, 35.06 mmol), and K$_2$CO$_3$ (6.06 g, 43.83 mmol) was sealed with a Teflon-lined cap, and the above reaction mixture was stirred for 2 hours at 90° C. The above mixture was concentrated under reduced pressure. The above reaction mixture was diluted in ethyl acetate (300 mL), washed with water (100 mL), and then, washed with brine (100 mL). The residue was purified by silica gel flash column chromatography (CH$_2$Cl$_2$/MeOH, 9:1) to obtain 1-(3-methoxy-4-nitrophenyl)-N,N-dimethylpiperidin-4-amine (9.73 g, pale yellow solid) in a yield of 99%.

$^1$H NMR (300 MHz, CDCl$_3$) δ 7.99 (d, J=9.4 Hz, 1H), 6.42 (dd, J=9.4, 2.6 Hz, 1H), 6.31 (sd, J=2.5 Hz, 1H), 3.94 (s, 3H), 3.92 (d, J=13.0 Hz, 2H), 2.97 (td, J=12.3, 2.8 Hz, 2H), 2.43-2.33 9 (m, 1H), 2.30 (s, 6H), 1.95 (d, J=13.0 Hz, 2H), 1.58 (qd, J=11.9, 4.0 Hz, 2H); LC-MS calcd for C$_{14}$H$_{21}$N$_3$O$_3$ 279.2, found 280.0 (M+H$^+$)

Step 2: Preparation of 1-(4-amino-3-methoxyphenyl)-N,N-dimethylpiperidin-4-amine The same manner as in Step 2 of Example 6 above was performed to obtain 1-(4-amino-3-methoxyphenyl)-N,N-dimethylpiperidin-4-amine (8.50 mg, 96%).

LC-MS calcd for C$_{14}$H$_{24}$N$_3$O 249.2, found 250.0 (M+H$^+$)

Step 3: Preparation of N-(2-((5-chloro-2-((4-(4-(dimethylamino)piperidin-1-yl)-2-methoxyphenyl)amino)pyrimidin-4-yl)amino)phenyl)methanesulfonamide The same manner as in Step 2 of Example 1 above was performed to obtain N-(2-((5-chloro-2-((4-(4-(dimethylamino)piperidin-1-yl)-2-methoxyphenyl)amino)pyrimidin-4-yl)amino)phenyl)methanesulfonamide (46.7 mg, 57%).

¹H NMR (300 MHz, CD₃OD) δ 8.04 (s, 1H), 7.77 (d, J=7.5 Hz, 1H), 7.52 (dd, J=7.5, 2.0 Hz, 1H), 7.42-7.32 (m, 2H), 7.25 (d, J=8.7, 1H), 6.70 (sd, J=2.5 Hz 1H), 6.50 (d, J=8.7 Hz, 1H), 3.90 (d, J=12.8 Hz, 2H), 3.84 (s, 3H), 3.44-3.34 (m, 1H), 2.97 (s, 3H), 2.92-2.82 (m, 8H), 2.25 (d, J=12.1 Hz, 1H), 1.93-1.79 (m, 2H); LC-MS calcd for C₂₅H₃₂ClN₇O₃S 545.2, found 546.0 (M+H⁺)

The compound of Example 12 was prepared according to Reaction Example 11 below.

[Reaction Example 11]

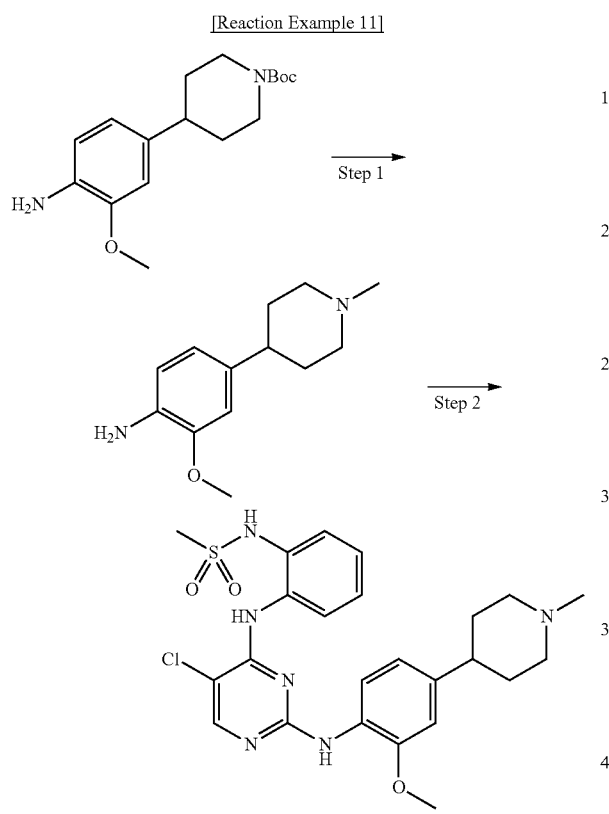

<Example 12> Preparation of N-(2-((5-chloro-2-((2-methoxy-4-(1-methylpiperidin-4-yl)phenyl)amino)pyrimidin-4-yl)amino)phenyl)methanesulfonamide Step 1: Preparation of 2-methoxy-4-(1-methylpiperidin-4-yl)aniline To a tetrahydrofuran (18 mL) suspension of lithium tetrahydroaluminate (619.3 mg, 16.3 mmol) was added tetrahydrofuran (18 mL) of tert-butyl 4-(4-amino-3-methoxyphenyl)piperidine-1-carboxylate (500 mg, 1.63 mmol) at 0° C. The above reaction tube was sealed with a Teflon-lined cap, and the above reaction mixture was stirred for 6 hours at 90° C. The above reaction mixture was cooled, Na₂SO₄10H₂O (3 g) was slowly added, and it was stirred for 30 minutes at ambient temperature. The above mixture was filtered and washed with dichloromethane. The above organic layer was dried over anhydrous MgSO₄ and concentrated under vacuum to obtain 2-methoxy-4-(1-methylpiperidin-4-yl)aniline (319.4 mg, brown solid) in a yield of 89%.

¹H NMR (300 MHz, CD₃OD) δ 6.68-6.64 (m, 3H), 3.82 (s, 3H), 2.98-2.92 (m, 2H), 2.43-2.34 (m, 1H), 2.31 (s, 3H), 2.07-1.98 (m, 2H), 1.82-1.77 (m, 4H); LC-MS calcd for C₁₃H₂₀N₂O 220.2, found 221.1 (M+H⁺)

Step 2: Preparation of N-(2-((5-chloro-2-((2-methoxy-4-(1-methylpiperidin-4-yl)phenyl)amino)pyrimidin-4-yl)amino)phenyl)methanesulfonamide The same manner as in Step 2 of Example 1 above was performed to obtain N-(2-((5-chloro-2-((2-methoxy-4-(1-methylpiperidin-4-yl)phenyl)amino)pyrimidin-4-yl)amino)phenyl)methanesulfonamide (55.1 mg, 71%).

¹H NMR (300 MHz, CD₃OD) δ 8.12 (s, 1H), 7.75 (dd, J=7.4, 2.2 Hz, 1H), 7.52 (d, J=8.6 Hz, 2H), 7.41-7.31 (m, 2H), 6.92 (sd, J=1.8 Hz, 1H), 6.69 (d, J=8.6 Hz, 1H), 3.87 (s, 3H), 3.63 (d, J=12.2 Hz 1H), 3.15 (td, J=12.1, 3.1 Hz, 2H), 2.94 (s, 3H), 2.93 (s, 3H), 2.89-2.82 (m, 1H), 2.11 (d, J=14.2 Hz, 2H), 2.03-1.89 (m, 2H); LC-MS calcd for C₂₄H₂₉ClN₆O₃S 516.2, found 516.9 (M+H⁺)

The compound of Example 13 was prepared according to Reaction Example 12 below.

[Reaction Example 12]

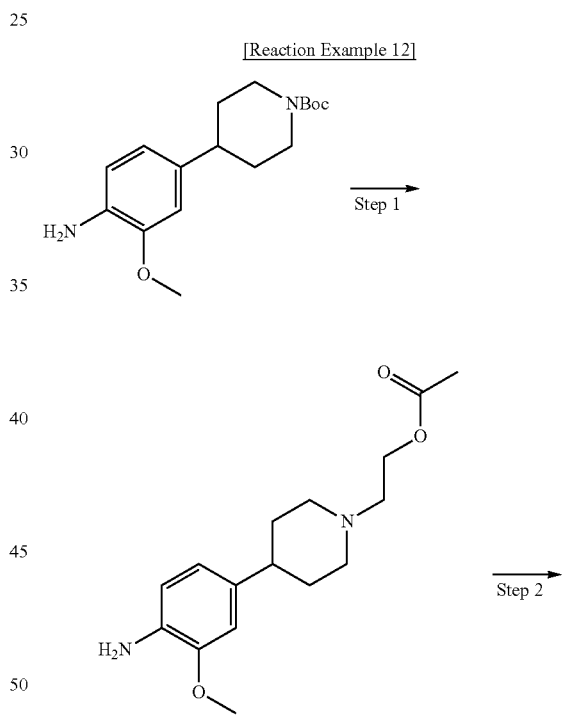

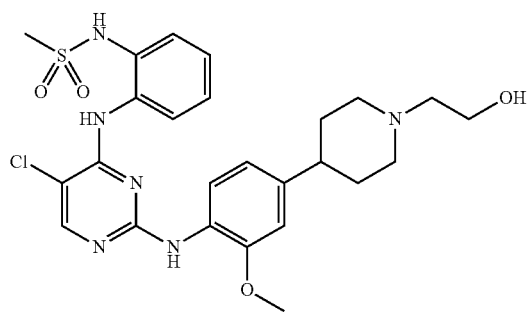

<Example 13> Preparation of N-(2-((5-chloro-2-((4-(1-(2-hydroxyethyl)piperidin-4-yl)-2-methoxyphenyl)amino)pyrimidin-4-yl)amino)phenyl)methanesulfonamide

Step 1: Preparation of 2-(4-(4-amino-3-methoxyphenyl)piperidin-1-yl)ethyl acetate CH₂Cl₂/trifluoroacetic acid (1:1, 1 mL) of tert-butyl 4-(4-amino-3-methoxyphenyl)piperidine-1-carboxylate 30 (300 mg, 0.98 mmol) was stirred for 2 hours at ambient temperature. The above reactant was concentrated under reduced pressure. To an acetonitrile (10 mL) solution of the above residue were added 2-bromoethyl acetate (140 μL, 1.22 mmol) and potassium carbonate (1.00 g, 7.83 mmol) over 4 hours at 95° C. The above mixture was concentrated under reduced pressure. The above reaction mixture was diluted in ethyl acetate (100 mL) and washed with water (50 mL). The residue was purified by silica gel flash column chromatography (CH₂Cl₂/MeOH, 9:1) to obtain 2-(4-(4-amino-3-methoxyphenyl)piperidin-1-yl)ethyl acetate (125.8 mg, pale yellow oil) in a yield of 44%.

$^1$H NMR (300 MHz, CDCl₃) δ 6.66 (m, 3H), 4.23 (t, J=6.1 Hz, 2H), 3.83 (s, 3H), 3.68 (br s, 2H), 3.04 (dt, J=11.3, 2.8 Hz, 2H), 2.67 (t, J=6.0 Hz, 2H), 2.40 (tt, J=10.3, 5.1 Hz, 1H), 2.20-2.10 (m, 2H), 2.08 (s, 3H), 1.84-1.75 (m, 4H); LC-MS calcd C₁₆H₂₄N₂O₃ 292.2, found 293.0 (M+H⁺)

Step 2: Preparation of N-(2-((5-chloro-2-((4-(1-(2-hydroxyethyl)piperidin-4-yl)-2-methoxy phenyl)amino)pyrimidin-4-yl)amino)phenyl)methanesulfonamide The same manner as in Step 2 of Example 1 above was performed to obtain N-(2-((5-chloro-2-((4-(1-(2-hydroxyethyl)piperidin-4-yl)-2-methoxy phenyl)amino)pyrimidin-4-yl)amino)phenyl)methanesulfonamide (74 mg, 61%).

$^1$H NMR (300 MHz, CD₃OD) δ 8.12 (s, 1H), 7.74 (dd, J=7.5, 2.0 Hz, 1H), 7.54-7.49 (m, 2H), 7.42-7.31 (m, 2H), 6.93 (sd, J=1.8 Hz, 1H), 6.70 (d, J=8.3 Hz, 1H), 3.94-3.91 (m, 2H), 3.87 (s, 3H), 3.74 (d, J=12.5 Hz, 2H), 3.30-3.28 (m, 2H), 3.16 (td, J=12.6, 3.6 Hz, 2H), 2.94 (s, 3H), 2.92-2.86 (m, 1H), 2.14-1.97 (m, 4H); LC-MS calcd C₂₅H₃₁ClN₆O₄S 546.2, found 547.4 (M+H⁺)

The compound of Example 14 was prepared according to Reaction Example 13 below.

[Reaction Example 13]

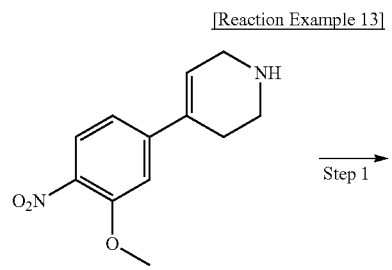

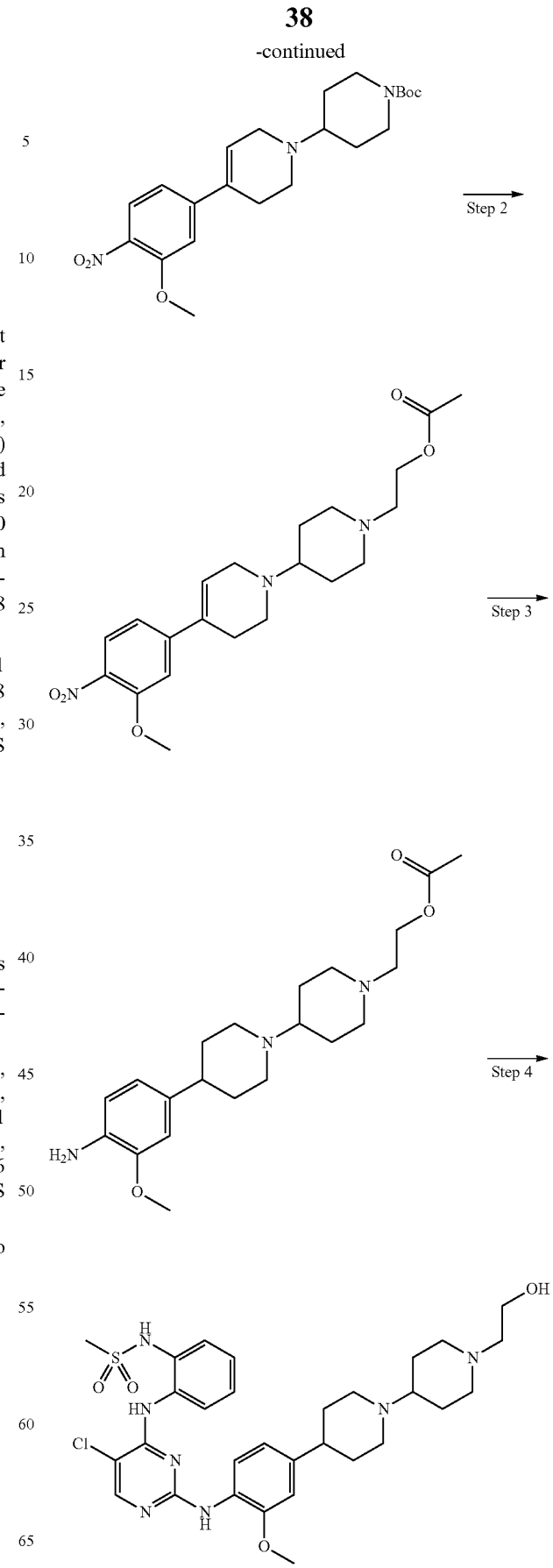

\<Example 14\> Preparation of N-(2-((5-chloro-2-((4-(1'-(2-hydroxyethyl)-[1,4'-bipiperidin]-4-yl)-2-methoxyphenyl)amino)pyrimidin-4-yl)amino)phenyl)methanesulfonamide

Step 1: Preparation of tert-butyl 4-(4-(3-methoxy-4-nitrophenyl)-3,6-dihydropyridin-1 (2H)-yl)piperidine-1-carboxylate 4-(3-methoxy-4-nitrophenyl)-1,2,3,6-tetrahydropyridine (1.29 g, 5.51 mmol), 1-boc-4-piperidone (2.19 g, 11.01 mmol), dichloromethane 1 M solution (170 µL, 17.62 mmol) of acetic acid, and 1,2-dichloroethane (20 mL) of triethylamine (730 µL, 5.23 mmol) were stirred for 1 hour at ambient temperature, and then, sodium triacetoxyborohydride (1.75 g, 8.26 mmol) was added. The above reaction mixture was stirred overnight at ambient temperature. The above mixture was diluted with methylene chloride (200 mL), washed with a saturated NaHCO$_3$ aqueous solution (100 mL), and then, washed with water (100 mL). The above organic layer was dried over anhydrous MgSO$_4$ and concentrated under vacuum, and the residue was purified by silica gel flash column chromatography (CH$_2$Cl$_2$/MeOH, 9:1) to obtain tert-butyl 4-(4-(3-methoxy-4-nitrophenyl)-3,6-dihydropyridin-1 (2H)-yl)piperidine-1-carboxylate (1.11 g, pale brown solid) in a yield of 50%.

LC-MS calcd C$_{22}$H$_{31}$N$_3$O$_5$ 417.2, found 418.0 (M+H$^+$)

Step 2: Preparation of 2-(4-(4-(4-amino-3-methoxyphenyl)-3,6-dihydropyridin-1 (2H)-yl)piperidin-1-yl)ethyl acetate The same manner as in Step 2 of Example 13 above was performed to obtain 2-(4-(4-(4-amino-3-methoxyphenyl)-3,6-dihydropyridin-1 (2H)-yl)piperidin-1-yl)ethyl acetate (536.6 mg, 50%).

LC-MS calcd C$_{21}$H$_{29}$N$_3$O$_5$, 403.2, found 404.1 (M+H$^+$)

Step 3: Preparation of 2-(4-(4-amino-3-methoxyphenyl)-[1,4'-bipiperidin]-1'-yl)ethyl acetate To methanol (10 mL) of 2-(4-(4-(4-amino-3-methoxyphenyl)-3,6-dihydropyridin-1 (2H)-yl)piperidin-1-yl)ethyl acetate (536.6 mg, 1.33 mmol) was added 10% Pd/C (palladium on activated charcoal, 141.5 mg, 1.33 mmol). The above reaction mixture was stirred overnight under a hydrogen atmosphere. The filtrate filtered through celite was concentrated under reduced pressure to obtain 2-(4-(4-amino-3-methoxyphenyl)-[1,4'-bipiperidin]-1'-yl)ethyl acetate (399.9 mg, brown gum) in a yield of 80% without a separate purification process.

LC-MS calcd C$_{21}$H$_{33}$N$_3$O$_3$ 375.3, found 376.2 (M+H$^+$)

Step 4: Preparation of N-(2-((5-chloro-2-((4-(1'-(2-hydroxyethyl)-[1,4'-bipiperidin]-4-yl)-2-methoxyphenyl)amino)pyrimidin-4-yl)amino)phenyl)methanesulfonamide The same manner as in Step 2 of Example 1 above was performed to obtain N-(2-((5-chloro-2-((4-(1'-(2-hydroxyethyl)-[1,4'-bipiperidin]-4-yl)-2-methoxyphenyl)amino)pyrimidin-4-yl)amino)phenyl)methanesulfonamide (3.4 mg, 4%).

$^1$H NMR (300 MHz, CD$_3$OD) δ 8.13 (s, 1H), 7.38 (d, J=7.8 Hz, 1H), 7.53 (dd, J=7.8, 1.7 Hz, 1H), 7.47 (d, J=8.2 Hz, 1H), 7.43-7.32 (m, 2H), 6.94 (s, 1H), 6.70 (d, J=8.4 Hz, 1H), 3.93-3.84 (m, 7H), 3.72 (d, J=11.7 Hz, 2H), 3.62-3.54 (m, 1H), 3.24-3.13 (m, 4H), 2.94-2.86 (m, 4H), 2.48 (d, J=13.0 Hz, 2H), 2.22-2.06 (m, 7H); LC-MS calcd C$_{30}$H$_{40}$ClN$_7$O$_4$S 629.3, found 630.0 (M+H$^+$)

The compound of Example 15 was prepared according to Reaction Example 14 below.

[Reaction Example 14]

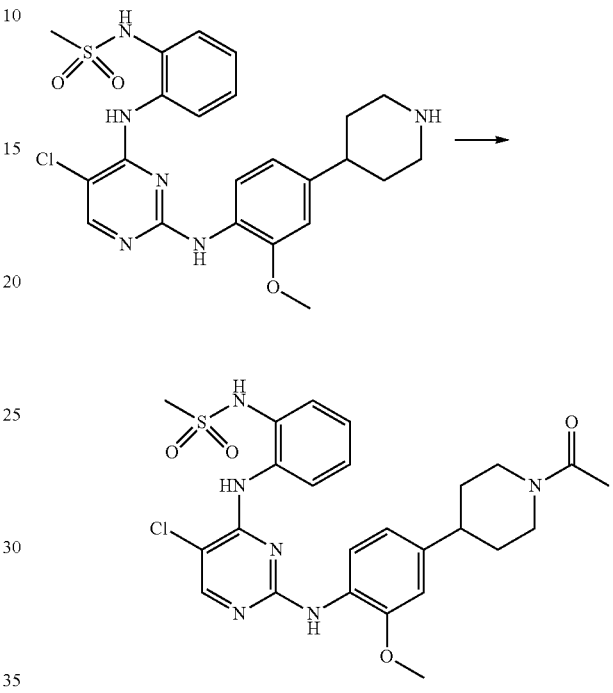

\<Example 15\> Preparation of N-(2-((2-((4-(1-acetylpiperidin-4-yl)-2-methoxyphenyl)amino)-5-chloropyrimidin-4-yl)amino)phenyl)methanesulfonamide To a dichloromethane (2 mL) solution of N-(2-((5-chloro-2-((2-methoxy-4-(piperidin-4-yl)phenyl)amino)pyrimidin-4-yl)amino)phenyl) methanesulfonamide (40 mg, 0.07 mmol) were added triethylamine (20 µL, 0.14 mmol) and acetic anhydride (10 µL, 0.07 mmol) at 0° C. The above reaction mixture was stirred for 2 hours at ambient temperature. The above mixture was concentrated under reduced pressure, and the residue was purified by prep-HPLC to obtain N-(2-((2-((4-(1-acetylpiperidin-4-yl)-2-methoxyphenyl)amino)-5-chloropyrimidin-4-yl)amino)phenyl)methanesulfonamide (12.7 mg, white solid) in a yield of 34%.

$^1$H NMR (300 MHz, CD$_3$OD) δ 8.09 (s, 1H), 7.76 (d, J=7.6 Hz, 1H), 7.51 (dd, J=7.7, 1.9 Hz, 1H), 7.43-7.32 (m, 3H), 6.94 (s, 1H), 6.70 (d, J=8.2 Hz, 1H), 4.68 (d, J=13.2 Hz, 1H), 4.05 (d, J=13.6 Hz, 1H), 3.86 (s, 3H), 3.24 (t, J=12.1 Hz 1H), 2.95 (s, 3 H), 2.87-2.66 (m, 2H), 2.15 (s, 3H), 1.88 (t, J=13.7 Hz, 2H), 1.76-1.51 (m, 2H); LC-MS calcd for C$_{25}$H$_{29}$ClN$_6$O$_4$S 544.2, found 545.0 (M+H$^+$)

The compounds of Examples 16 to 18 were prepared according to Reaction Example 15 below.

[Reaction Example 15]

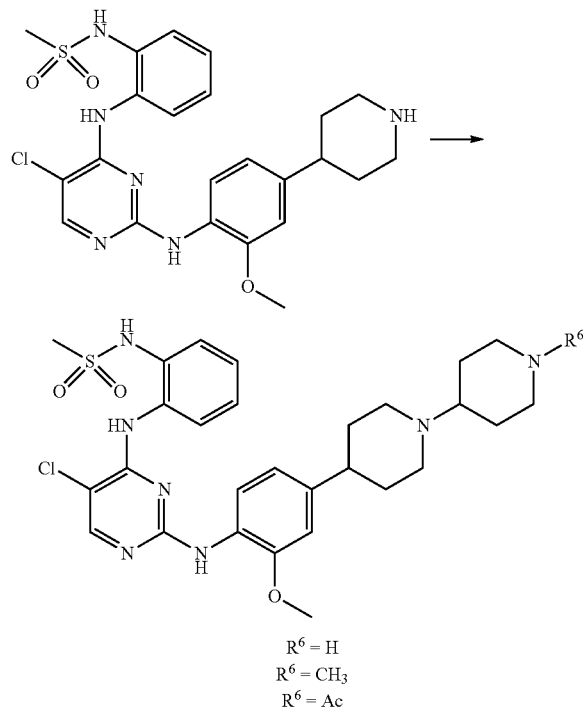

R⁶ = H
R⁶ = CH₃
R⁶ = Ac

In which, R⁶=H indicates the compound of Example 16, R⁶=CH₃ indicates the compound of Example 17, and R⁶=Ac indicates the compound of Example 18.

<Example 16> Preparation of N-(2-((2-((4-([1,4'-bipiperidin]-4-yl)-2-methoxyphenyl)amino)-5-chloropyrimidin-4-yl)amino)phenyl)methanesulfonamide N-(2-((5-chloro-2-((2-methoxy-4-(piperidin-4-yl)phenyl)amino)pyrimidin-4-yl)amino)phenyl)methanesulfonamide (24.4 mg, 0.04 mmol), 1-boc-4-piperidone (16.9 mg, 0.08 mmol), a dichloromethane 1 M solution (120 μL, 0.12 mmol) of acetic acid, and 1,2-dichloroethane (1 mL) of triethylamine (10 μL, 0.04 mmol) were stirred for 1 hour at ambient temperature, and then, sodium triacetoxyborohydride (12.7 mg, 0.06 mmol) was added. The above reaction mixture was stirred overnight at ambient temperature. The above mixture was concentrated under reduced pressure, CH₂Cl₂/trifluoroacetic acid (1:1, 1 mL) was added, and it was stirred for 2 hours at ambient temperature. The above reaction mixture was concentrated under vacuum, and the residue was purified by prep-HPLC to obtain N-(2-((2-((4-([1,4'-bipiperidin]-4-yl)-2-methoxyphenyl)amino)-5-chloropyrimidin-4-yl)amino) phenyl)methanesulfonamide (9.4 mg, red solid) in a yield of 51%.

¹H NMR (300 MHz, CD₃OD) δ 8.10 (s, 1H), 7.78-7.74 (m, 1H), 7.53-7.47 (m, 1H), 7.42-7.36 (m, 2H), 7.32 (d, J=8.1 Hz, 1H), 7.12 (sd, J=1.6 Hz, 1H), 6.99 (dd, J=8.2, 1.6 Hz, 1H), 4.39 (d, J=13.4 Hz, 1H), 3.98 (s, 3H), 3.89-3.78 (m, 1H), 3.74-3.58 (m, 1H), 3.52 (d, J=13.0 Hz, 2H), 3.21 (t, J=13.0 Hz, 2H), 3.10 (t, J=13.6 Hz, 1H), 3.03 (s, 3H), 2.23 (d, J=13.5 Hz, 2H), 2.08-1.97 (m, 4H), 1.84-1.71 (m, 2H); LC-MS calcd C₂₈H₃₆ClN₇O₃S 585.2, found 586.0 (M+H⁺)

<Example 17> Preparation of N-(2-((5-chloro-2-((2-methoxy-4-(1'-methyl-[1,4'-bipiperidin]-4-yl)phenyl)amino)pyrimidin-4-yl)amino)phenyl)methanesulfonamide The same manner as in Step 1 of Example 16 above was performed to obtain N-(2-((5-chloro-2-((2-methoxy-4-(1'-methyl-[1,4'-bipiperidin]-4-yl)phenyl)amino)pyrimidin-4-yl)amino)phenyl)methanesulfonamide (73.3 mg, 88%).

¹H NMR (300 MHz, CD₃OD) δ 8.13 (s, 1H), 7.72 (dd, J=7.8, 1.7 Hz, 1H), 7.52 (dd, J=7.8, 1.7 Hz, 1H), 7.45 (d, J=8.2 Hz, 1H), 7.40 (td, J=7.6, 1.8 Hz, 1H), 7.34 (td, J=7.7, 1.7 Hz, 1H), 6.94 (sd, J=1.8 Hz, 1H), 6.69 (d, J=8.2 Hz, 1H), 3.87 (s, 3H), 3.72 (d, J=11.9 Hz, 4H), 3.66-3.53 (m, 1H), 3.27-3.09 (m, 4H), 2.94 (s, 3H), 2.92 (s, 3H), 2.91-2.84 (m, 1H), 2.47 (d, J=13.4 Hz, 2H), 2.24-2.06 (m, 6H); LC-MS calcd C₂₉H₃₈ClN₇O₃S 599.2, found 600.0 (M+H⁺)

<Example 18> Preparation of N-(2-((2-((4-(1'-acetyl-[1,4'-bipiperidin]-4-yl)-2-methoxyphenyl)amino)-5-chloropyrimidin-4-yl)amino)phenyl)methanesulfonamide The same manner as in Step 1 of Example 16 above was performed to obtain N-(2-((2-((4-(1'-acetyl-[1,4'-bipiperidin]-4-yl)-2-methoxyphenyl)amino)-5-chloropyrimidin-4-yl)amino)phenyl)methanesulfonamide (40.2 mg, 46%).

¹H NMR (300 MHz, CD₃OD) δ 8.11 (s, 1H), 7.75 (dd, J=7.2, 2.3 Hz, 1H), 7.55-7.50 (m, 2H), 7.41-7.32 (m, 2H), 6.91 (s, 1H), 6.68 (d, J=9.5 Hz, 1H), 4.74 (d, J=13.6 Hz, 1H), 4.13 (d, J=13.9 Hz, 1H), 3.87 (s, 3H), 3.67 (d, J=12.1 Hz, 2H), 3.57-3.49 (m, 1H), 3.21 (t, J=12.9 Hz, 3H), 2.94 (s, 3H), 2.92-2.85 (m, 1H), 2.68 (t, J=12.7 Hz, 1H), 2.24-2.17 (m, 7H), 2.08-1.92 (m, 2H), 1.85-1.61 (m, 2H); LC-MS calcd C₃₀H₃₈ClN₇O₄S 627.2, found 628.0 (M+H⁺)

The compounds of Examples 19 to 22 were prepared according to Reaction Example 16 below.

[Reaction Example 16]

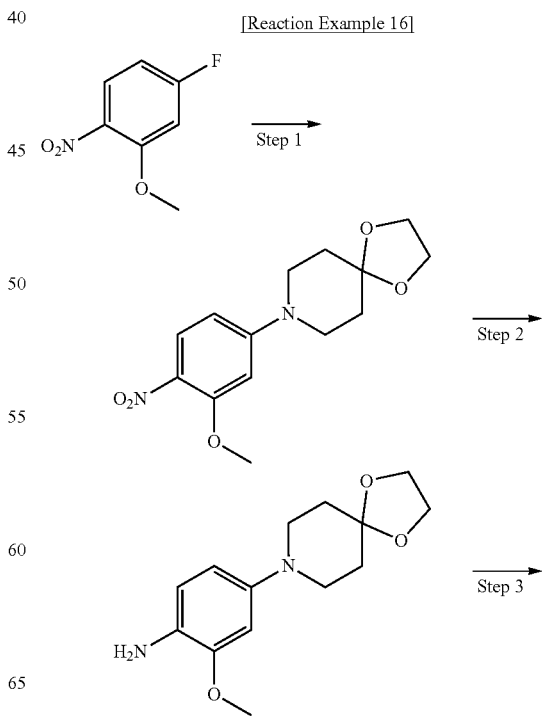

-continued

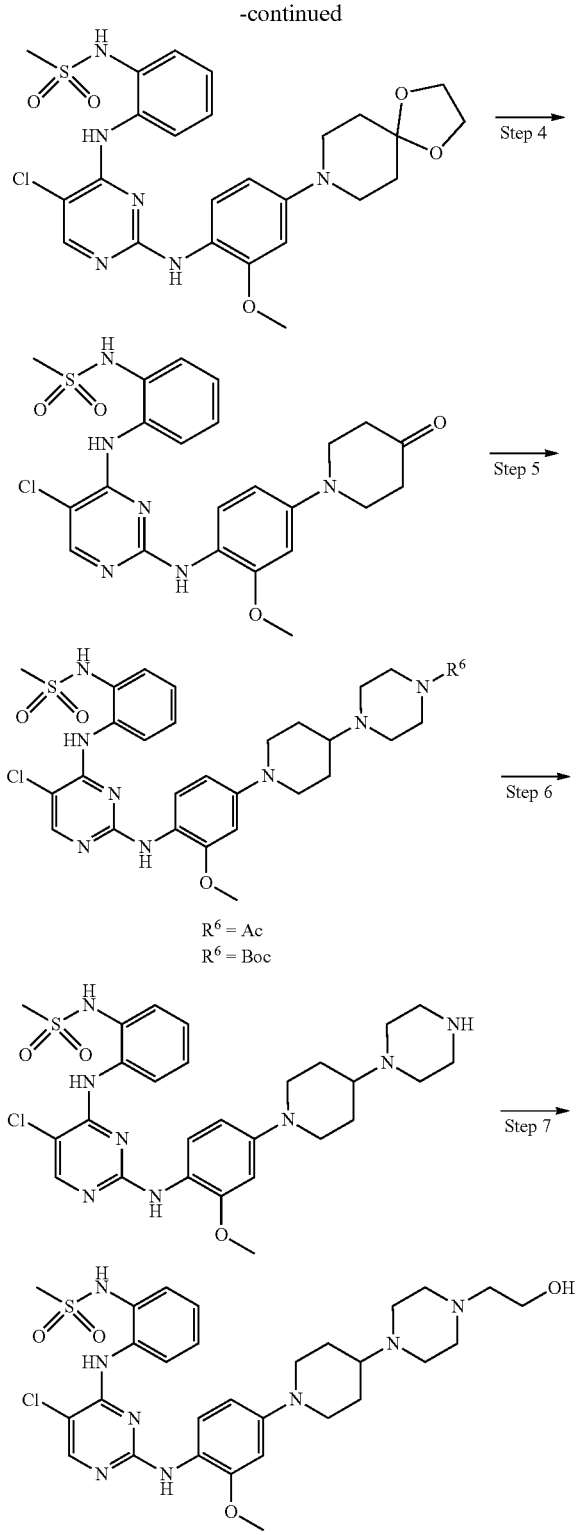

In which, in the compound produced after the performance of Step 5, $R^6$=Ac indicates the compound of Example 19, and $R^6$=Boc indicates the compound of Example 20, and the compound produced after the performance of Step 6 is the compound of Example 21, and the compound produced after the performance of Step 7 is the compound of Example 22.

<Example 19> Preparation of N-(2-((2-((4-(4-(4-acetylpiperazin-1-yl)piperidin-1-yl)-2-methoxyphenyl)amino)-5-chloro pyrimidin-4-yl)amino)phenyl) methanesulfonamide Step 1: Preparation of 8-(3-methoxy-4-nitrophenyl)-1,4-dioxa-8-azaspiro[4.5]decane While DMF (75 mL) of 4-fluoro-2-methoxy-1-nitrobenzene (5 g, 29.21 mmol) was stirred at ambient temperature, 1,4-dioxa-8-azaspiro[4.5]decane (5.0 g, 35.0 mmol) and potassium carbonate (8.0 g, 58.0 mmol) were added. The above reaction mixture was stirred overnight at ambient temperature. The above reaction mixture was quenched with cold water and stirred for 15 minutes. The precipitated solid was filtered and dried to obtain 8-(3-methoxy-4-nitrophenyl)-1,4-dioxa-8-azaspiro[4.5]decane (8.0 g, 94%) as a yellow solid.

$^1$H NMR (300 MHz, CDCl$_3$) δ 8.01 (d, J=9.3 Hz, 1H), 6.45 (dd, J=9.4, 2.6 Hz, 1H), 6.35 (d, J=2.5 Hz, 1H), 4.02 (s, 4H), 3.96 (s, 3H), 3.72-3.46 (m, 4H), 2.24-1.72 (m, 4H).

Step 2: Preparation of 2-methoxy-4-(1,4-dioxa-8-azaspiro[4.5]decan-8-yl)aniline

To a methanol (15 mL) stirred solution of 8-(3-methoxy-4-nitrophenyl)-1,4-dioxa-8-azaspiro[4.5]decane (1.0 g, 3.39 mmol) was added 10% Pd/C (palladium on activated charcoal, 36 mg, 0.33 mmol) under an argon atmosphere. The above reaction mixture was stirred for 3 hours at ambient temperature under a hydrogen gas pressure of 1 atm. The above reaction mixture was filtered through celite and concentrated under reduced pressure to obtain 2-methoxy-4-(1,4-dioxa-8-azaspiro[4.5]decan-8-yl)aniline (800 mg, 90%) as a brown solid.

$^1$H NMR (300 MHz, CDCl$_3$) δ 6.67-6.50 (m, 3H), 4.02 (s, 4H), 3.87 (br s, 3H), 3.22 (br s, 4H), 1.95 (br s, 4H)

Step 3: Preparation of N-(2-((5-chloro-2-((2-methoxy-4-(1,4-dioxa-8-azaspiro[4.5]decan-8-yl)phenyl)amino)pyrimidin-4-yl)amino)phenyl)methanesulfonamide To a n-butanol (5 mL) mixture of N-(2-((2,5-dichloropyrimidin-4-yl)amino)phenyl)methanesulfonamide (200 mg, 0.60 mmol) and 2-methoxy-4-(1,4-dioxa-8-azaspiro[4.5]decan-8-yl)aniline (158 mg, 0.60 mmol) was added a n-butanol solution (3.75 mL, 0.30 mmol) of 0.08 N HCl or TFA (trifluoroacetic acid). The above reaction tube was sealed with a Teflon-lined cap, and the reaction mixture was stirred overnight at 95° C. The above mixture was concentrated under reduced pressure, and the residue was purified by prep-HPLC to obtain N-(2-((5-chloro-2-((2-methoxy-4-(1,4-dioxa-8-azaspiro[4.5]decan-8-yl)phenyl)amino)pyrimidin-4-yl)amino)phenyl)methanesulfonamide (150 mg, 40%) as a white solid.

Step 4: Preparation of N-(2-((5-chloro-2-((2-methoxy-4-(4-oxopiperidin-1-yl)phenyl)amino)pyrimidin-4-yl)amino)phenyl)methanesulfonamide While methanol (2 ml) of N-(2-((5-chloro-2-((2-methoxy-4-(1,4-dioxa-8-azaspiro[4.5]decan-8-yl)phenyl)amino)pyrimidin-4-yl)amino)phenyl)methanesulfonamide (150 mg, 0.267 mmol) was stirred, 6 N HCl (2 ml) was added at ambient temperature. The above reaction mixture was heated at 60° C. for 3 hours. The above reaction mixture was cooled at ambient temperature, and a volatile substance was removed under reduced pressure. The resulting unpurified product was diluted with water, basified (pH 8) with a 5 N NaOH aqueous solution, and then, extracted with dichloromethane. The above organic layer was separated, washed with water and brine, then, dried over $Na_2SO_4$, and evaporated under reduced pressure to obtain N-(2-((5-chloro-2-((2-methoxy-4-(4-oxopiperidin-1-yl)phenyl)amino)pyrimidin-4-yl)amino)phenyl)methanesulfonamide (100 mg, 72%) as a white solid.

$^1$H NMR (300 MHz, $CDCl_3$) δ 8.06 (s, 1H), 7.88-7.65 (m, 3H), 7.64-7.45 (m, 1H), 7.43-7.31 (m, 2H), 6.56 (d, J=2.6 Hz, 1H), 6.39 (dd, J=8.8, 2.5 Hz, 1H), 3.86 (s, 3H), 3.54 (t, J=6.2 Hz, 4H), 2.96 (s, 3H), 2.61 (t, J=6.0 Hz, 4H)

Step 5: Preparation of N-(2-((2-((4-(4-(4-acetylpiperazin-1-yl)piperidin-1-yl)-2-methoxyphenyl) amino)-5-chloropyrimidin-4-yl)amino)phenyl)methanesulfonamide After N-(2-((2-((4-(4-(4-acetylpiperazin-1-yl)piperidin-1-yl)-2-methoxyphenyl)amino)-5-chloropyrimidin-4-yl) amino)phenyl)methanesulfonamide (60 mg, 0.11 mmol), 1-acetylpiperazine (28 mg, 0.17 mmol), 1 M solution (220 µL, 0.17 mmol) of dichloromethane of acetic acid, and 1,2-dichloroethane (1 mL) of triethylamine (50 µL, 0.34 mmol) were stirred for 1 hour at ambient temperature, sodium triacetoxyborohydride (49 mg, 0.23 mmol) was added. The above reaction mixture was stirred overnight at ambient temperature. The above mixture was concentrated under reduced pressure. The residue was purified by prep-HPLC to obtain N-(2-((2-((4-(4-(4-acetylpiperazin-1-yl)piperidin-1-yl)-2-methoxyphenyl)amino)-5-chloropyrimidin-4-yl)amino)phenyl)methanesulfonamide (35 mg, white solid) in a yield of 48%.

$^1$H NMR (500 MHz, $CDCl_3$) δ 8.10 (s, 1H), 7.79-7.75 (m, 1H), 7.72 (dd, J=7.2, 2.3 Hz, 1H), 7.56-7.52 (m, 2H), 7.38-7.32 (m, 3H), 6.51 (br s, 1H), 6.33 (d, J=8.9 Hz, 1H), 3.85 (s, 3H), 3.69-3.61 (m, 4H), 2.93 (s, 3H), 2.71 (t, J=11.7 Hz, 4H), 2.13 (br s, 3H), 2.03 (s, 4H), 1.80 (bs, 4H); LC-MS calcd for $C_{29}H_{37}ClN_8O_4S$ 628.23, found 627.0 (M–H$^+$)

<Example 20> Preparation of tert-butyl 4-(1-(4-((5-chloro-4-((2-(methylsulfonamido)phenyl)amino) pyrimidin-2-yl)amino)-3-methoxyphenyl)piperidin-4-yl)piperazine-1-carboxylate The same manner as in Step 5 of Example 19 above was performed to obtain tert-butyl 4-(1-chloro-4-((2-(methylsulfonamido)phenyl)amino)pyrimidin-2-yl)amino)-3-methoxyphenyl)piperidin-4-yl)piperazine-1-carboxylate (52 mg, 63%).

$^1$H NMR (300 MHz, $CDCl_3$) δ 8.09 (s, 1H), 7.76 (d, J=9.0 Hz, 1H), 7.72-7.66 (m, 1H), 7.57-7.52 (m, 1H), 7.48 (s, 1H), 7.38-7.31 (m, 2H), 7.26 (s, 1H), 6.50 (br s, 1H), 6.33 (d, J=8.4 Hz, 1H), 3.84 (s, 3H), 3.69-3.54 (m, 6H), 2.92 (s, 3H), 2.77-2.62 (m, 6H), 2.07-1.99 (m, 3H), 1.83-1.74 (m, 2H), 1.49 (s, 9H); LC-MS calcd for $C_{32}H_{43}ClN_8O_5S$ 686.28, found 685.0 (M–H$^+$)

<Example 21> Preparation of N-(2-((5-chloro-2-((2-methoxy-4-(4-(piperazin-1-yl)piperidin-1-yl) phenyl)amino)pyrimidin-4-yl)amino)phenyl)methanesulfonamide To a dichloromethane (1 ml) mixture of tert-butyl 4-(1-chloro-4-((2-(methylsulfonamido)phenyl)amino)pyrimidin-2-yl)amino)-3-methoxyphenyl)piperidin-4-yl)piperazine-1-carboxylate (20 mg, 0.03 mmol) was added dioxane (0.014 ml, 0.06 mmol) of 4 N HCl at 0° C. The above reaction mixture was elevated to ambient temperature and stirred for 2 hours. The above reaction mixture was concentrated under reduced pressure to obtain N-(2-((5-chloro-2-((2-methoxy-4-(4-(piperazin-1-yl)piperidin-1-yl)phenyl)amino)pyrimidin-4-yl)amino)phenyl)methanesulfonamide (20 mg, white solid) in a yield of 88%.

$^1$H NMR (300 MHz, $CD_3OD$) δ 8.19 (s, 1H), 7.70 (d, J=7.9 Hz, 1H), 7.60-7.56 (m, 1H), 7.52-7.44 (m, 2H), 7.45-7.40 (m, 1H), 7.16 (br s, 1H), 6.85 (br s, 1H), 3.94-3.88 (m, 5H), 3.70-3.66 (m, 8H), 3.50-3.38 (m, 2H), 3.00 (s, 3H), 2.51-2.40 (m, 2H), 2.34-2.18 (m, 2H); LC-MS calcd for $C_{27}H_{35}ClN_8O_3S$ 586.22, found 585.1 (M–H$^+$)

<Example 22> Preparation of N-(2-((5-chloro-2-((4-(4-(4-(2-hydroxyethyl)piperazin-1-yl)piperidin-1-yl)-2-methoxyphenyl)amino)pyrimidin-4-yl) amino)phenyl)methanesulfonamide While DMF (1 mL) of N-(2-((5-chloro-2-((2-methoxy-4-(4-(piperazin-1-yl)piperidin-1-yl)phenyl)amino)pyrimidin-4-yl)amino)phenyl)methanesulfonamide (30 mg, 0.05 mmol) was stirred, DIPEA (diisopropylethylamine) (0.017 mL, 0.1 mmol) and 2-iodoethanol (10.9 mg 0.06 mmol) were added at ambient temperature. The above reaction mixture was heated under 80° C. for 30 minutes at MW (microwave). The above reaction mixture was concentrated and purified by HPLC to obtain N-(2-((5-chloro-2-((4-(4-(4-(2-hydroxyethyl)piperazin-1-yl)piperidin-1-yl)-2-methoxyphenyl) amino)pyrimidin-4-yl)amino)phenyl) methanesulfonamide (20.1 mg, 70%) as a white solid.

$^1$NMR (300 MHz, $CD_3OD$) δ 8.11 (s, 1H), 7.76 (dd, J=7.4, 2.1 Hz, 1H), 7.58-7.53 (m, 1H), 7.49-7.37 (m, 3H), 6.91 (d, J=2.6 Hz, 1H), 6.66 (dd, J=8.8, 2.5 Hz, 1H), 3.92-3.80 (m, 7H), 3.50 (br s, 4H), 3.31-3.25 (m, 4H), 3.12-3.16 (m, 4H), 2.99 (s, 3H), 2.23 (d, J=12.4 Hz, 2H), 1.99-1.87 (m, 2H); LC-MS calcd for $C_{29}H_{39}ClN_8O_4S$ 630.25, found 629.1 (M–H$^+$)

The compounds of Examples 23 and 27 were prepared according to Reaction Example 17 below.

[Reaction Example 17]

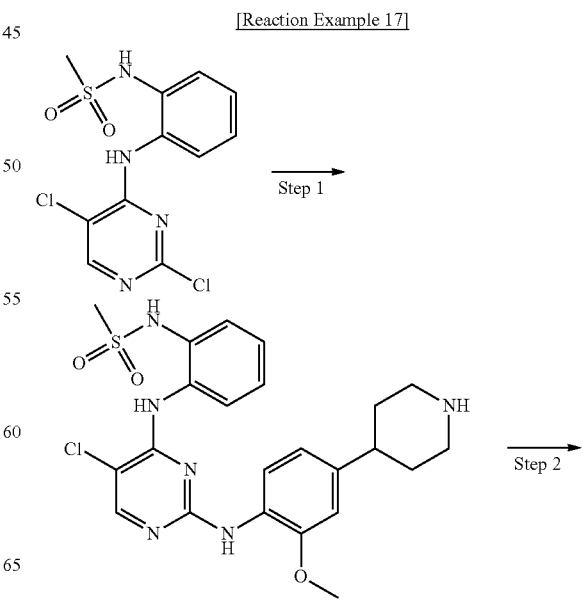

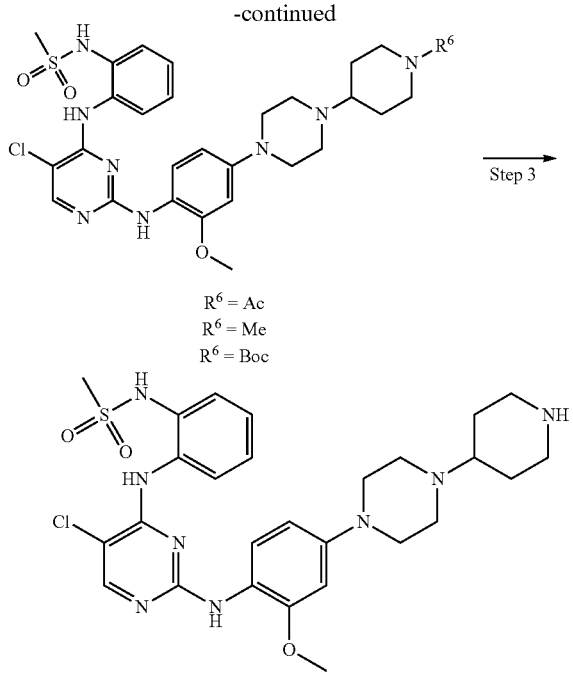

In which, the compound produced after the performance of Step 1 is the compound of Example 23, and in the compound produced after the performance of Step 2, $R^6$=Ac indicates the compound of Example 24, $R^6$=Me indicates the compound of Example 25, and $R^6$=Boc indicates the compound of Example 26, and the compound produced after the performance of Step 3 is the compound of Example 27.

<Example 23> Preparation of N-(2-((5-chloro-2-((2-methoxy-4-(piperazin-1-yl)phenyl)amino)pyrimidin-4-yl)amino)phenyl)methanesulfonamide To a n-butanol (1 mL) mixture of N-(2-((2,5-dichloropyrimidin-4-yl)amino)phenyl)methanesulfonamide 2 (100 mg, 0.30 mmol) and tert-butyl 4-(4-amino-3-methoxyphenyl)piperazine-1-carboxylate (92.2 mg, 0.30 mmol) was added a n-butanol solution (3.75 mL, 0.30 mmol) of 0.08 N HCl or TFA (trifluoroacetic acid). The above reaction tube was sealed with a Teflon-lined cap, and the reaction mixture was stirred overnight at 95° C. The above mixture was concentrated under reduced pressure, and the residue was purified by prep-HPLC to obtain N-(2-((5-chloro-2-((2-methoxy-4-(piperazin-1-yl)phenyl)amino)pyrimidin-4-yl)amino)phenyl) methanesulfonamide (150 mg, 82%) as a white solid.

$^1$H NMR (500 MHz, CD$_3$OD) δ 8.09 (s, 1H), 7.82-7.77 (m, 1H), 7.54 (dd, J=7.9, 1.7 Hz, 1H), 7.44-7.31 (m, 3H), 6.74 (d, J=2.5 Hz, 1H), 6.50 (s, 1H), 3.87 (s, 3H), 3.45 (m, 4H), 3.41 (m, 4H), 2.98 (s, 3H)

<Example 24> Preparation of N-(2-((2-((4-(4-(1-acetylpiperidin-4-yl)piperazin-1-yl)-2-methoxyphenyl)amino)-5-chloro pyrimidin-4-yl)amino)phenyl) methanesulfonamide The same manner as in Step 4 of Example 19 above was performed to obtain N-(2-((2-((4-(4-(1-acetylpiperidin-4-yl)piperazin-1-yl)-2-methoxy phenyl)amino)-5-chloropyrimidin-4-yl)amino)phenyl)methanesulfonamide (60 mg, 64%).

$^1$H NMR (300 MHz, CDCl$_3$) δ 8.09 (s, 1H), 7.79 (d, J=8.8 Hz, 1H), 7.75-7.68 (m, 1H), 7.60 (s, 1H), 7.57-7.50 (m, 1H), 7.37-7.31 (m, 2H), 6.49 (d, J=2.5 Hz, 1H), 6.31 (d, J=8.8 Hz, 1H), 3.84 (s, 3H), 3.29-3.18 (br s, 4H), 3.16-3.40 (m, 2H), 2.94 (s, 3H), 2.90-2.81 (br s, 4H), 2.66-2.52 (m, 2H), 2.13 (s, 3H), 1.99-1.95 (m, 2H), 1.59-1.47 (s, 2H); LC-MS calcd for C$_{29}$H$_{37}$ClN$_8$O$_4$S 628.23, found 627.0 (M–H$^+$)

<Example 25> Preparation of N-(2-((5-chloro-2-((2-methoxy-4-(4-(1-methylpiperidin-4-yl)piperazin-1-yl)phenyl)amino)pyrimidin-4-yl)amino)phenyl) methanesulfonamide The same manner as in Step 4 of Example 19 above was performed to obtain N-(2-((5-chloro-2-((2-methoxy-4-(4-(1-methylpiperidin-4-yl)piperazin-1-yl)phenyl)amino)pyrimidin-4-yl)amino)phenyl)methanesulfonamide (29.6 mg, 33%).

$^1$H NMR (500 MHz, CD$_3$OD) δ 8.08 (s, 1H), 7.80 (d, J=7.8 Hz, 1H), 7.53 (dd, J=7.7, 1.8 Hz, 1H), 7.40-7.33 (m, 3H), 6.73 (d, J=2.5 Hz, 1H), 6.50 (d, J=8.7 Hz, 1H), 3.87 (s, 3H), 3.75 (d, J=12.8 Hz, 2H), 3.62-3.45 (m, 8H), 3.20-3.12 (m, 2H), 2.98 (s, 3H), 2.95 (s, 3H), 2.56-2.47 (d, J=13.4 Hz, 2H), 2.20-2.10 (m, 2H); LC-MS calcd for C$_{28}$H$_{37}$ClN$_8$O$_3$S 600.24, found 599.0 (M–H$^+$)

<Example 26> Preparation of tert-butyl 4-(4-(4-((5-chloro-4-((2-(methylsulfonamido)phenyl)amino)pyrimidin-2-yl)amino)-3-methoxyphenyl)piperazin-1-yl)piperidine-1-carboxylate The same manner as in Step 4 of Example 19 above was performed to obtain tert-butyl 4-(4-(4-((5-chloro-4-((2-(methylsulfonamido)phenyl)amino)pyrimidin-2-yl)amino)-3-methoxyphenyl)piperazin-1-yl)piperidine-1-carboxylate (16.0 mg, 17%).

$^1$H NMR (300 MHz, CDCl$_3$) δ 8.09 (s, 1H), 7.79 (d, J=8.8 Hz, 1H), 7.74-7.68 (m, 1H), 7.56-7.51 (m, 2H), 7.38-7.31 (m, 2H), 6.49 (d, J=2.5 Hz, 1H), 6.32 (d, J=9.2 Hz, 1H), 4.23 (br s, 2H), 3.84 (s, 3H), 3.29 (br s, 4H), 2.94 (br s, 7H), 2.83-2.67 (m, 4H), 2.08-2.98 (m, 2H), 1.49 (s, 9H); LC-MS calcd for C$_{32}$H$_{43}$ClN$_8$O$_5$S 686.28, found 684.9 (M–H$^+$)

<Example 27> Preparation of N-(2-((5-chloro-2-((2-meth oxy-4-(4-(piperidin-4-yl)piperazin-1-yl)phenyl)amino)pyrimidin-4-yl)amino)phenyl)methanesulfonamide The same manner as in Example 21 above was performed to obtain N-(2-((5-chloro-2-((2-methoxy-4-(4-(piperidin-4-yl)piperazin-1-yl)phenyl)amino)pyrimidin-4-yl)amino)phenyl)methanesulfonamide (16 mg, 95%).

$^1$NMR (300 MHz, CD$_3$OD) δ 8.09 (s, 1H), 7.75 (br s, 1H), 7.55 (br s, J=7.9, 1.6 Hz, 1H), 7.48-7.35 (m, 2H), 7.29 (d, J=8.8 Hz, 1H), 6.77 (s, 1H), 6.54 (br s, 1H), 4.04-3.90 (m, 2H), 3.88 (s, 3H), 3.84-3.69 (m, 4H), 3.66-3.58 (m, 2H), 3.44-3.34 (m, 2H), 3.27-3.11 (m, 3H), 3.00 (s, 3H), 2.55 (d, J=13.3 Hz, 2H), 2.29-2.00 (m, 2H); LC-MS calcd for C$_{27}$H$_{35}$ClN$_8$O$_3$S 586.22, found 585.0 (M–H$^+$)

The compound of Example 28 was prepared according to Reaction Example 18 below.

[Reaction Example 18]

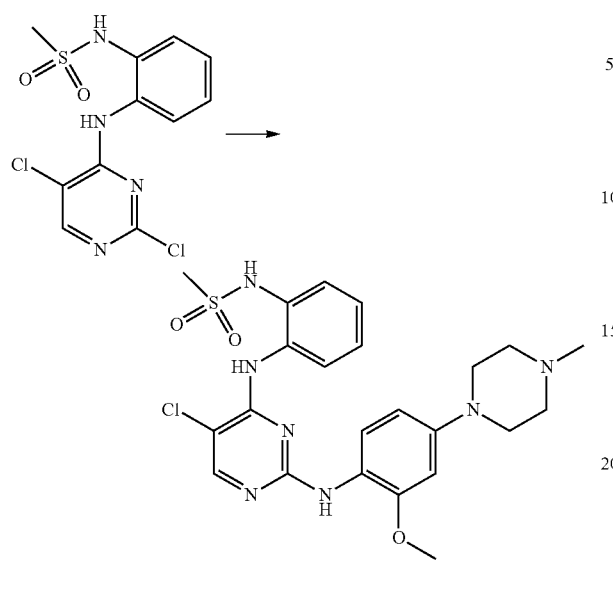

<Example 28> Preparation of N-(2-((5-chloro-2-((2-methoxy-4-(4-methylpiperazin-1-yl)phenyl)amino)pyrimidin-4-yl) amino)phenyl)methanesulfonamide The same manner as in Step 2 of Example 1 above was performed to obtain N-(2-((5-chloro-2-((2-methoxy-4-(4-methylpiperazin-1-yl)phenyl)amino)pyrimidin-4-yl)amino)phenyl)methanesulfonamide (15.0 mg, 19%).

$^1$H NMR (300 MHz, CDCl$_3$) δ 8.09 (s, 1H), 7.78 (d, J=8.8 Hz, 1H), 7.74-7.68 (m, 1H), 7.59-7.51 (m, 2H), 7.38-7.32 (m, 2H), 6.48 (d, J=2.5 Hz, 1H), 6.35-6.28 (m, 1H), 3.85 (s, 3H), 3.34-3.26 (m, 4H), 3.02-2.86 (m, 7H), 2.59 (s, 3H); LC-MS calcd for C$_{23}$H$_{28}$ClN$_7$O$_3$S 517.17, found 515.9 (M−H$^+$)

The compound of Example 29 was prepared according to Reaction Example 19 below.

[Reaction Example 19]

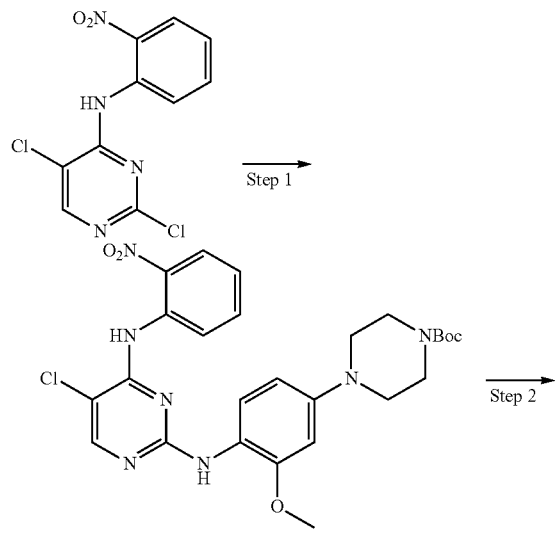

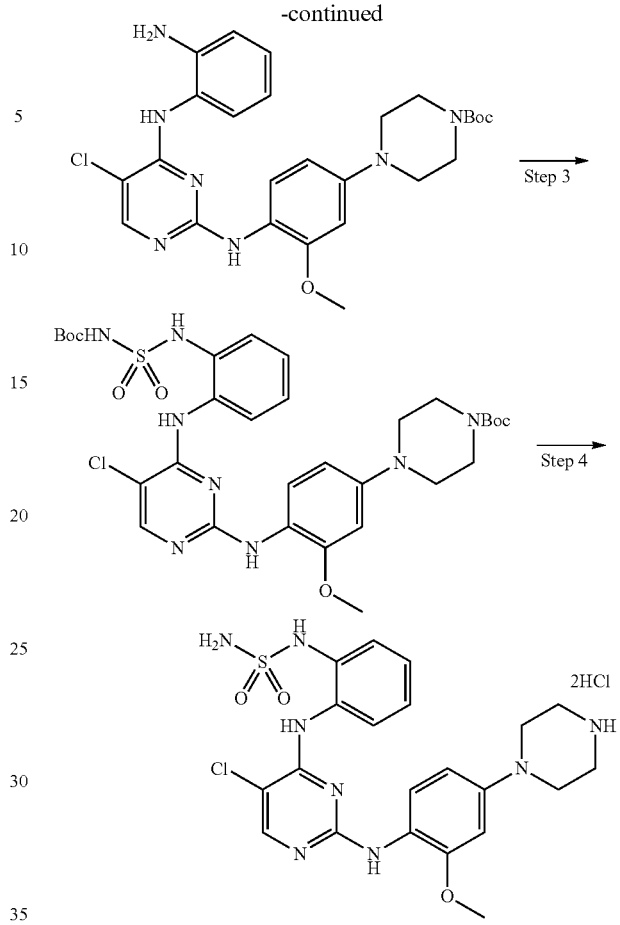

<Example 29> Preparation of 4-(4-((5-chloro-4-((2-(sulfamoylamino)phenyl)amino)pyrimidin-2-yl) amino)-3-methoxyphenyl)piperazine Step 1: Preparation of tert-butyl 4-(4-((5-chloro-4-((2-nitrophenyl)amino)pyrimidin-2-yl)amino)-3-methoxyphenyl)piperazine-1-carboxylate The same manner as in Step 1 of Example 6 above was performed to obtain tert-butyl 4-(4-((5-chloro-4-((2-nitrophenyl)amino)pyrimidin-2-yl)amino)-3-methoxyphenyl)piperazine-1-carboxylate (1.35 g, 69%).

$^1$H NMR (300 MHz, CDCl$_3$) δ 10.61 (s, 1H), 8.95 (dd, J=8.7, 1.3 Hz, 1H), 8.26 (dd, J=8.5, 1.6 Hz, 1H), 8.19 (s, 1H), 8.02 (d, J=8.7 Hz, 1H), 7.60 (td, J=8.6, 7.9, 1.6 Hz, 1H), 7.30 (s, 1H), 7.16 (ddd, J=8.5, 7.2, 1.3 Hz, 1H), 6.56 (d, J=2.5 Hz, 1H), 6.50 (dd, J=8.7, 2.5 Hz, 1H), 3.89 (s, 3H), 3.71-3.50 (m, 4H), 3.12-3.08 (m, 4H), 1.49 (s, 9H); LC-MS calcd for C$_{26}$H$_{30}$ClN$_7$O$_5$ 555.2, found 555.9 (M+H$^+$)

Step 2: Preparation of tert-butyl 4-(4-((4-((2-aminophenyl)amino)-5-chloropyrimidin-2-yl)amino)-3-methoxyphenyl)piperazine-1-carboxylate The same manner as in Step 2 of Example 6 above was performed to obtain tert-butyl 4-(4-((4-((2-aminophenyl)amino)-5-chloropyrimidin-2-yl)amino)-3-methoxyphenyl)piperazine-1-carboxylate (900 mg, 70%).

LC-MS calcd for $C_{26}H_{32}BrN_7O_3$ 525.2, found 526.0 (M+H$^+$)

Step 3: Preparation of tert-butyl 4-(4-((4-((2-4N-(tert-butoxy carbonyl)sulfamoyl)amino)phenyl)amino)-5-chloropyrimidin-2-yl)amino)-3-methoxy phenyl)piperazine-1-carboxylate The same manner as in Step 3 of Example 6 above was performed to obtain tert-butyl 4-(4-((5-chloro-4-((2-4N-(tert-butoxy carbonyl)sulfamoyl)amino)phenyl)amino)pyrimidin-2-yl)amino)-3-methoxyphenyl)piperazine-1-carboxylate (13.5 mg, 39%).

$^1$H NMR (500 MHz, CDCl$_3$) δ 8.03-7.90 (m, 3H), 7.87 (d, J=8.7 Hz, 1H), 7.46-7.28 (m, 3H), 7.20 (t, J=7.6 Hz, 1H), 6.50 (s, 1H), 6.34 (d, J=8.8 Hz, 1H), 3.82 (s, 3H), 3.58 (t, J=5.0 Hz, 4H), 3.04 (t, J=5.0 Hz, 4H), 1.48 (s, 18H)

Step 4: Preparation of 4-(4-((5-chloro-4-((2-(sulfamoylamino)phenyl)amino)pyrimidin-2-yl)amino)-3-methoxyphenyl)piperazine The same manner as in Step 4 of Example 6 above was performed to obtain 4-(4-((5-chloro-4-((2-(sulfamoylamino)phenyl)amino)pyrimidin-2-yl)amino)-3-methoxy phenyl)piperazine (3.6 mg, quantitative yield).

$^1$H NMR (300 MHz, CD$_3$OD) δ 8.05 (s, 1H), 7.93-7.81 (m, 1H), 7.50 (dd, J=7.7, 1.9 Hz, 1H), 7.43-7.24 (m, 3H), 6.73 (s, 1H), 6.53 (d, J=8.7 Hz, 1H), 3.85 (s, 3H), 3.43-3.40 (m, 8H); LC-MS calcd for $C_{21}H_{25}ClN_8O_3S$ 504.2, found 504.8 (M+H$^+$)

The compound of Example 30 was prepared according to Reaction Example 20 below.

[Reaction Example 20]

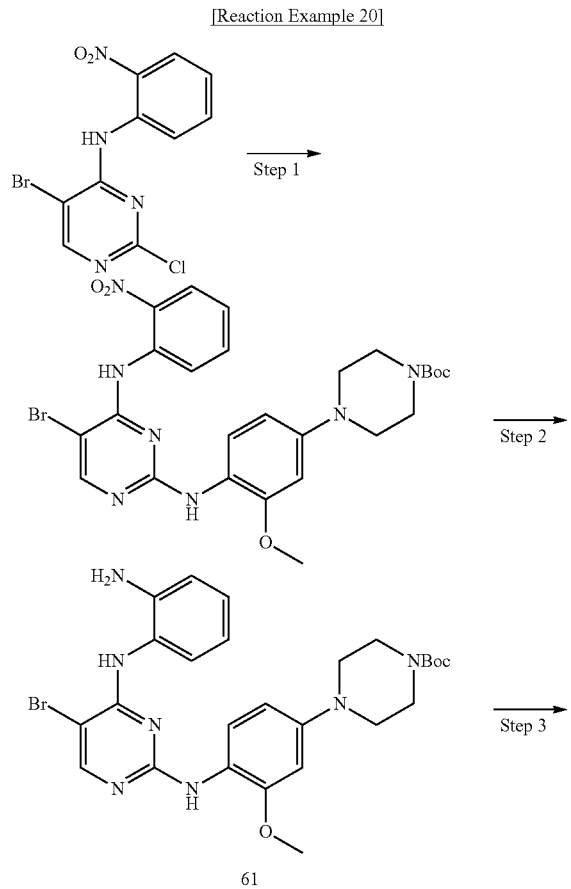

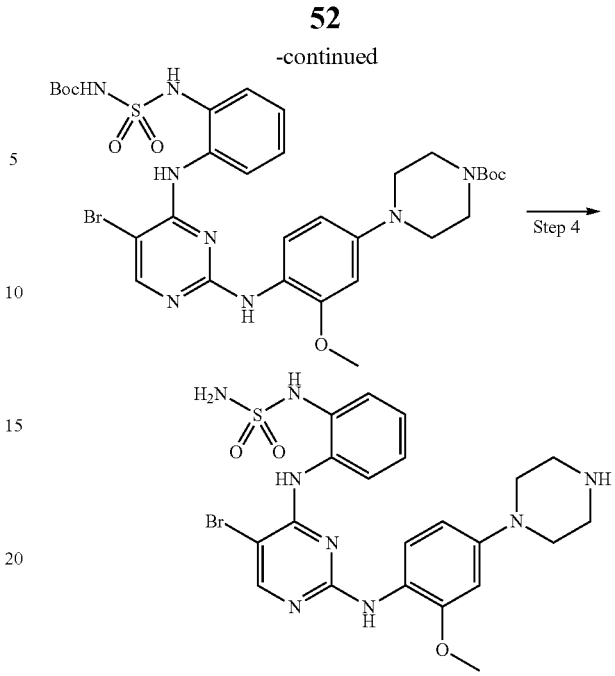

<Example 30> Preparation of 4-(4-((5-bromo-4-((2-(sulfamoylamino)phenyl)amino)pyrimidin-2-yl)amino)-3-methoxy phenyl)piperazine Step 1: Preparation of tert-butyl 4-(4-((5-bromo-4-((2-nitrophenyl)amino)pyrimidin-2-yl)amino)-3-methoxyphenyl)piperazine-1-carboxylate The same manner as in Step 1 of Example 6 above was performed to obtain tert-butyl 4-(4-((5-bromo-4-((2-nitrophenyl)amino)pyrimidin-2-yl)amino)-3-methoxyphenyl)piperazine-1-carboxylate (70 mg, 12%).

$^1$H NMR (300 MHz, CDCl$_3$) δ 10.58 (s, 1H), 8.86 (d, J=8.8 Hz, 1H), 8.30-8.25 (m, 2H), 8.04 (s, 1H), 7.60 (t, J=8.0 Hz, 1H), 7.19 (t, J=7.8 Hz, 1H), 6.61 (s, 1H), 3.90 (s, 3H), 3.69 (br s, 4H), 3.16 (br s, 4H), 1.52-1.44 (s, 9H); LC-MS calcd for $C_{26}H_{30}BrN_7O_5$ 599.2, found 600.7 (M+H$^+$)

Step 2: Preparation of tert-butyl 4-(4-((4-((2-aminophenyl)amino)-5-bromopyrimidin-2-yl)amino)-3-methoxyphenyl)piperazine-1-carboxylate The same manner as in Step 2 of Example 6 above was performed to obtain tert-butyl 4-(4-((4-((2-aminophenyl)amino)-5-bromopyrimidin-2-yl)amino)-3-methoxyphenyl)piperazine-1-carboxylate (50 mg, 74%).

LC-MS calcd for $C_{26}H_{33}BrN_7O_3$ 569.2, found 569.8 (M+H$^+$)

Step 3: Preparation of tert-butyl 4-(4-((5-bromo-4-((2-4N-(tert-butoxy carbonyl)sulfamoyl)amino)phenyl)amino)pyrimidin-2-yl)amino)-3-methoxy phenyl)piperazine-1-carboxylate The same manner as in Step 3 of Example 6 above was performed to obtain tert-butyl 4-(4-((5-bromo-4-((2-4N-(tert-butoxy carbonyl)sulfamoyl)amino)phenyl)amino)pyrimidin-2-yl)amino)-3-methoxyphenyl)piperazine-1-carboxylate (20 mg, 33%).

¹H NMR (300 MHz, CD₃OD) δ 8.07 (s, 1H), 7.94 (d, J=8.0 Hz, 1H), 7.82 (s, 1H), 7.66 (d, J=8.7 Hz, 1H), 7.38 (dd, J=7.7, 1.5 Hz, 1H), 7.31 (td, J=7.8, 1.7 Hz, 1H), 7.27-7.19 (m, 1H), 6.62 (s, 1H), 6.39 (s, 1H), 3.84 (s, 3H), 3.62-3.52 (m, 4H), 3.09 (br s, 4H), 1.49 (s, 9H), 1.48 (s, 9H); LC-MS calcd for $C_3H_{41}BrN_6O_7S$ 748.2, found 748.6 (M+H⁺)

Step 4: Preparation of 4-(4-((5-bromo-4-((2-(sulfamoylamino)phenyl)amino)pyrimidin-2-yl)amino)-3-methoxyphenyl)piperazine The same manner as in Step 4 of Example 6 above was performed to obtain 4-(4-((5-bromo-4-((2-(sulfamoylamino)phenyl)amino)pyrimidin-2-yl)amino)-3-methoxyphenyl)piperazine (16.9 mg, quantitative yield).

¹H NMR (500 MHz, CD₃OD) δ 8.13 (s, 1H), 7.90 (s, 1H), 7.50 (dd, J=7.7, 1.6 Hz, 1H), 7.41-7.25 (m, 3H), 6.74 (d, J=2.5 Hz, 1H), 6.55 (s, 1H), 3.85 (s, 3H), 3.45 (q, J=4.1, 3.6 Hz, 4H), 3.39 (dd, J=6.7, 3.3 Hz, 4H); LC-MS calcd for $C_{21}H_{25}BrN_8O_3S$ 548.1, found 548.7 (M+H⁺)

The compound of Example 31 was prepared according to Reaction Example 21 below.

¹H NMR (300 MHz, CDCl₃) δ 8.47 (s, 1H), 8.23 (br s, 1H), 7.92 (d, J=7.8 Hz, 1H), 7.46-7.28 (m, 3H), 6.27 (br s, 1H), 3.05 (s, 3H); LC-MS calcd for $C_{12}H_{10}ClF_3N_4O_2S$ 366.0, found 366.8 (M+H⁺)

Step 2: Preparation of N-(2-((2-((2-methoxy-4-(piperazin-4-yl)phenyl)amino)-5-(trifluoromethyl)pyrimidin-4-yl)amino)phenyl)methanesulfonamide The same manner as in Step 2 of Example 1 above was performed to obtain N-(2-((2-((2-methoxy-4-(piperazin-4-yl)phenyl)amino)-5-(trifluoromethyl)pyrimidin-4-yl)amino)phenyl)methanesulfonamide (54.2 mg, 65%).

¹H NMR (300 MHz, CD₃OD) δ 8.32 (br s, 1H), 7.68 (br s, 1H), 7.49 (dd, J=7.4, 2.1 Hz, 1H), 7.43-7.29 (m, 3H), 6.69 (br s, 1H), 6.39 (br s, 1H), 3.85 (s, 3H), 3.39 (br s, 8H), 2.93 (s, 3H); LC-MS calcd for $C_{23}H_{26}F_3N_7O_3S$ 537.2, found 537.8 (M+H⁺)

The compound of Example 32 was prepared according to Reaction Example 22 below.

[Reaction Example 21]

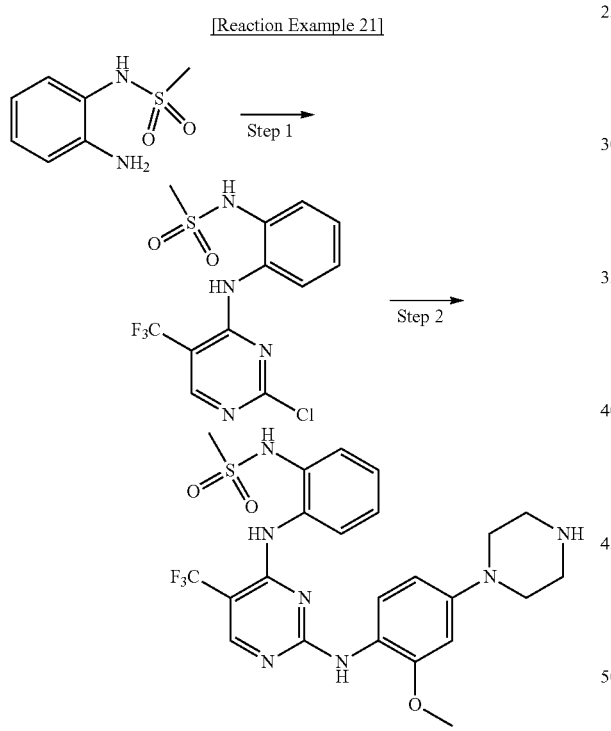

<Example 31> Preparation of N-(2-((2-((2-methoxy-4-(piperazin-4-yl)phenyl)amino)-5-(trifluoromethyl)pyrimidin-4-yl) amino)phenyl)methanesulfonamide Step 1: Preparation of N-(2-((2-chloro-5-(trifluoromethyl)pyrimidin-4-yl)amino)phenyl)methanesulfonamide The same manner as in Step 1 of Example 1 above was performed to obtain N-(2-((2-chloro-5-(trifluoromethyl)pyrimidin-4-yl)amino)phenyl)methanesulfonamide (199 mg, 18%).

[Reaction Example 22]

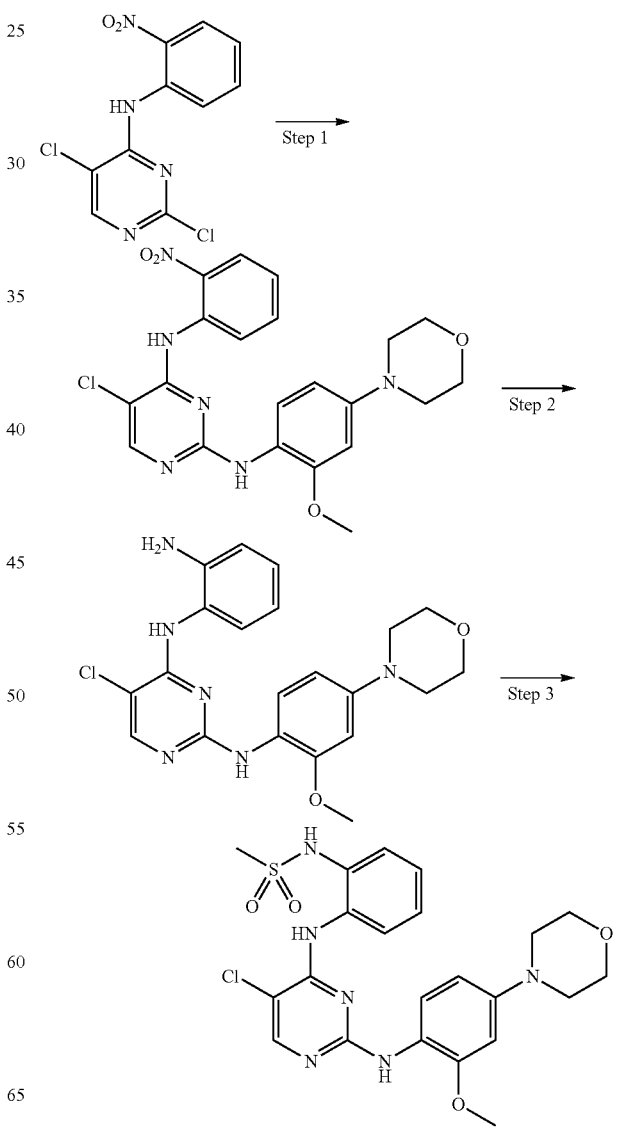

<Example 32> Preparation of N-(2-((5-chloro-2-((2-methoxy-4-morpholinophenyl)amino)pyrimidin-4-yl)amino)phenyl) methanesulfonamide

Step 1: Preparation of 5-chloro-$N^2$-(2-methoxy-4-morpholinophenyl)-$N^4$-(2-nitrophenyl)pyrimidin-2,4-diamine The same manner as in Step 1 of Example 6 above was performed to obtain 5-chloro-$N^2$-(2-methoxy-4-morpholinophenyl)-$N^4$-(2-nitrophenyl)pyrimidin-2,4-diamine (125.2 mg, 39%).

$^1$H NMR (300 MHz, CDCl$_3$) δ 11.08 (s, 1H), 10.31 (s, 1H), 8.52 (d, J=7.9 Hz, 1H), 8.28 (d, J=8.1 Hz, 1H), 8.10 (s, 1H), 7.69 (d, J=5.8 Hz, 1H), 7.57-7.47 (m, 1H), 7.33-7.30 (m, 1H), 7.11 (s, 1H), 6.86 (d, J=7.1 Hz, 1H), 4.12 (br s, 4H), 3.87 (s, 3H), 3.44 (br s, 4H).

LC-MS calcd for $C_{21}H_{22}ClN_6O_4$ 457.1, found 456.9 (M+H$^+$)

Step 2: Preparation of $N^4$-(2-aminophenyl)-5-chloro-$N^2$-(2-methoxy-4-morpholinophenyl)pyrimidin-2,4-di amine The same manner as in Step 2 of Example 6 above was performed to obtain $N^4$-(2-aminophenyl)-5-chloro-$N^2$-(2-methoxy-4-morpholinophenyl)pyrimidin-2,4-di amine (43.2 mg, 92%).

LC-MS calcd for $C_{21}H_{24}ClN_6O_2$ 427.2, found 426.9 (M+H$^+$)

Step 3: Preparation of N-(2-((5-chloro-2-((2-methoxy-4-morpholinophenyl)amino)pyrimidin-4-yl)amino)phenyl)methanesulfonamide To dichloromethane (2 mL) of $N^4$-(2-aminophenyl)-5-chloro-$N^2$-(2-methoxy-4-morpholinophenyl)pyrimidin-2,4-di amine (43.2 mg, 0.10 mmol) were added triethylamine (50 µL, 0.40 mmol) and methanesulfonyl chloride (30 µL, 0.30 mmol) at 0° C. The above reaction mixture was stirred overnight at ambient temperature. The above mixture was concentrated under reduced pressure, and the residue was purified by flash column chromatography (CH$_2$Cl$_2$/EtOAc, 5:1) to obtain N-(2-((5-chloro-2-((2-methoxy-4-morpholinophenyl)amino)pyrimidin-4-yl)amino)phenyl)methanesulfonamide (16.1 mg, pale yellow solid) in a yield of 32%.

$^1$H NMR (300 MHz, CDCl$_3$) δ 8.07 (s, 1H), 7.77 (d, J=8.8 Hz, 1H), 7.70-7.67 (m, 1H), 7.53-7.50 (m, 1H), 7.45 (br s, 1H), 7.34-7.30 (m, 2H), 7.27 (br s, 1H), 6.47 (sd, J=2.5 Hz, 1H), 6.30 (dd, J=8.9, 2.5 Hz, 1H), 3.88-3.85 (m, 4H), 3.83 (s, 3H), 3.10-3.07 (m, 4H), 2.90 (s, 3H); LC-MS calcd for $C_{22}H_{26}ClN_6O_4S$ 505.1, found 504.9 (M+H$^+$)

<Example 33> Preparation of N-(2-((5-chloro-2-((4-(4-((3R,5S)-3,5-dimethylpiperazin-1-yl)piperidin-1-yl)-2-methoxyphenyl)amino)pyrimidin-4-yl)amino)phenyl)methanesulfonamide The same manner as in Example 19 above was performed to obtain N-(2-((5-chloro-2-((4-(4-((3R,5S)-3,5-dimethylpiperazin-1-yl)piperidin-1-yl)-2-methoxyphenyl)amino)pyrimidin-4-yl)amino)phenyl)methanesulfonamide (10.7 mg, 18%).

$^1$H NMR (300 MHz, CD$_3$OD) δ 9.65 (s, 1H), 9.31 (dd, J=7.3, 2.1 Hz, 1H), 9.14-9.04 (m, 2H), 9.06-8.95 (m, 1H), 9.00-8.86 (m, 2H), 8.44 (sd, J=2.5 Hz, 1H), 8.20 (dd, J=8.9, 2.5 Hz, 1H), 5.54 (s, 3H), 5.41 (d, J=14.7 Hz, 2H), 5.22-5.02 (m, 3H), 4.82-4.60 (m, 3H), 4.52 (s, 3H), 4.32 (t, J=12.3 Hz, 2H), 3.76 (d, J=12.6 Hz, 2H), 3.62-3.40 (m, 2H), 2.95 (d, J=6.4 Hz, 6H); LC-MS (M+H$^+$) calcd for $C_{29}H_{40}ClN_8O_3S$ 615.3, found 615.1.

<Example 34> Preparation of N-(2-((5-chloro-2-((2-methoxy-4-(4-morpholinopiperidin-1-yl)phenyl)amino)pyrimidin-4-yl)amino)phenyl)methanesulfonamide The same manner as in Example 19 above was performed to obtain N-(2-((5-chloro-2-((2-methoxy-4-(4-morpholinopiperidin-1-yl)phenyl)amino)pyrimidin-4-yl)amino)phenyl)methanesulfonamide (15.3 mg, 27%).

$^1$H NMR (300 MHz, CD$_3$OD) δ 8.05 (s, 1H), 7.77 (d, J=7.7 Hz, 1H), 7.56-7.48 (m, 1H), 7.38 (qd, J=7.3, 1.8 Hz, 2H), 7.25 (d, J=8.7 Hz, 1H), 6.70 (sd, J=2.5 Hz, 1H), 6.50 (d, J=8.8 Hz, 1H), 4.10 (dd, J=19.2, 8.3 Hz, 2H), 3.92 (d, J=13.2 Hz, 2H), 3.84 (s, 3H), 3.81-3.68 (m, 2H), 3.65-3.48 (m, 2H), 3.48-3.34 (m, 1H), 3.29-3.15 (m, 2H), 2.97 (s, 3H), 2.93-2.79 (m, 2H), 2.28 (d, J=12.1 Hz, 2H), 1.87 (qd, J=12.3, 4.2 Hz, 2H); LC-MS (M+H$^+$) calcd for $C_{27}H_{35}ClN_7O_4S$ 588.2, found 588.0

<Example 35> Preparation of N-(2-((5-chloro-2-((2-methoxy-4-(4-(pyrrolidin-1-yl)piperidin-1-yl)phenyl)amino)pyrimidin-4-yl)amino)phenyl)methanesulfonamide The same manner as in Example 19 above was performed to obtain N-(2-((5-chloro-2-((2-methoxy-4-(4-(pyrrolidin-1-yl)piperidin-1-yl)phenyl)amino)pyrimidin-4-yl)amino)phenyl)methanesulfonamide (7.8 mg, 14%).

$^1$H NMR (300 MHz, CD$_3$OD) δ 8.05 (s, 1H), 7.77 (d, J=7.7 Hz, 1H), 7.56-7.48 (m, 1H), 7.38 (qd, J=7.3, 1.8 Hz, 2H), 7.25 (d, J=8.7 Hz, 1H), 6.70 (sd, J=2.5 Hz, 1H), 6.50 (d, J=8.8 Hz, 1H), 4.10 (dd, J=19.2, 8.3 Hz, 2H), 3.92 (d, J=13.2 Hz, 2H), 3.84 (s, 3H), 3.81-3.68 (m, 2H), 3.65-3.48 (m, 2H), 3.48-3.34 (m, 1H), 3.29-3.15 (m, 2H), 2.97 (s, 3H), 2.93-2.79 (m, 2H), 2.28 (d, J=12.1 Hz, 2H), 1.87 (qd, J=12.3, 4.2 Hz, 2H); LC-MS (M+H$^+$) calcd for $C_{27}H_{35}ClN_7O_3S$ 572.2, found 572.0

The compound of Example 36 was prepared according to Reaction Example 23 below.

[Reaction Example 23]

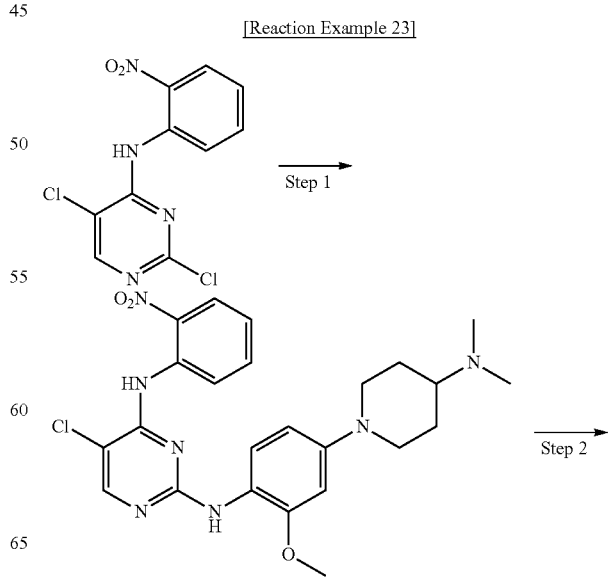

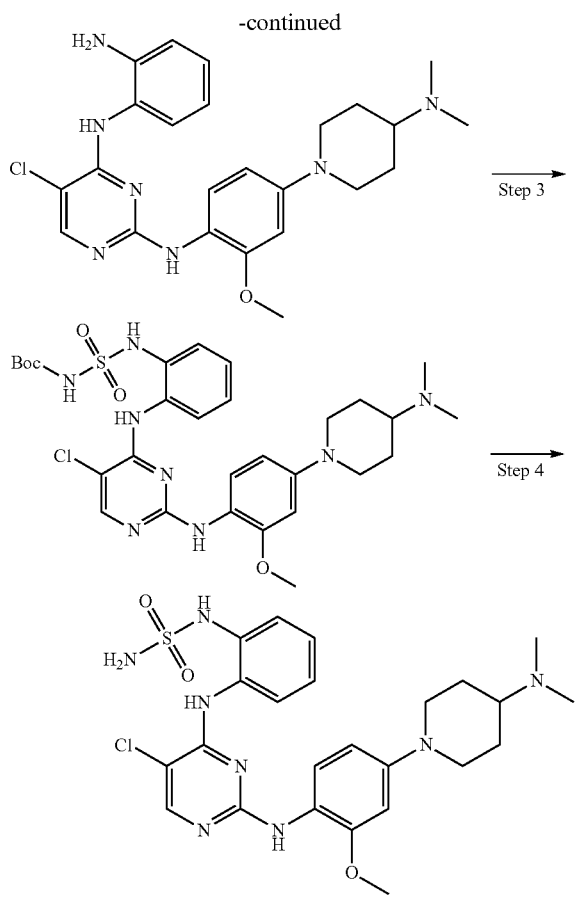

<Example 36> Preparation of (N-(2-((5-chloro-2-((4-(4-(dimethylamino)piperidin-1-yl)-2-methoxyphenyl)amino)pyrimidin-4-yl)amino)phenyl)sulfamoyl)carbamate Step 1: Preparation of 5-chloro-N2-(4-(4-(dimethylamino)piperidin-1-yl)-2-methoxyphenyl)-N4-(2-nitrophenyl)pyrimidin-2,4-diamine The same manner as in Step 1 of Example 6 above was performed to obtain 5-chloro-N2-(4-(4-(dimethylamino)piperidin-1-yl)-2-methoxyphenyl)-N4-(2-nitrophenyl)pyrimidin-2,4-diamine (120 mg, 45%).

¹H NMR (500 MHz, chloroform-d) 10.65 (s, 1H), 9.00 (dd, J=8.7, 1.3 Hz, 1H), 8.29 (dd, J=8.5, 1.6 Hz, 1H), 8.21 (s, 1H), 8.00 (d, J=8.7 Hz, 1H), 7.68-7.58 (m, 1H), 7.23-7.26 (m, 2H), 7.23-7.14 (m, 1H), 6.60 (d, J=2.5 Hz, 1H), 6.54 (dd, J=8.8, 2.6 Hz, 1H), 3.91 (s, 3H), 3.70 (d, J=11.8 Hz, 2H), 2.75 (td, J=12.2, 2.4 Hz, 2H), 2.41 (bs, 7H), 2.02 (d, J=12.4 Hz, 2H), 1.80-1.68 (m, 2H).

Step 2: Preparation of N4-(2-aminophenyl)-5-chloro-N2-(4-(4-(dimethylamino)piperidin-1-yl)-2-methoxyphenyl)pyrimidin-2,4-diamine The same manner as in Step 2 of Example 6 above was performed to obtain N4-(2-aminophenyl)-5-chloro-N2-(4-(4-(dimethylamino)piperidin-1-yl)-2-methoxyphenyl)pyrimidin-2,4-diamine (90 mg, 85%).

¹H NMR (500 MHz, chloroform-d) 8.04 (s, 1H), 7.95 (d, J=8.8 Hz, 1H), 7.38-7.36 (m, 2H), 7.19 (td, J=7.7, 1.5 Hz, 1H), 6.92-6.86 (m, 2H), 6.77 (s, 1H), 6.52 (d, J=2.6 Hz, 1H), 6.33-6.29 (m, 1H), 3.85 (s, 3H), 3.84-3.77 (m, 2H), 3.66-3.57 (m, 3H), 2.68 (td, J=12.2, 2.3 Hz, 3H), 2.47-2.38 (bs, 8H), 2.00 (dd, J=11.9, 3.2 Hz, 2H), 1.72-1.68 (m, 2H).

Step 3: Preparation of tert-butyl (N-(2-((5-chloro-2-((4-(4-(dimethylamino)piperidin-1-yl)-2-methoxy phenyl)amino)pyrimidin-4-yl)amino)phenyl)sulfamoyl)carbamate The same manner as in Step 3 of Example 6 above was performed to obtain tert-butyl (N-(2-((5-chloro-2-((4-(4-(dimethylamino)piperidin-1-yl)-2-methoxy phenyl)amino)pyrimidin-4-yl)amino)phenyl)sulfamoyl)carbamate (62 mg, 48%).

¹H NMR (500 MHz, DMSO-d₆) 8.06 (s, 1H), 7.9-7.88 (m, 1H), 7.78 (s, 1H), 7.55 (d, J=8.8 Hz, 1H), 7.27-7.21 (m, 1H), 7.12-7.04 (m, 2H), 6.61 (d, J=2.5 Hz, 1H), 6.38 (dd, J=8.9, 2.5 Hz, 1H), 3.78 (s, 3H), 3.72 (d, J=12.2 Hz, 2H), 2.66-2.54 (m, 9H), 1.92 (d, J=12.4 Hz, 2H), 1.65-1.54 (m, 2H), 1.36 (s, 9H).

Step 4: Preparation of (N-(2-((5-chloro-2-((4-(4-(dimethylamino)piperidin-1-yl)-2-methoxy phenyl)amino)pyrimidin-4-yl)amino)phenyl)sulfamoyl)carbamate The same manner as in Step 4 of Example 6 above was performed to obtain (N-(2-((5-chloro-2-((4-(4-(dimethylamino)piperidin-1-yl)-2-methoxy phenyl)amino)pyrimidin-4-yl)amino)phenyl)sulfamoyl)carbamate (30 mg, 60%).

¹H NMR (300 MHz, Methanol-d₄) 8.04 (dd, J=8.0, 1.7 Hz, 1H), 8.00 (s, 1H), 7.74 (d, J=8.8 Hz, 1H), 7.47 (dd, J=7.7, 1.8 Hz, 1H), 7.33-7.21 (m, 2H), 6.66 (d, J=2.6 Hz, 1H), 6.44 (dd, J=8.8, 2.5 Hz, 1H), 3.86 (s, 3H), 3.69 (d, J=12.1 Hz, 2H), 2.75-2.65 (m, 2H), 2.36 (bs, 7H), 2.02 (d, J=12.3 Hz, 2H), 1.66 (dd, J=12.1, 3.8 Hz, 2H).

The compound of Example 37 was prepared according to Reaction Example 24 below.

[Reaction Example 24]

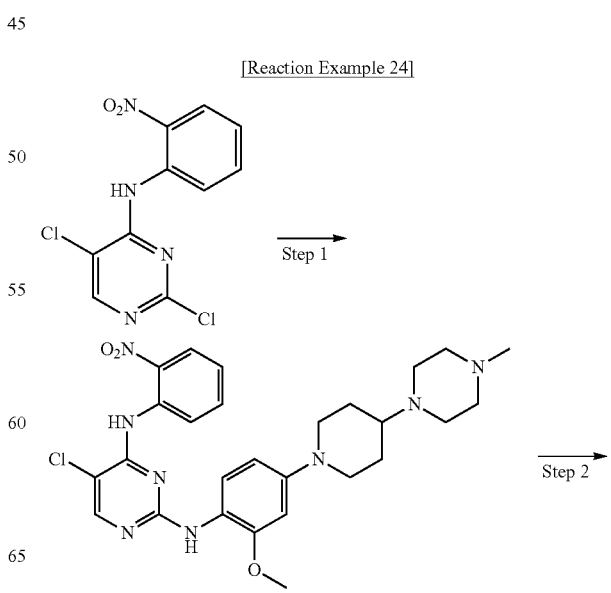

-continued

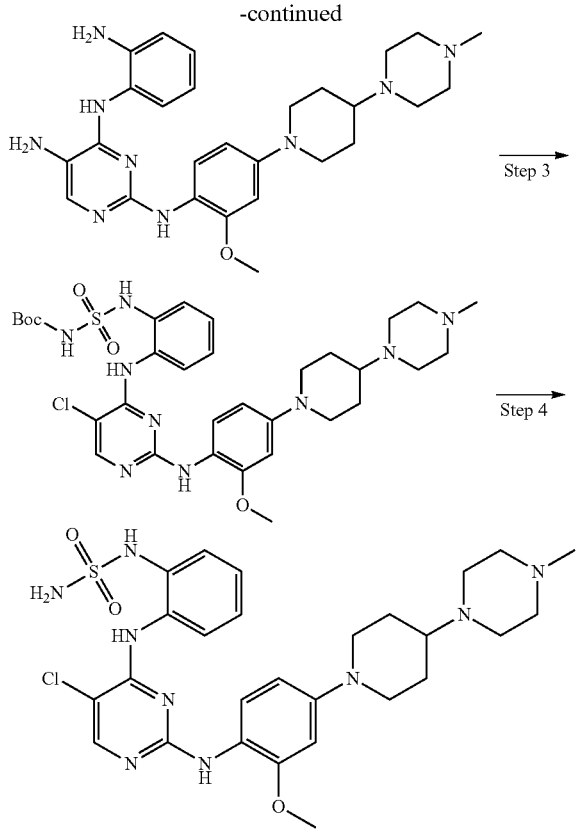

<Example 37> Preparation of (N-(2-((5-chloro-2-((2-methoxy-4-(4-(4-methylpiperazin-1-yl)piperidin-1-yl)phenyl)amino)pyrimidin-4-yl)amino)phenyl) sulfamoyl)carbamate Step 1: Preparation of 5-chloro-N2-(2-methoxy-4-(4-(4-methylpiperazin-1-yl)piperidin-1-yl)phenyl)-N4-(2-nitrophenyl)pyrimidin-2,4-diamine The same manner as in Step 1 of Example 6 above was performed to obtain 5-chloro-N2-(2-methoxy-4-(4-(4-methylpiperazin-1-yl)piperidin-1-yl)phenyl)-N4-(2-nitrophenyl)pyrimidin-2,4-diamine (130 mg, 44%).

$^1$H NMR (500 MHz, chloroform-d) 10.65 (s, 1H), 9.00 (dd, J=8.6, 1.3 Hz, 1H), 8.29 (dd, J=8.5, 1.7 Hz, 1H), 8.21 (s, 1H), 7.99 (d, J=8.7 Hz, 1H), 7.63 (t, J=7.7 Hz, 1H), 7.29 (s, 1H), 7.21-7.13 (m, 1H), 6.59 (d, J=2.5 Hz, 1H), 6.53 (dd, J=8.8, 2.5 Hz, 1H), 3.90 (s, 3H), 3.71 (d, J=11.8 Hz, 2H), 2.80-2.69 (m, 6H), 2.64-2.42 (m, 4H), 2.37 (s, 3H), 2.00 (d, J=12.4 Hz, 2H), 1.81-1.70 (m, 2H).

Step 2: Preparation of N4-(2-aminophenyl)-5-chloro-N2-(2-methoxy-4-(4-(4-methylpiperazin-1-yl)piperidin-1-yl)phenyl)pyrimidin-2,4-diamine The same manner as in Step 2 of Example 6 above was performed to obtain N4-(2-aminophenyl)-5-chloro-N2-(2-methoxy-4-(4-(4-methylpiperazin-1-yl)piperidin-1-yl)phenyl)pyrimidin-2,4-diamine (110 mg, 89%).

$^1$H NMR (500 MHz, chloroform-d) 8.04 (s, 1H), 7.93 (d, J=8.8 Hz, 1H), 7.40-7.34 (m, 2H), 7.18 (td, J=7.6, 1.5 Hz, 1H), 6.92-6.86 (m, 2H), 6.76 (s, 1H), 6.51 (d, J=2.5 Hz, 1H), 6.32 (d, J=8.8 Hz, 1H), 3.84 (s, 3H), 3.81 (bs, 2H), 3.62 (d, J=11.9 Hz, 3H), 2.72-2.36 (m, 12H), 2.34 (s, 3H), 1.96 (d, J=12.4 Hz, 2H), 1.77-1.67 (m, 3H).

Step 3: Preparation of tert-butyl (N-(2-((5-chloro-2-((2-methoxy-4-(4-(4-methylpiperazin-1-yl)piperidin-1-yl)phenyl)amino)pyrimidin-4-yl)amino)phenyl) sulfamoyl)carbamate The same manner as in Step 3 of Example 6 above was performed to obtain tert-butyl (N-(2-((5-chloro-2-((2-methoxy-4-(4-(4-methylpiperazin-1-yl)piperidin-1-yl)phenyl)amino)pyrimidin-4-yl)amino)phenyl)sulfamoyl)carbamate (65 mg, 44%).

$^1$H NMR (500 MHz, DMSO-$d_6$) 8.83 (s, 1H), 8.06 (s, 1H), 7.94 (d, J=8.1 Hz, 1H), 7.81 (s, 1H), 7.50 (d, J=8.7 Hz, 1H), 7.22 (d, J=1.7 Hz, 1H), 7.14-7.03 (m, 2H), 6.60 (d, J=2.5 Hz, 1H), 6.39 (dd, J=8.8, 2.4 Hz, 1H), 3.77 (s, 3H), 3.69 (d, J=12.1 Hz, 3H), 2.80-2.58 (m, 10H), 2.43 (bs, 4H), 1.85 (d, J=12.0 Hz, 3H), 1.56-1.47 (m, 2H), 1.38 (s, 9H).

Step 4: Preparation of (N-(2-((5-chloro-2-((2-methoxy-4-(4-(4-methylpiperazin-1-yl)piperidin-1-yl)phenyl)amino)pyrimidin-4-yl)amino)phenyl)sulfamoyl)carbamate The same manner as in Step 4 of Example 6 above was performed to obtain (N-(2-((5-chloro-2-((2-methoxy-4-(4-(4-methylpiperazin-1-yl)piperidin-1-yl)phenyl)amino)pyrimidin-4-yl)amino)phenyl)sulfamoyl)carbamate (50 mg, 66%).

$^1$H NMR (300 MHz, Methanol-$d_4$) δ 8.01 (dd, J=7.9, 1.6 Hz, 1H), 7.98 (s, 1H), 7.71 (d, J=8.8 Hz, 1H), 7.44 (dd, J=7.7, 1.7 Hz, 1H), 7.23-7.17 (m, 2H), 6.63 (d, J=2.5 Hz, 1H), 6.41 (dd, J=8.8, 2.5 Hz, 1H), 3.83 (s, 3H), 3.66 (d, J=12.2 Hz, 2H), 2.79-2.38 (m, 11H), 2.30 (s, 3H), 2.00 (d, J=12.3 Hz, 2H), 1.736-1.58 (m, 1H).

The compounds of Examples 38 and 39 were prepared according to Reaction Example 25 below.

[Reaction Example 25]

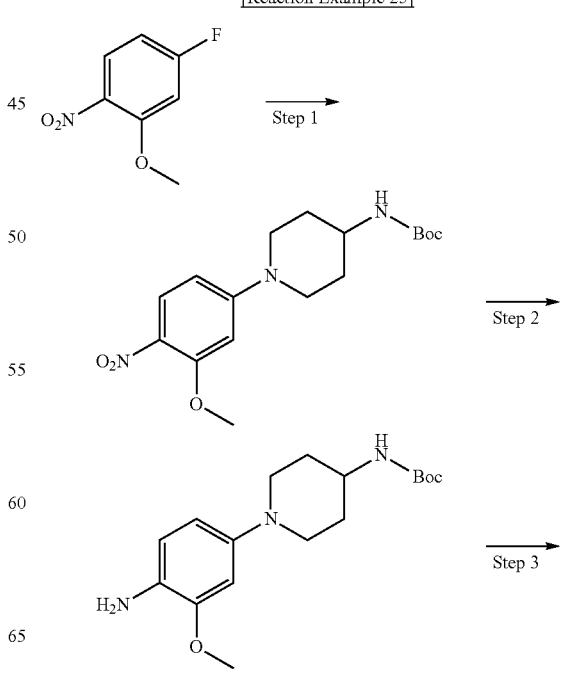

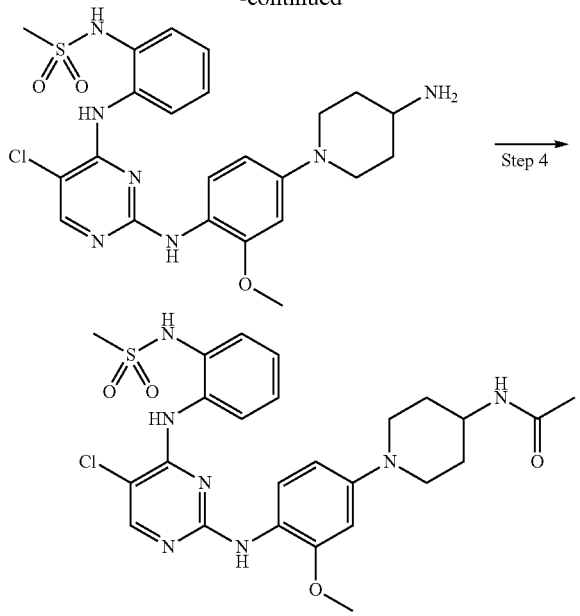

In which, the compound produced after the performance of Step 3 is the compound of Example 38, and the compound produced after the performance of Step 4 is the compound of Example 39.

<Example 38> Preparation of N-(2-((2-((4-(4-aminopiperidin-1-yl)-2-methoxyphenyl)amino)-5-chloropyrimidin-4-yl)amino)phenyl)methanesulfonamide Step 1: Preparation of tert-butyl (1-(3-methoxy-4-nitrophenyl)piperidin-4-yl)carbamate The same manner as in Step 1 of Example 19 above was performed to obtain tert-butyl (1-(3-methoxy-4-nitrophenyl)piperidin-4-yl)carbamate (400 mg, 78%).
$^1$H NMR (500 MHz, DMSO-$d_6$) 7.88 (d, J=9.5 Hz, 1H), 6.89 (d, J=7.8 Hz, 1H), 6.58 (dd, J=9.5, 2.5 Hz, 1H), 6.50 (d, J=2.5 Hz, 1H), 4.01-3.95 (m, 2H), 3.91 (s, 3H), 3.59-3.51 (m, 1H), 3.09-3.00 (m, 2H), 1.86-1.77 (m, 2H), 1.44-1.35 (m, 11H).

Step 2: Preparation of tert-butyl (1-(4-amino-3-methoxy phenyl)piperidin-4-yl)carbamate The same manner as in Step 2 of Example 19 above was performed to obtain tert-butyl (1-(4-amino-3-methoxyphenyl)piperidin-4-yl)carbamate (320 mg, 87%).
$^1$H NMR (500 MHz, DMSO-$d_6$) 6.85 (d, J=7.8 Hz, 1H), 6.57-6.51 (m, 2H), 6.33 (d, J=8.4 Hz, 1H), 4.87 (bs, 2H), 3.75 (s, 3H), 3.41-3.34 (m, 2H), 2.59 (t, J=11.8 Hz, 2H), 1.79 (d, J=12.1 Hz, 2H), 1.56-1.45 (m, 2H), 1.40 (s, 9H).

Step 3: Preparation of N-(2-((2-((4-(4-aminopiperidin-1-yl)-2-methoxyphenyl)amino)-5-chloropyrimidin-4-yl)amino)phenyl)methanesulfonamide The same manner as in Step 3 of Example 19 above was performed to obtain N-(2-((2-((4-(4-aminopiperidin-1-yl)-2-methoxyphenyl)amino)-5-chloropyrimidin-4-yl)amino)phenyl)methanesulfonamide (80 mg, 49%).
$^1$H NMR (300 MHz, DMSO-$d_6$) 9.31 (s, 1H), 8.97 (bs, 1H), 8.16 (s, 1H), 7.95-7.88 (bs, 2H), 7.83 (d, J=3.7 Hz, 1H), 7.47-7.40 (m, 1H), 7.35 (d, J=8.5 Hz, 1H), 7.30-7.23 (m, 2H), 6.66 (d, J=2.3 Hz, 1H), 6.40 (d, J=8.9 Hz, 1H), 3.78 (s, 3H), 3.73 (d, J=12.7 Hz, 2H), 3.22 (bs, 1H), 2.97 (s, 3H), 2.80 (t, J=12.6 Hz, 2H), 1.97 (d, J=11.9 Hz, 2H), 1.69-1.54 (m, 1H).

<Example 39> Preparation of N-(1-(4-((5-chloro-4-((2-(methylsulfonamido)phenyl)amino)pyrimidin-2-yl)amino)-3-methoxyphenyl)piperidin-4-yl)acetamide The same manner as in Example 15 above was performed to obtain N-(1-(4-((5-chloro-4-((2-(methylsulfonamido)phenyl)amino)pyrimidin-2-yl)amino)-3-methoxyphenyl)piperidin-4-yl)acetamide (25 mg, 78%).
$^1$H NMR (500 MHz, DMSO-$d_6$) 9.28 (s, 1H), 8.47 (s, 1H), 8.09 (s, 1H), 8.01 (d, J=8.1 Hz, 1H), 7.90 (s, 1H), 7.84 (d, J=7.7 Hz, 1H), 7.42 (d, J=8.7 Hz, 1H), 7.37 (dd, J=7.8, 1.6 Hz, 1H), 7.24 (d, J=7.9 Hz, 1H), 7.19 (td, J=7.6, 1.6 Hz, 1H), 6.61 (d, J=2.5 Hz, 1H), 6.38 (dd, J=8.7, 2.5 Hz, 1H), 3.76 (s, 3H), 3.70 (bs, 1H), 3.61 (d, J=12.4 Hz, 2H), 2.96 (s, 3H), 2.75 (t, J=10.7 Hz, 1H), 1.86-1.79 (m, 5H), 1.55-1.44 (m, 2H).

The compound of Example 40 was prepared according to Reaction Example 26 below.

[Reaction Example 26]

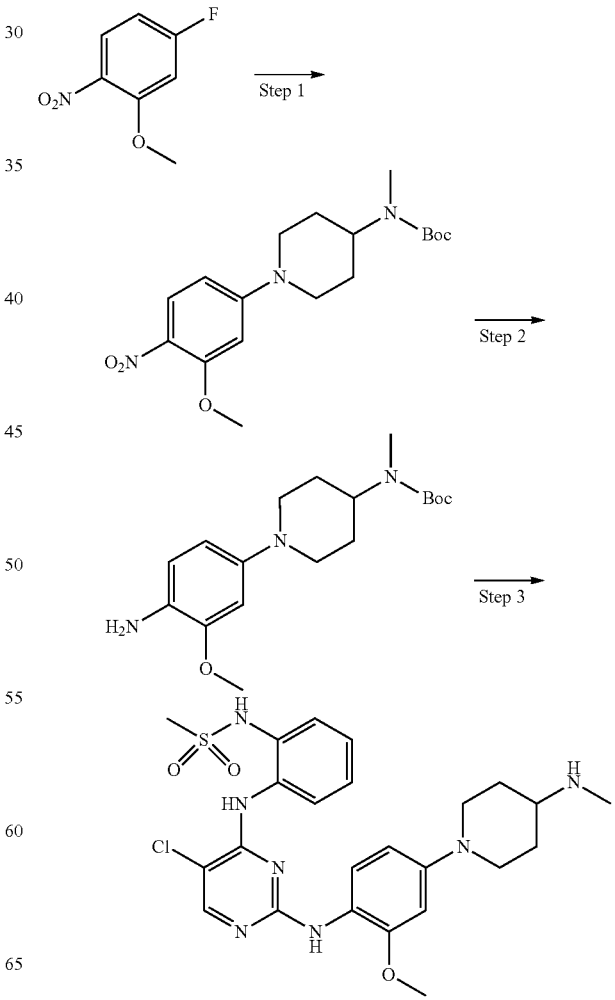

<Example 40> Preparation of N-(2-((5-chloro-2-((2-methoxy-4-(4-(methylamino)piperidin-1-yl)phenyl)amino)pyrimidin-4-yl)amino)phenyl)methanesulfonamide

Step 1: Preparation of tert-butyl (1-(3-methoxy-4-nitrophenyl)piperidin-4-yl)(methyl)carbamate The same manner as in Step 1 of Example 19 above was performed to obtain tert-butyl (1-(3-methoxy-4-nitrophenyl)piperidin-4-yl)(methyl)carbamate (450 mg, 84%).

$^1$H NMR (300 MHz, chloroform-d) 8.02 (d, J=9.3 Hz, 1H), 6.44 (dd, J=9.4, 2.6 Hz, 1H), 6.34 (d, J=2.5 Hz, 1H), 4.07-3.98 (m, 2H), 3.97 (s, 3H), 3.10-2.96 (m, 2H), 2.75 (s, 3H), 1.85-1.76 (m, 2H), 1.50 (s, 9H).

Step 2: Preparation of tert-butyl (1-(4-amino-3-methoxy phenyl)piperidin-4-yl)(methyl)carbamate The same manner as in Step 2 of Example 19 above was performed to obtain tert-butyl (1-(4-amino-3-methoxyphenyl)piperidin-4-yl)(methyl)carbamate (400 mg, 96%).

$^1$H NMR (300 MHz, chloroform-d) δ 6.66 (d, J=8.3 Hz, 1H), 6.56 (bs, 1H), 6.50-6.40 (m, 1H), 3.86 (s, 3H), 3.53 (d, J=12.2 Hz, 3H), 2.80 (s, 3H), 2.71 (d, J=12.2 Hz, 2H), 1.99-1.83 (m, 2H), 1.80-1.69 (m, 2H), 1.50 (s, 9H).

Step 3: Preparation of N-(2-((5-chloro-2-((2-methoxy-4-(4-(methylamino)piperidin-1-yl)phenyl)amino)pyrimidin-4-yl)amino)phenyl)methanesulfonamide The same manner as in Step 3 of Example 19 above was performed to obtain N-(2-((5-chloro-2-((2-methoxy-4-(4-(methylamino)piperidin-1-yl)phenyl)amino)pyrimidin-4-yl)amino)phenyl)methanesulfonamide (50 mg, 33%).

$^1$H NMR (300 MHz, DMSO-d$_6$) 8.96 (s, 1H), 8.12 (d, J=7.9 Hz, 1H), 8.03 (s, 1H), 7.89 (s, 1H), 7.48 (d, J=8.7 Hz, 1H), 7.29-7.19 (m, 1H), 6.94 (td, J=7.7, 1.6 Hz, 1H), 6.81 (t, J=7.7 Hz, 1H), 6.63 (d, J=2.5 Hz, 1H), 6.46 (dd, J=8.7, 2.5 Hz, 1H), 3.77 (s, 3H), 3.71 (d, J=12.6 Hz, 2H), 2.90-2.81 (m, 1H), 2.78 (s, 3H), 2.71 (d, J=12.2 Hz, 2H), 2.49 (s, 3H), 1.99 (d, J=12.3 Hz, 2H), 1.59-1.50 (m, 2H).

The compounds of Example 41, 42, and 43 were prepared according to Reaction Example 27 below.

[Reaction Example 27]

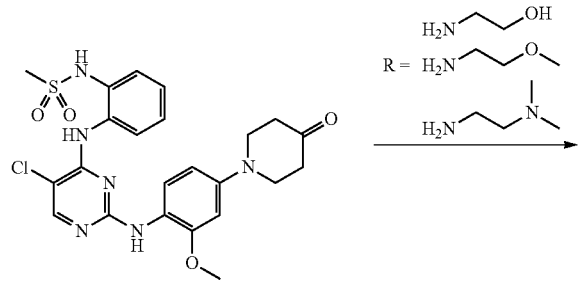

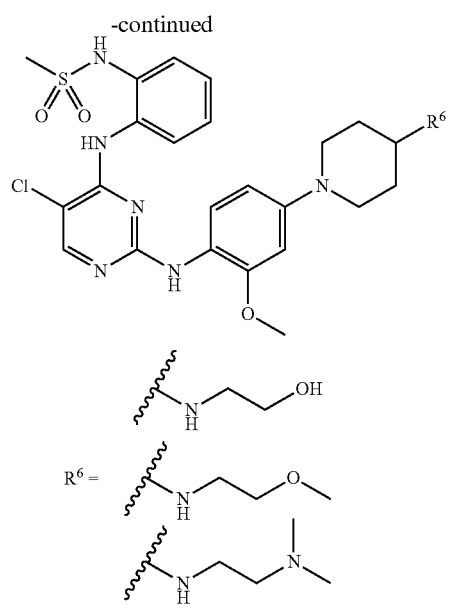

In which,

R represents a substance reacting with a starting material, the compound wherein $R^6$ is —NH(CH$_2$)$_2$OH is the compound of Example 41, the compound wherein $R^6$ is —NH(CH$_2$)$_2$OCH$_3$ is the compound of Example 42, and the compound wherein $R^6$ is —NH(CH$_2$)$_2$N(CH$_3$)$_2$ is the compound of Example 43.

<Example 41> Preparation of N-(2-((5-chloro-2-((4-(4-((2-hydroxyethyl)amino)piperidin-1-yl)-2-methoxyphenyl)amino)pyrimidin-4-yl)amino)phenyl)methanesulfonamide The same manner as in Example 19 above was performed to obtain N-(2-((5-chloro-2-((4-(4-((2-hydroxyethyl)amino)piperidin-1-yl)-2-methoxy phenyl)amino)pyrimidin-4-yl)amino)phenyl)methanesulfonamide (25 mg, 46%).

$^1$H NMR (300 MHz, Methanol-d$_4$) 8.06 (s, 1H), 7.81 (d, J=7.5 Hz, 1H), 7.56-7.50 (m, 1H), 7.44-7.35 (m, 2H), 7.31 (d, J=8.7 Hz, 1H), 6.71 (d, J=2.4 Hz, 1H), 6.51 (d, J=8.7 Hz, 1H), 3.93-3.81 (m, 7H), 3.23 (t, J=5.2 Hz, 2H), 2.99 (s, 3H), 2.87 (dd, J=13.4, 11.2 Hz, 2H), 2.25 (d, J=12.4 Hz, 2H), 1.90-1.73 (m, 2H).

<Example 42> Preparation of N-(2-((5-chloro-2-((2-methoxy-4-(4-((2-methoxyethyl)amino)piperidin-1-yl)phenyl)amino)pyrimidin-4-yl)amino)phenyl)methanesulfonamide The same manner as in Example 19 above was performed to obtain N-(2-((5-chloro-2-((2-methoxy-4-(4-((2-methoxyethyl)amino)piperidin-1-yl)phenyl)amino)pyrimidin-4-yl)amino)phenyl)methanesulfonamide (22 mg, 40%).

$^1$H NMR (300 MHz, Methanol-d$_4$) 8.06 (s, 1H), 7.82 (d, J=8.8 Hz, 1H), 7.56-7.50 (m, 1H), 7.42-7.35 (m, 2H), 7.33 (d, J=8.6 Hz, 1H), 6.70 (d, J=2.5 Hz, 1H), 6.50 (d, J=8.9 Hz, 1H), 3.91-3.80 (m, 5H), 3.73-3.65 (m, 2H), 3.45 (s, 3H), 3.32-3.27 (m, 2H), 2.98 (s, 3H), 2.85 (t, J=12.0 Hz, 2H), 2.28-2.19 (m, 2H), 1.87-1.72 (m, 2H).

<Example 43> Preparation of N-(2-((5-chloro-2-((4-(4-((2-(dimethylamino)ethyl)amino)piperidin-1-yl)-2-methoxyphen yl)amino)pyrimidin-4-yl)amino)phenyl)methanesulfonamide The same manner as in Example 19 above was performed to obtain N-(2-((5-chloro-2-((4-(4-((2-(dimethylamino)ethyl)amino)piperidin-1-yl)-2-methoxyphenyl)amino)pyrimidin-4-yl)amino)phenyl)methanesulfonamide (10 mg, 18%).

$^1$H NMR (300 MHz, Methanol-$d_4$) δ 8.07 (s, 1H), 7.78 (d, J=7.6 Hz, 1H), 7.54 (dd, J=7.6, 1.9 Hz, 1H), 7.45-7.41 (m, 1H), 7.38 (dd, J=7.5, 2.0 Hz, 1H), 7.28 (d, J=8.7 Hz, 1H), 6.75 (d, J=2.5 Hz, 1H), 6.61-6.50 (m, 1H), 3.90 (d, J=11.7 Hz, 2H), 3.86 (s, 3H), 3.64-3.54 (m, 4H), 3.50-3.40 (m, 1H), 3.02 (s, 6H), 3.00 (s, 4H), 2.93 (d, J=11.6 Hz, 2H), 2.28 (d, J=12.4 Hz, 2H), 1.94-1.78 (m, 2H).

The chemical structures of the compounds prepared in Examples 1-43 were arranged and indicated in Tables 1 to 3 below.

TABLE 1

| Example | Chemical Structure |
|---|---|
| 1 | 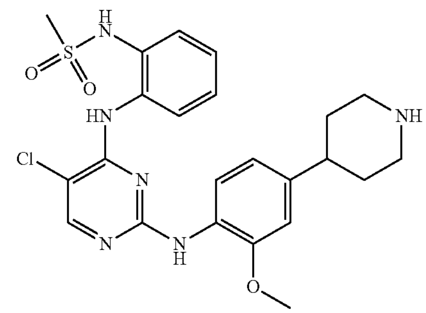 [SMILES: COc1cc(C2CCNCC2)ccc1Nc1ncc(Cl)c(Nc2ccccc2NS(C)(=O)=O)n1] |
| 2 | 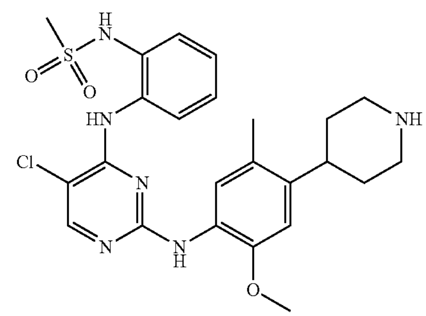 [SMILES: COc1cc(C2CCNCC2)c(C)cc1Nc1ncc(Cl)c(Nc2ccccc2NS(C)(=O)=O)n1] |
| 3 | 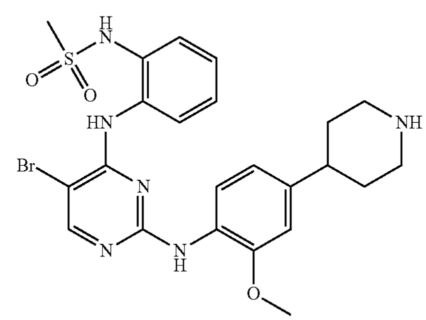 |
| 4 | 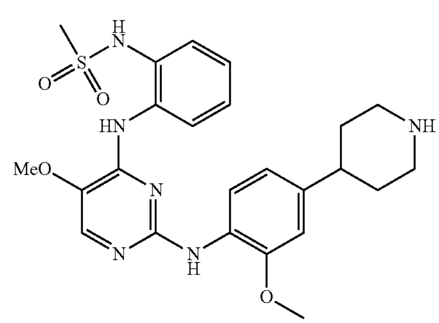 [SMILES: COc1cc(C2CCNCC2)ccc1Nc1ncc(OC)c(Nc2ccccc2NS(C)(=O)=O)n1] |

TABLE 1-continued

| Example | Chemical Structure |
|---------|-------------------|
| 5 | 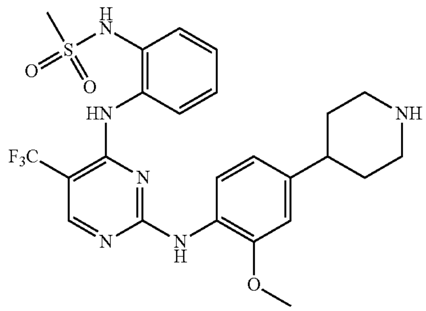 [SMILES: COc1cc(C2CCNCC2)ccc1Nc1ncc(C(F)(F)F)c(Nc2ccccc2NS(C)(=O)=O)n1] |
| 6 | 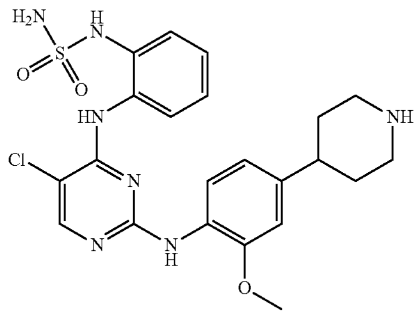 |
| 7 | 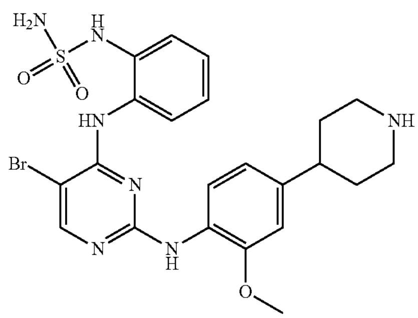 [SMILES: COc1cc(C2CCNCC2)ccc1Nc1ncc(Cl)c(Nc2ccccc2NS(N)(=O)=O)n1] |
| 8 | 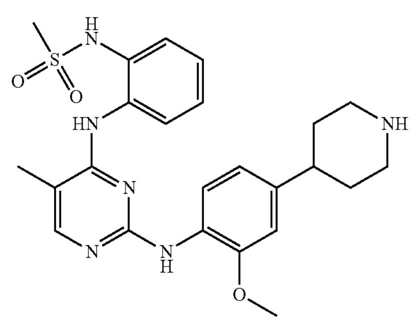 [SMILES: COc1cc(C2CCNCC2)ccc1Nc1ncc(C)c(Nc2ccccc2NS(C)(=O)=O)n1] |
| 9 | 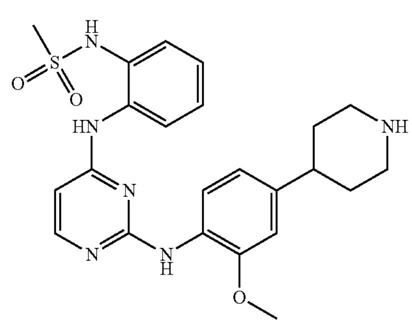 [SMILES: COc1cc(C2CCNCC2)ccc1Nc1nccc(Nc2ccccc2NS(C)(=O)=O)n1] |

TABLE 1-continued
| Example | Chemical Structure |
| --- | --- |
| 10 | 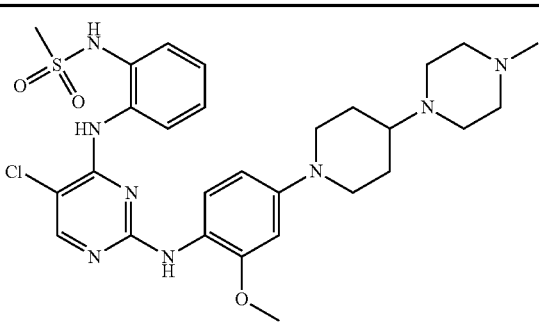 |
| 11 | 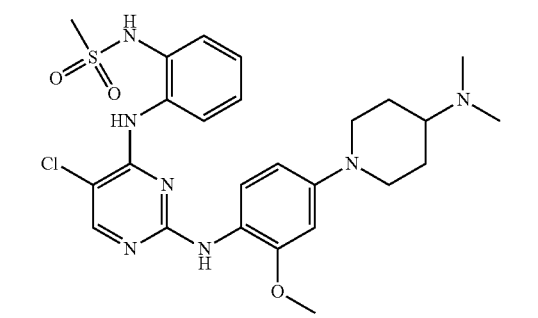 [SMILES: COc1cc(N2CCC(N(C)C)CC2)ccc1Nc1ncc(Cl)c(Nc2ccccc2NS(C)(=O)=O)n1] |
| 12 | 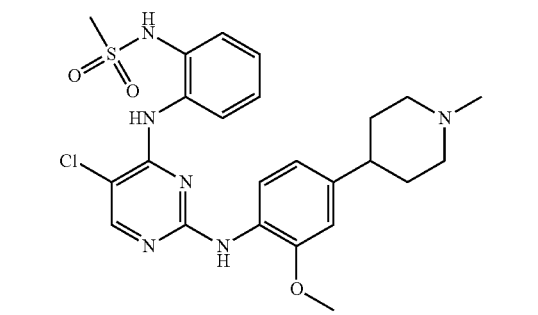 [SMILES: COc1cc(C2CCN(C)CC2)ccc1Nc1ncc(Cl)c(Nc2ccccc2NS(C)(=O)=O)n1] |
| 13 | 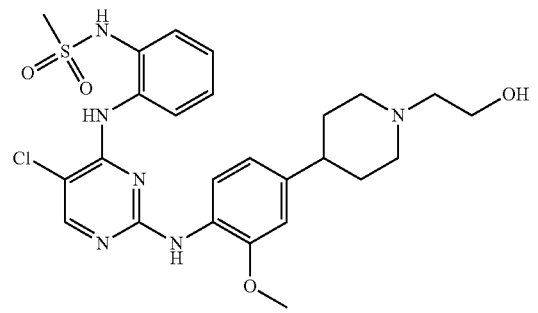 [SMILES: COc1cc(C2CCN(CCO)CC2)ccc1Nc1ncc(Cl)c(Nc2ccccc2NS(C)(=O)=O)n1] |
| 14 | 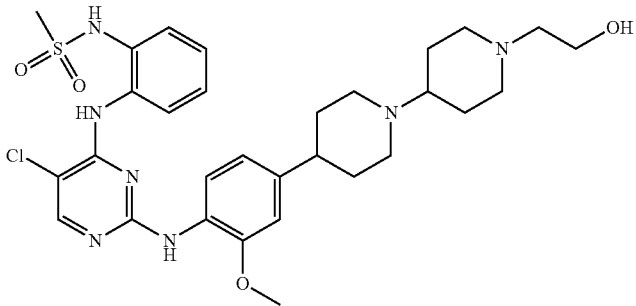 [SMILES: COc1cc(C2CCN(C3CCN(CCO)CC3)CC2)ccc1Nc1ncc(Cl)c(Nc2ccccc2NS(C)(=O)=O)n1] |

TABLE 1-continued
| Example | Chemical Structure |
|---|---|
| 15 | 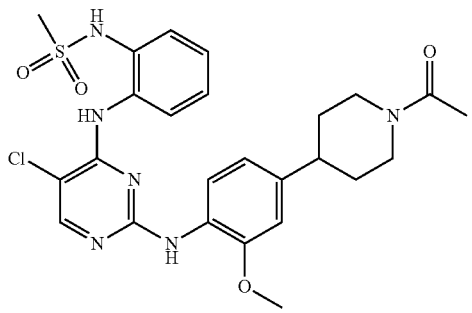 [SMILES: COc1cc(C2CCN(C(C)=O)CC2)ccc1Nc1ncc(Cl)c(Nc2ccccc2NS(C)(=O)=O)n1] |
| 16 | 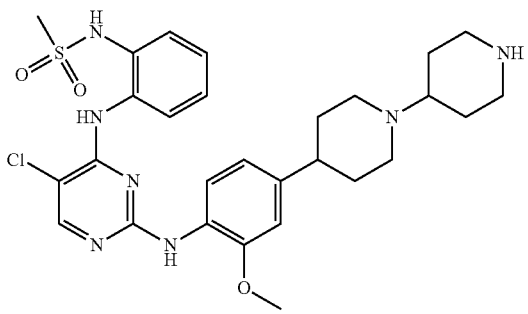 [SMILES: COc1cc(C2CCN(C3CCNCC3)CC2)ccc1Nc1ncc(Cl)c(Nc2ccccc2NS(C)(=O)=O)n1] |
TABLE 2
| Example | Chemical Structure |
|---|---|
| 17 | 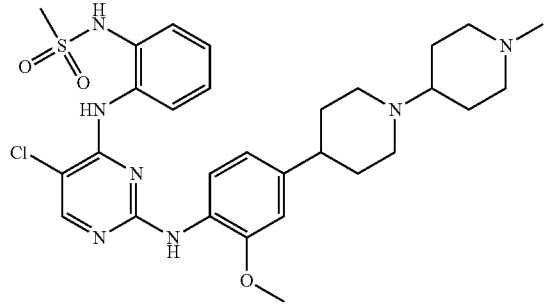 [SMILES: COc1cc(C2CCN(C3CCN(C)CC3)CC2)ccc1Nc1ncc(Cl)c(Nc2ccccc2NS(C)(=O)=O)n1] |
| 18 | 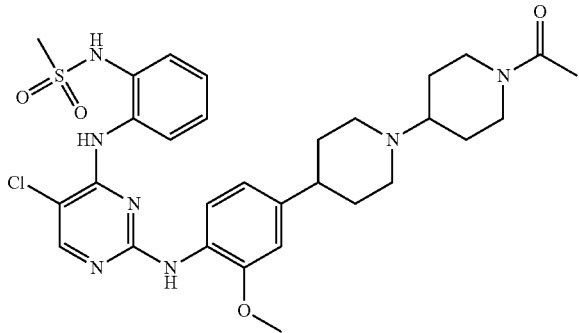 [SMILES: COc1cc(C2CCN(C3CCN(C(C)=O)CC3)CC2)ccc1Nc1ncc(Cl)c(Nc2ccccc2NS(C)(=O)=O)n1] |

TABLE 2-continued

| Example | Chemical Structure |
|---|---|
| 19 | 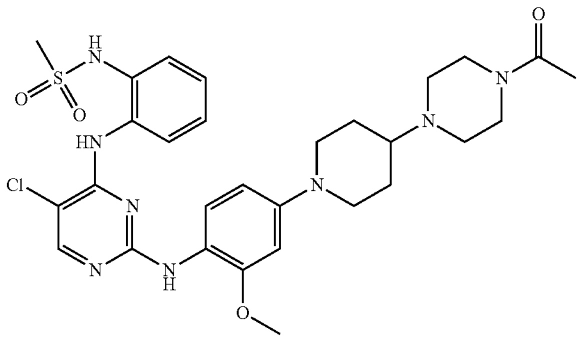 [SMILES: COc1cc(N2CCC(N3CCN(C(C)=O)CC3)CC2)ccc1Nc1ncc(Cl)c(Nc2ccccc2NS(C)(=O)=O)n1] |
| 20 | 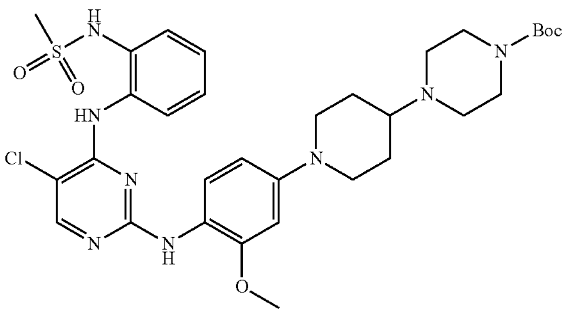 [SMILES: COc1cc(N2CCC(N3CCN(C(=O)OC(C)(C)C)CC3)CC2)ccc1Nc1ncc(Cl)c(Nc2ccccc2NS(C)(=O)=O)n1] |
| 21 | 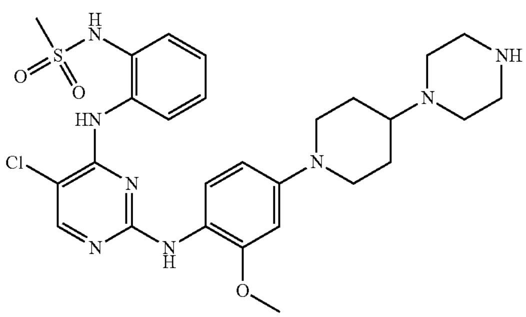 [SMILES: COc1cc(N2CCC(N3CCNCC3)CC2)ccc1Nc1ncc(Cl)c(Nc2ccccc2NS(C)(=O)=O)n1] |
| 22 | 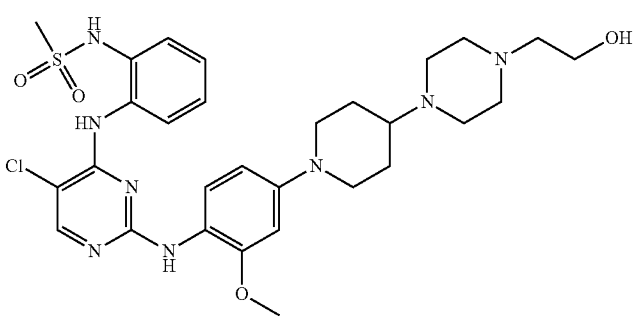 [SMILES: COc1cc(N2CCC(N3CCN(CCO)CC3)CC2)ccc1Nc1ncc(Cl)c(Nc2ccccc2NS(C)(=O)=O)n1] |
| 23 | 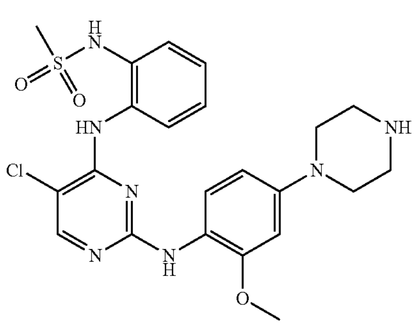 |

TABLE 2-continued

| Example | Chemical Structure |
|---|---|
| 24 | 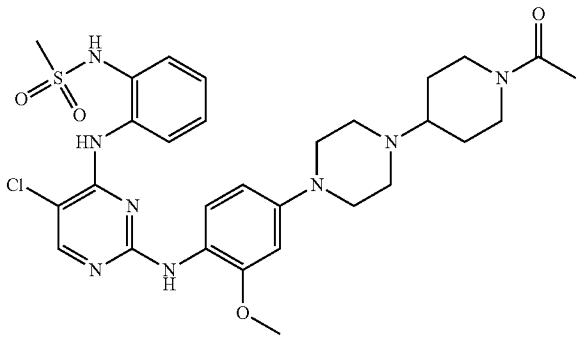 [SMILES: COc1cc(N2CCN(C3CCN(C(C)=O)CC3)CC2)ccc1Nc1ncc(Cl)c(Nc2ccccc2NS(C)(=O)=O)n1] |
| 25 | 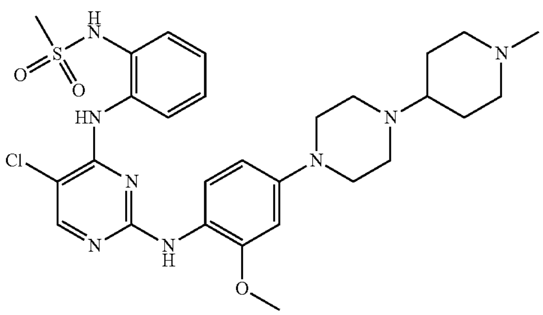 [SMILES: COc1cc(N2CCN(C3CCN(C)CC3)CC2)ccc1Nc1ncc(Cl)c(Nc2ccccc2NS(C)(=O)=O)n1] |
| 26 | 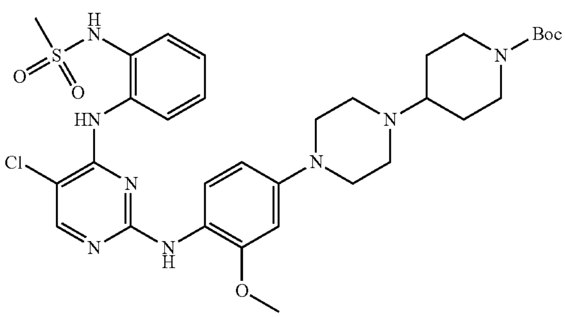 [SMILES: COc1cc(N2CCN(C3CCN(C(=O)OC(C)(C)C)CC3)CC2)ccc1Nc1ncc(Cl)c(Nc2ccccc2NS(C)(=O)=O)n1] |
| 27 | 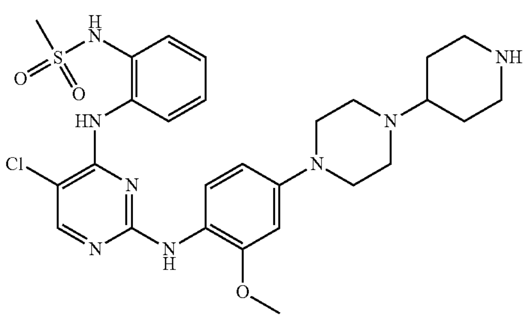 [SMILES: COc1cc(N2CCN(C3CCNCC3)CC2)ccc1Nc1ncc(Cl)c(Nc2ccccc2NS(C)(=O)=O)n1] |
| 28 | 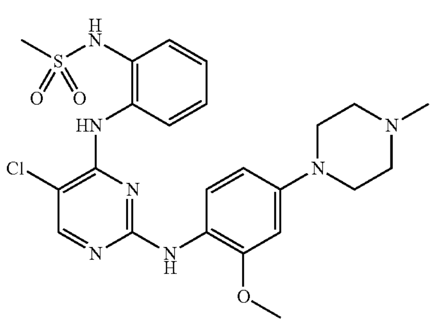 |

TABLE 2-continued

| Example | Chemical Structure |
|---|---|
| 29 | *(structure)* |
| 30 | *(structure)* |
| 31 | *(structure)* |
| 32 | *(structure)* |

TABLE 3

| Example | Chemical Structure |
|---------|-------------------|
| 33 | 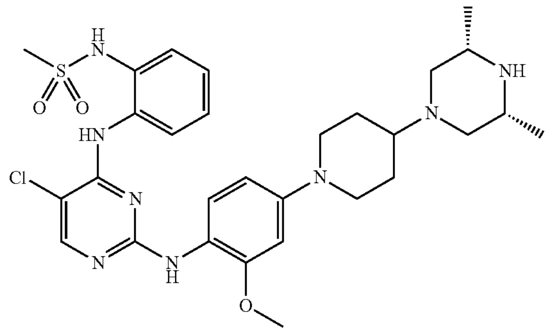 |
| 34 | 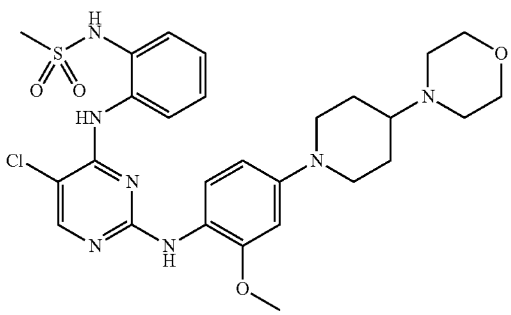 [SMILES: COc1cc(N2CCC(N3CCOCC3)CC2)ccc1Nc1ncc(Cl)c(Nc2ccccc2NS(C)(=O)=O)n1] |
| 35 | 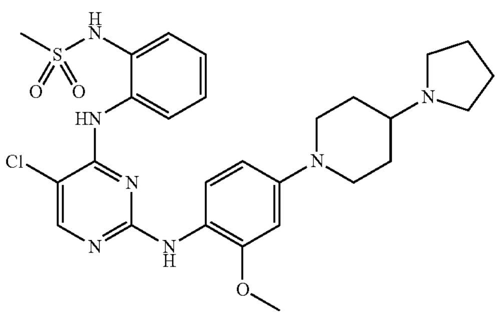 [SMILES: COc1cc(N2CCC(N3CCCC3)CC2)ccc1Nc1ncc(Cl)c(Nc2ccccc2NS(C)(=O)=O)n1] |
| 36 | 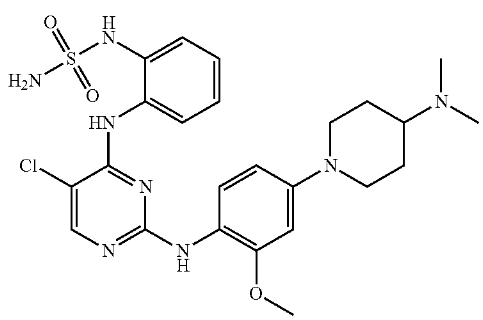 [SMILES: COc1cc(N2CCC(N(C)C)CC2)ccc1Nc1ncc(Cl)c(Nc2ccccc2NS(N)(=O)=O)n1] |
| 37 | 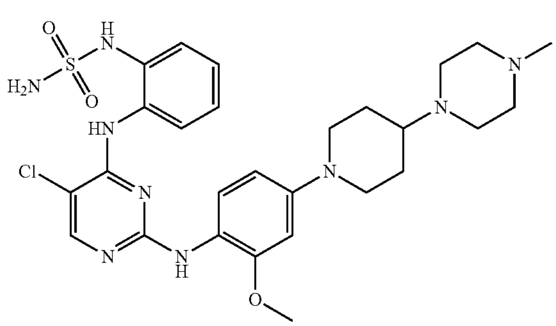 [SMILES: COc1cc(N2CCC(N3CCN(C)CC3)CC2)ccc1Nc1ncc(Cl)c(Nc2ccccc2NS(N)(=O)=O)n1] |

TABLE 3-continued

| Example | Chemical Structure |
|---|---|
| 38 | 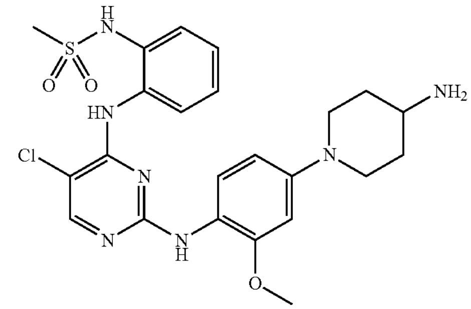 [SMILES: COc1cc(N2CCC(N)CC2)ccc1Nc1ncc(Cl)c(Nc2ccccc2NS(C)(=O)=O)n1] |
| 39 | 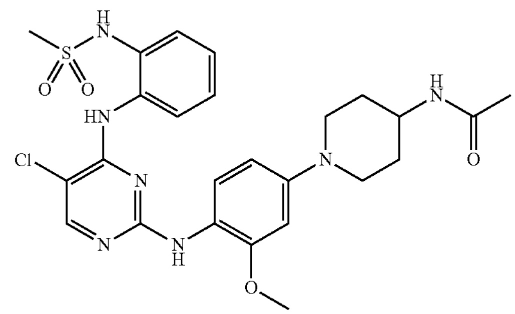 [SMILES: COc1cc(N2CCC(NC(C)=O)CC2)ccc1Nc1ncc(Cl)c(Nc2ccccc2NS(C)(=O)=O)n1] |
| 40 | 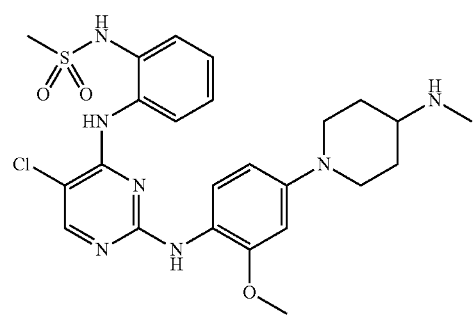 |
| 41 | 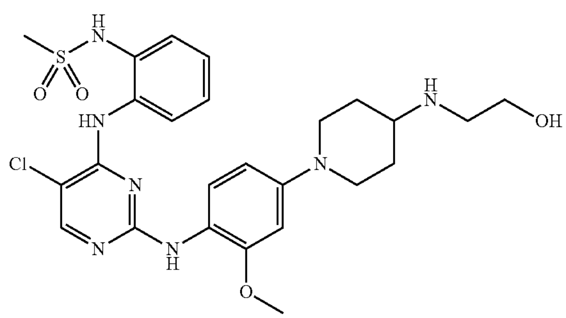 [SMILES: COc1cc(N2CCC(NCCO)CC2)ccc1Nc1ncc(Cl)c(Nc2ccccc2NS(C)(=O)=O)n1] |
| 42 | 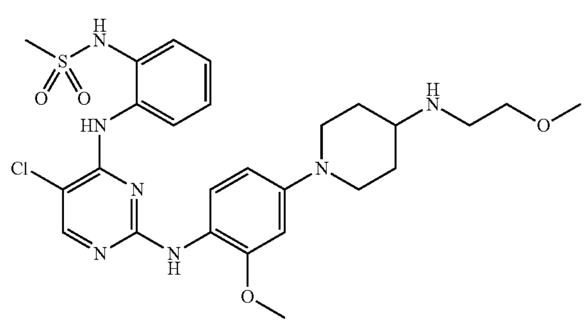 |

TABLE 3-continued

| Example | Chemical Structure |
|---|---|
| 43 | (structure: chloropyrimidine with methanesulfonamide-phenyl-amine, and methoxyphenyl-piperidine-ethylamine-dimethylamino substituents) |

<Experimental Example 1> Measurement of an inhibitory ability on wild-type EGFR and EGFR mutation of the compound represented by Formula 1 according to the present invention (N2,N4-diphenylpyrimidin-2,4-diamine derivative)

In order to confirm an inhibitory ability on wild-type EGFR and EGFR mutation of the compound represented by Formula 1 according to the present invention, the experiment was carried out as described below. The results are shown in Table 4 below.

The measurement of an activity on wild-type and EGFR mutation enzyme of the compound of the present invention was experimented by utilizing the HTRF system sold by Cisbio, as follow. Wild-type EGFR and EGFR del19, EGFR del19/T790M mutation enzyme were used by purchasing the recombinant proteins provided by Carna Biosciences, and EGFR del19/T790M/C797S mutation enzyme was used as an enzyme source by purchasing the proteins provided by SignalChem.

The composition of the assay buffer used in the activity measurement was 50 mM Tris-HCl pH 7.5, 100 mM NaCl, 7.5 mM $MgCl_2$, 3 mM KCl, 0.01% Tween 20, 0.1% BSA, 1 mM DTT. The enzymatic reaction was carried out hereto by using the peptide substrate labeled with ATP of 50 mM concentration and biotin of 0.5 mM concentration. The analysis of an EGFR activity inhibitory effect of the compound was carried out in accordance with the analysis reaction recipe below.

Component 1: 4 ml of EGFR wild-type or mutation enzyme
Component 2: 2 ml of compound solution
Component 3: 4 ml of peptide labeled with ATP and biotin The enzymatic reaction was initiated by mixing Component 1 and Component 2 first, and then, adding component 3. After the reaction for 2 hours at 37° C., 10 ml of a measurement solution consisting of streptavidin-XL665 provided by Cisbio and anti-phosphotyrosine antibody labeled with europium was added to the enzymatic reaction solution and reacted for 1 hour at ambient temperature. Finally, the ratio of fluorescence values at 615 nm and 665 nm was obtained by using the Envision equipment of Perkin-Elmer, and the enzymatic activity was quantitatively measured, and the inhibitory ability of the compound was confirmed. The measurement values measured at the seven concentrations of the compound were analyzed by using the Prism program (version 5.01, Graphpad Software, Inc.), and $IC_{50}$ value of the compound was calculated, which is an inhibitory ability indicator.

TABLE 4

| Example | EGFR wt. $IC_{50}$ (μM) | EGFR del19 $IC_{50}$ (μM) | EGFR del19/T790M $IC_{50}$ (μM) | EGFR del19/T790M/C797S $IC_{50}$ (μM) |
|---|---|---|---|---|
| 1 | 2.1 | 0.020 | 0.016 | 0.015 |
| 2 | 0.73 | 0.012 | 0.012 | 0.003 |
| 3 | 0.84 | 0.018 | 0.005 | 0.002 |
| 4 | nd | nd | nd | 0.72 |
| 5 | 4.3 | 0.033 | 0.013 | 0.014 |
| 6 | 0.39 | 0.026 | 0.010 | 0.011 |
| 7 | >10 | 0.079 | 0.038 | 0.002 |
| 8 | nd | nd | nd | 0.36 |
| 9 | nd | nd | nd | 0.093 |
| 10 | 0.43 | 0.0007 | 0.004 | 0.0002 |
| 11 | 0.28 | 0.0078 | 0.0031 | 0.006 |
| 12 | 1.2 | 0.022 | 0.13 | 0.002 |
| 13 | 1.9 | 0.013 | 0.25 | 0.033 |
| 14 | 1.4 | 0.006 | 0.095 | 0.034 |
| 15 | nd | nd | nd | 0.33 |
| 16 | 5.4 | 0.044 | 0.34 | 0.023 |
| 17 | 0.6 | 0.004 | 0.078 | 0.012 |
| 18 | 0.97 | 0.013 | 0.092 | 0.03 |
| 19 | 0.7 | 0.0007 | 0.069 | 0.042 |
| 20 | nd | nd | nd | 0.3 |
| 21 | 0.16 | 0.0001 | 0.014 | 0.005 |
| 22 | 0.26 | 0.0004 | 0.031 | 0.0008 |
| 23 | 2.7 | 0.025 | 0.032 | 0.029 |
| 24 | 0.82 | 0.003 | 0.064 | 0.012 |
| 25 | 0.3 | 0.0002 | 0.018 | 0.009 |
| 26 | nd | nd | nd | 0.11 |
| 27 | 0.28 | 0.0003 | 0.021 | 0.001 |
| 28 | 0.64 | 0.0009 | 0.027 | 0.009 |
| 29 | 1.2 | 0.005 | 0.004 | 0.007 |
| 30 | 1.8 | 0.024 | 0.034 | 0.003 |
| 31 | 0.58 | 0.036 | 0.029 | 0.007 |
| 32 | 1.3 | 0.004 | 0.16 | 0.014 |
| 33 | nd | nd | nd | <0.001 |
| 34 | nd | nd | nd | <0.001 |
| 35 | 0.027 | 0.0011 | 0.0083 | <0.001 |
| 36 | nd | nd | nd | 0.0003 |
| 37 | 0.0028 | 0.0071 | 0.0027 | 0.0002 |
| 38 | nd | nd | nd | 0.0005 |
| 39 | nd | nd | nd | 0.0003 |
| 40 | nd | nd | nd | 0.0004 |
| 41 | nd | nd | nd | 0.0002 |
| 42 | nd | nd | nd | 0.0003 |
| 43 | nd | nd | nd | 0.0006 |

In Table 4 above, nd refers to no data.

As indicated in Table 4 above, it can be seen that all the example compounds of the present invention show a relatively weak EGFR activity inhibitory effect on wild-type EGFR, a selectively high inhibitory ability on EGFR mutation, in particular, and a high inhibitory ability on EGFR del19/T790M/C797S, which is a triple mutation.

<Experimental Example 2> Measurement of an inhibitory ability on wild-type Ba/F3 EGFR and Ba/F3 EGFR mutation in Ba/F3 cell line of the compound represented by Formula 1 according to the present invention (N2,N4-diphenylpyrimidin-2,4-diamine derivative)

In order to confirm an inhibitory ability on wild-type Ba/F3 EGFR and Ba/F3 EGFR mutation in Ba/F3 cell line of the compound represented by Formula 1 according to the present invention, the experiment was carried out as described below. The results are shown in Table 5 below.

The measurement of an activity on wild-type and mutation Ba/F3 EGFR cell line of the compound of the present invention was experimented by utilizing the CellTiter-Glo system sold by Promega, as follow. The CellTiter-Glo assay is a method for measuring the ATP present in cells in cell culture conditions to determine the cell viability. Ba/F3 EGFR wild-type and Ba/F3 EGFR del19, Ba/F3 EGFR del19/T790M, Ba/F3 del19/T790M/C797S mutation cell lines were used by purchasing the cell lines provided by Crown Bioscience, Inc. Ba/F3 EGFR wild-type and Ba/F3 EGFR del19, Ba/F3 EGFR del19/T790M, Ba/F3 del19/T790M/C797S mutation cell lines were cultured in 37° C., 5% $CO_2$ incubator by adding puromycine 1 ug to RPMI containing 10% FBS, 1% penicillin-streptomycin.

The analysis of an EGFR inhibitory ability effect of the compound was carried out in accordance with the analysis reaction recipe below.

2500 cells/90 ul was cultured by passage in 96 well cell culture plate, and after 24 hours, treated with the compound represented by Formula 1 in concentrations of 0, 0.01, 0.03, 0.1, 0.3, 1, 3, 10 (μM). After the reaction of 72 hours, the plate treated with the compound was allowed to stand for 30 minutes at ambient temperature, and then, was further treated with 100 μl of the reagent, and was shaked for 10 minutes at ambient temperature. Finally, the ratio of fluorescence values at 570 nm was obtained by using the equipment and quantitatively measured, and the inhibitory ability of the compound was confirmed. The measurement values measured at the eight concentrations of the compound were analyzed by using the Prism program (version 5.01, Graphpad Software, Inc.), and $IC_{50}$ value of the compound was calculated, which is an inhibitory ability indicator.

TABLE 5

| Example | Ba/F3 EGFR wt. $IC_{50}$ (μM) | Ba/F3 EGFR del19 $IC_{50}$ (μM) | Ba/F3 EGFR del19/T790M $IC_{50}$ (μM) | Ba/F3 EGFR del19/T790M/C797S $IC_{50}$ (μM) |
|---|---|---|---|---|
| 1 | >15 | 6.6 | 7.1 | nd |
| 2 | 2.8 | 3.8 | 1.8 | 2.4 |
| 3 | 4.1 | 1 | 1.2 | 1.6 |
| 5 | 2.4 | 0.26 | 0.57 | 0.79 |
| 6 | >15 | 6.4 | 9 | 5.8 |
| 7 | 3.4 | 0.47 | 1.6 | 3.3 |
| 10 | 1 | 0.18 | 0.099 | 0.063 |
| 11 | 0.34 | 0.0047 | 0.031 | 0.038 |
| 12 | 0.32 | 0.33 | 0.38 | 0.08 |
| 13 | 4.4 | 0.98 | 0.65 | 1.5 |
| 14 | 0.75 | 0.5 | 0.54 | 0.11 |
| 16 | >10 | >10 | 2.3 | >10 |
| 17 | 2.1 | 2.2 | 1.7 | 0.68 |
| 18 | 4.4 | 2.7 | 1.4 | 2 |
| 19 | 3.1 | 1.1 | 0.66 | 0.97 |
| 21 | 2.2 | 3.6 | 0.55 | 1.7 |
| 22 | nd | 0.9 | 0.39 | 1.3 |
| 24 | >10 | 0.45 | 0.32 | 0.41 |

TABLE 5-continued

| Example | Ba/F3 EGFR wt. $IC_{50}$ (μM) | Ba/F3 EGFR del19 $IC_{50}$ (μM) | Ba/F3 EGFR del19/T790M $IC_{50}$ (μM) | Ba/F3 EGFR del19/T790M/C797S $IC_{50}$ (μM) |
|---|---|---|---|---|
| 25 | 0.34 | 0.21 | 0.78 | 0.027 |
| 27 | nd | 1.1 | 0.94 | >10 |
| 28 | 1.4 | 1.4 | 0.69 | 1.7 |
| 29 | 2.8 | 1.9 | 2.1 | 2.9 |
| 30 | 5.4 | 0.68 | 0.85 | 2.7 |
| 32 | 8 | 1.9 | 1.3 | 3.3 |
| 33 | nd | nd | nd | 0.12 |
| 34 | nd | nd | nd | 0.16 |
| 35 | nd | nd | nd | 0.084 |
| 36 | nd | nd | nd | 0.93 |
| 37 | nd | nd | nd | 0.099 |
| 38 | nd | nd | nd | 0.84 |
| 39 | nd | nd | nd | 0.68 |
| 40 | nd | nd | nd | 0.5 |

In Table 5 above, nd refers to no data.

As indicated in Table 5 above, it was confirmed that the example compounds according to the present invention showed a high inhibitory ability on EGFR mutation including EGFR del19/T790M/C797S, which is a triple mutation.

In addition, it can be seen that the example compounds according to the present invention show a relatively weak activity inhibitory ability on wild-type EGFR in Ba/F3 cell line and a selectively high inhibitory ability on EGFR mutation including EGFR del19/T790M/C797S, which is a triple mutation.

<Experimental Example 3> Measurement of an inhibitory ability on FLT kinase of the compound represented by Formula 1 according to the present invention (N2,N4-diphenylpyrimidin-2,4-diamine derivative)

In order to confirm an inhibitory ability on FLT kinase, which is also well known as a kinase associated with hematologic malignancy, of the compound represented by Formula 1 according to the present invention, the experiment was carried out as described below. The results are shown in Table 6 below.

The inhibitory activity on FLT kinase, such as wild-type FLT1, FLT3, FLT4, and FLT3 mutation forms, FLT3 (D835H), FLT3(D835V), FLT3(D835Y), FLT3(ITD), FLT3 (ITD,D835V), FLT3(ITD,F691L), FLT3(K663Q), FLT3 (N841I), FLT3(R834Q) was measured.

The specific experiment method is as described below.

FLT3 kinase inhibition was carried out by KINOMEscan method (DiscoverX Inc.). KINOMEscan method consists of the following processes. T7 bacteriophage labeled with FLT kinase was cultured by the infection to *E. coli* derived from BL21. After the infection of *E. coli* in the condition of 0.4 of MOI (multiplicity of infection), it was cultured for 90 to 150 minutes at 32° C. to lyse *E. coli*. The cell debris was removed by centrifugation and filtration, and the kinase protein present in the supernatant was secured. Additionally, the kinase protein was labeled with DNA for the qPCR measurement. The magnetic beads labeled with streptavidin were treated with the standard compound labeled with biotin and reacted for 30 minutes. The resulting beads were used as affinity beads for the measurement of a kinase activity. The binding reaction was initiated with mixing a kinase protein, the affinity beads bound with a ligand, and the compound. In this case, the used buffer solution was 20% SeaBlock, 0.17xPBS, 0.05% Tween 20, 6 mM DTT. All the reactions were carried out in volume of 20 ul at a 384 well plate. After the reaction for 1 hour at ambient temperature, the beads were washed with the solution consisting of 1×PBS, 0.05 Tween 20. Finally, the kinase bound with the beads was eluted by using 1×PBS, 0.05 Tween 20, 0.5 uM standard compound unlabeled with biotin. The affinity of the compound to be tested was indirectly measured by Quantifying the eluted kinase by OCR.

TABLE 6

| Example | Gene Symbol | Modifier | Kd (nM) |
|---|---|---|---|
| 10 | FLT1 | > | 10000 |
| 10 | FLT3 | = | 3.7 |
| 10 | FLT3(D835H) | = | 38 |
| 10 | FLT3(D835V) | = | 0.29 |
| 10 | FLT3(D835Y) | = | 4.2 |
| 10 | FLT3(ITD) | = | 18 |
| 10 | FLT3(ITD, D835V) | = | 0.32 |
| 10 | FLT3(ITD, F691L) | = | 1.1 |
| 10 | FLT3(K663Q) | = | 39 |
| 10 | FLT3(N841I) | = | 6.5 |
| 10 | FLT3(R834Q) | = | 33 |
| 10 | FLT4 | = | 200 |
| 11 | FLT1 | = | 910 |
| 11 | FLT3 | = | 1.2 |
| 11 | FLT3(D835H) | = | 1.8 |
| 11 | FLT3(D835V) | = | 0.082 |
| 11 | FLT3(D835Y) | = | 1.5 |
| 11 | FLT3(ITD) | = | 4.2 |
| 11 | FLT3(ITD, D835V) | = | 0.16 |
| 11 | FLT3(ITD, F691L) | = | 0.27 |
| 11 | FLT3(K663Q) | = | 20 |
| 11 | FLT3(N841I) | = | 3.8 |
| 11 | FLT3(R834Q) | = | 19 |
| 11 | FLT4 | = | 81 |

As indicated in Table 6 above,
it was confirmed that the compounds of Examples 10 and 11 of the present invention showed a selectively superior inhibitory ability on FLT 3 kinase in comparison with FLT 1 and FLT 4, and also showed a high inhibitory ability on wild-type FLT3, as well as, FLT3 mutation forms, such as FLT3(D835H), FLT3(D835V), FLT3(D835Y), FLT3(ITD), FLT3(ITD,D835V), FLT3(ITD,F691L), FLT3(K663Q), FLT3(N841I), FLT3(R834Q).

<Experimental Example 4> Evaluation of a Cell Activity on Ba/F3 Del19/T790M/C797S Cell Line According to the Combination Administration In order to confirm a cell activity on Ba/F3 Del19/T790M/C797S cell line when administering the compound according to the present invention in combination with a conventional drug, cetuximab to be used in single therapy or combination therapy with anticancer chemotherapy in metastatic colorectal cancer, metastatic squamous epithelium head and neck cancer and the like was used to evaluate the cell activity according to the combination administration.

Specifically, brigatinib was used as a control drug, and each of 30 nM of brigatinib, 30 nM of the compound of Example 10 according to the present invention, and 15 nM of the compound of Example 11 was administered to Ba/F3 Del19/T790M/C797S cell line in combination with 10 μg of cetuximab, which is a monoclonal antibody. The relative cell viability was measured and shown in FIGS. 1 to 4.

Figure 5:
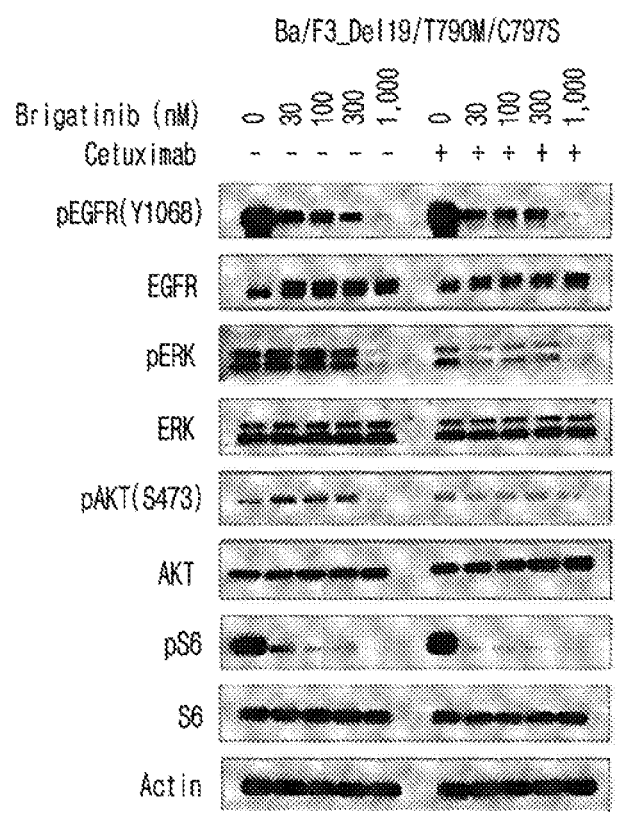
FIG. 5 shows a sub-signal activity at the time of the administration of brigatinib alone or in combination with cetuximab to Ba/F3 Del19/T790M/C797S cell line.
Figure 6:
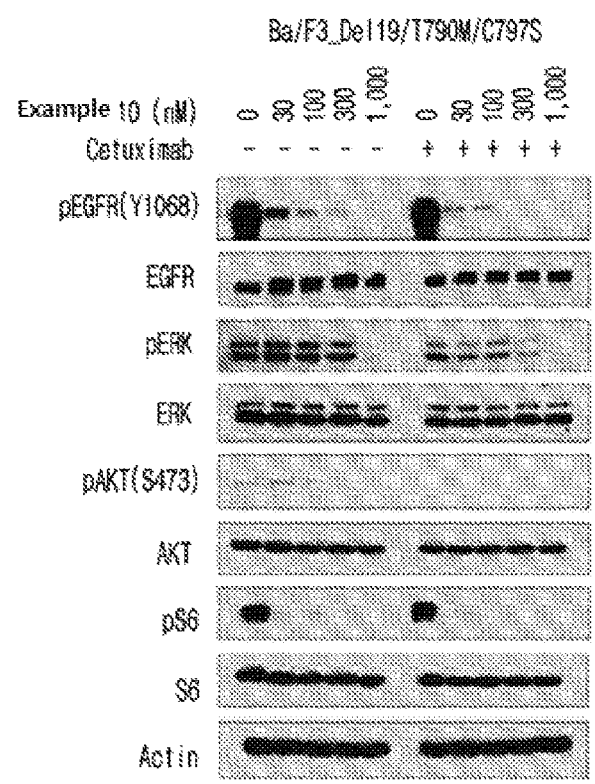
FIG. 6 shows a sub-signal activity at the time of the administration of the compound of Example 10 alone or in combination with cetuximab to Ba/F3 Del19/T790M/C797S cell line.
Figure 7:
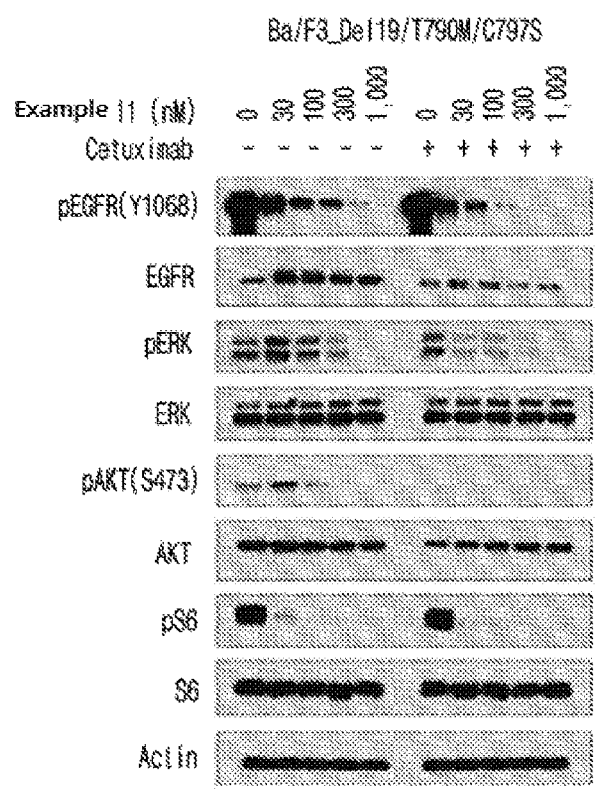
FIG. 7 shows a sub-signal activity at the time of the administration of the compound of Example 11 alone or in combination with cetuximab to Ba/F3 Del19/T790M/C797S cell line.

In addition, when administering each of brigatinib, the compounds of Examples 10 and 11 of the present invention in 30, 100, 300, 1000 nM alone or in combination with 10 μg of cetuximab, the sub-signal activity on a/F$_3$ Del19/T790M/C797S cell line was evaluated and the results are shown in FIGS. 5 to 7.

FIG. 1 is a graph showing a relative cell viability at the time of the administration of brigatinib in combination with cetuximab to Ba/F3 Del19/T790M/C797S cell line (calculated by sigmaplot's t-test (**$P<0.001$, *$P>0.01$)).

Figure 2:
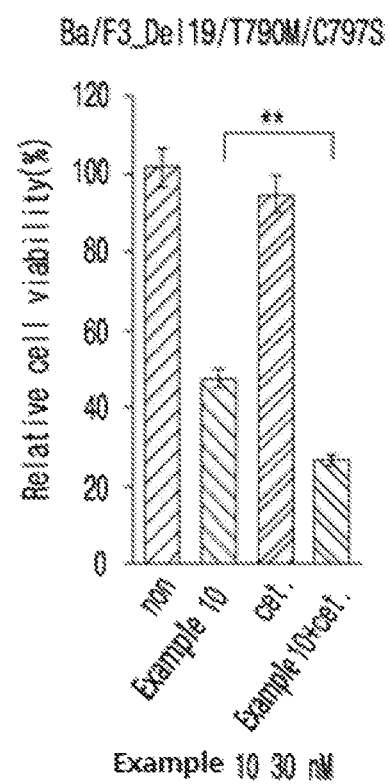
FIG. 2 is a graph showing a relative cell viability at the time of the administration of the compound of Example 10 in combination with cetuximab to Ba/F3 Del19/T790M/C797S cell line (calculated by sigmaplot's t-test (**P<0.001, *P>0.01)).

FIG. 2 is a graph showing a relative cell viability at the time of the administration of the compound of Example 10 in combination with cetuximab to Ba/F3 Del19/T790M/C797S cell line (calculated by sigmaplot's t-test (**$P<0.001$, *$P>0.01$)).

Figure 3:
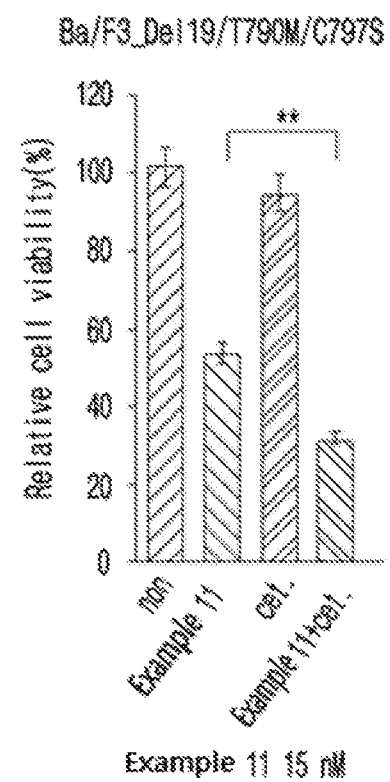
FIG. 3 is a graph showing a relative cell viability at the time of the administration of the compound of Example 11 in combination with cetuximab to Ba/F3 Del19/T790M/C797S cell line (calculated by sigmaplot's t-test (**P<0.001, *P>0.01)).

FIG. 3 is a graph showing a relative cell viability at the time of the administration of the compound of Example 11 in combination with cetuximab to Ba/F3 Del19/T790M/C797S cell line (calculated by sigmaplot's t-test (**$P<0.001$, *$P>0.01$)).

Figure 4:
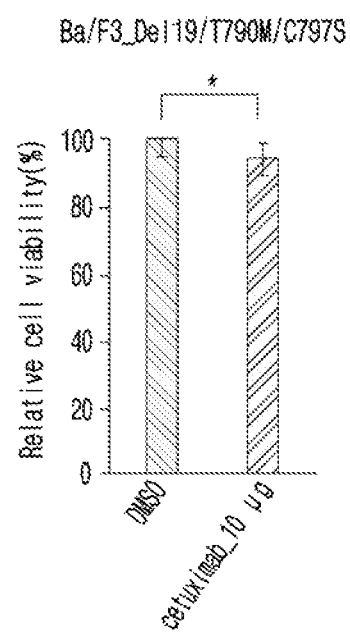
FIG. 4 is a graph showing a relative cell viability at the time of the administration of only cetuximab alone to Ba/F3 Del19/T790M/C797S cell line (calculated by sigmaplot's t-test (**P<0.001, *P>0.01)).

FIG. 4 is a graph showing a relative cell viability at the time of the administration of only cetuximab alone to Ba/F3 Del19/T790M/C797S cell line (calculated by sigmaplot's t-test (**$P<0.001$, *$P>0.01$)).

FIG. 5 shows a sub-signal activity at the time of the administration of brigatinib alone or in combination with cetuximab to Ba/F3 Del19/T790M/C797S cell line.

FIG. 6 shows a sub-signal activity at the time of the administration of the compound of Example 10 alone or in combination with cetuximab to Ba/F3 Del19/T790M/C797S cell line.

FIG. 7 shows a sub-signal activity at the time of the administration of the compound of Example 11 alone or in combination with cetuximab to Ba/F3 Del19/T790M/C797S cell line.

As shown in FIGS. 1 to 4,
it can be seen that the compounds of Examples 10 and 11 of the present invention show a lower cell viability by at least 30% on Ba/F3 Del19/T790M/C797S cell line when administered alone than cetuximab, and show a cell viability decreased by at least 50% when administered in combination with cetuximab than when administered alone, and thus, show a superior cancer cell apoptosis ability on a cell line with EGFR triple mutation even when administered alone, as well as, show a remarkably elevated anticancer effect when administered in combination with a conventional drug.

In particular, it can be seen that the compounds of Examples 10 and 11 of the present invention show a cell viability decreased by at least 20% than when administering brigatinib, which is a conventional drug in use, in combination with cetuximab, and thus, show a superior anticancer effect than brigatinib.

As shown in FIGS. 5 to 6,
it can be seen that the compounds of Examples 10 and 11 of the present invention show a concentration-dependent activity in pERK, pAKT, pS6, which is EGFR sub-signal, even when administered alone, as well as, show a superior activity when administered in combination with cetuximab.

In particular, it can be seen that the compounds of Examples 10 and 11 of the present invention show a superior activity than when administering brigatinib, which is a conventional drug in use, in combination with cetuximab, and thus, show a superior anticancer effect than brigatinib.

Therefore, the compound represented by Formula 1 according to the present invention shows a high inhibitory ability on EGFR mutation, and thus, can be effectively used for the treatment of cancer with EGFR mutation, such as EGFR del19, EGFR del19/T790M, EGFR del19/T790M/C797S, EGFR L858R, EGFR L858R/T790MS, EGFR L858R/T790M/C797S and the like. In particular, the compound represented by Formula 1 according to the present invention shows a remarkably superior inhibitory ability on EGFR del19/T790M/C797S or EGFR L858R/T790M/

C797S, which is a triple mutation, and thus, can be effectively used for the treatment of cancer with EGFR del19/T790M/C797S or EGFR L858R/T790M/C797S.

In addition, the compound represented by Formula 1 according to the present invention shows a high inhibitory ability on FLT 3 and mutation thereof, such as FLT3 (D 835H), FLT3(D835V), FLT3(D835Y), FLT3 (ITD), FLT3 (ITD,D835V), FLT3(ITD,F691L), FLT3(K663Q), FLT3 (N841I), or FLT3(R834Q), and thus, can be effectively used for the treatment of cancer associated with an activity of FLT 3 or a mutation form of FLT 3, particularly hematologic malignancy.

In addition, the compound represented by Formula 1 according to the present invention shows a synergy effect when administered in combination with a conventional drug, and thus, can be effectively used when administered in combination with a conventional drug.

<Formulation Example 1> Preparation of Powders

| | |
|---|---|
| Derivative represented by Formula 1 | 2 g |
| Lactose | 1 g |

The powders were prepared by mixing the above ingredients and filling into an airtight bag.

<Formulation Example 2> Preparation of Tablets

| | |
|---|---|
| Derivative represented by Formula 1 | 100 mg |
| Corn starch | 100 mg |
| Lactose | 100 mg |
| Magnesium stearate | 2 mg |

The tablets were prepared by mixing the above ingredients and then tableting according to conventional methods for manufacturing tablets.

<Formulation Example 3> Preparation of Capsules

| | |
|---|---|
| Derivative represented by Formula 1 | 100 mg |
| Corn starch | 100 mg |
| Lactose | 100 mg |
| Magnesium stearate | 2 mg |

The capsules were prepared by mixing the above ingredients and then filling into gelatin capsules according to conventional methods for manufacturing capsules.

<Formulation Example 4> Preparation of Injections

| | |
|---|---|
| Derivative represented by Formula 1 | 100 mg |
| Mannitol | 180 mg |
| $Na_2HPO_4 \cdot 2H_2O$ | 26 mg |
| Distilled water | 2974 mg |

The injections were prepared by containing the above ingredients in contents set forth above according to conventional methods for manufacturing injections.

<Formulation Example 5> Preparation of Health Foods

| | |
|---|---|
| Derivative represented by Formula 1 | 500 ng |
| Vitamin mixture | q.s. |
| Vitamin A acetate | 70 mg |
| Vitamin E | 1.0 mg |
| Vitamin | 0.13 mg |
| Vitamin B2 | 0.15 mg |
| Vitamin B6 | 0.5 mg |
| Vitamin B12 | 0.2 mg |
| Vitamin C | 10 mg |
| Biotin | 10 mg |
| Nicotinamide | 1.7 mg |
| Folic acid | 50 mg |
| Calcium pantothenate | 0.5 mg |
| Mineral mixture | q.s. |
| Ferrous sulfate | 1.75 mg |
| Zinc oxide | 0.82 mg |
| Magnesium carbonate | 25.3 mg |
| Potassium dihydrogen phosphate | 15 mg |
| Calcium hydrogen phosphate | 55 mg |
| Potassium citrate | 90 mg |
| Calcium carbonate | 100 mg |
| Magnesium chloride | 24.8 mg |

In regard to the composition ratio of the vitamin and mineral mixture, the ingredients relatively suitable for health foods were mixed according to the preferred examples, but the mixing ratio can be optionally modified in practice. According to conventional methods for manufacturing health foods, the above ingredients were mixed and then prepared into granules, and may be used in the preparation of health food compositions according to conventional methods.

<Formulation Example 6> Preparation of Health Beverages

| | |
|---|---|
| Derivative represented by Formula 1 | 500 ng |
| Citric acid | 1000 mg |
| Oligosaccharide | 100 g |
| Japanese apricot concentrate | 2 g |
| Taurine | 1 g |
| Purified water added to a total of | 900 ml |

According to conventional methods for manufacturing health beverages, the above ingredients were mixed, then stirred and heated at 85° C. for about 1 hour, and then the resulting solution was filtered, obtained in a sterilized container, sealed, sterilized, then stored in a refrigerator, and used in the preparation of health beverage compositions.

In regard to the composition ratio, the ingredients relatively suitable for favorite beverages were mixed according to the preferred examples, but the mixing ratio can be optionally modified in practice according to regional and ethnic preference, such as a demand class, demand country, purpose of use and the like.

INDUSTRIAL APPLICABILITY

The N2,N4-diphenylpyrimidin-2,4-diamine derivative according to the present invention can be effectively used for the treatment of cancer, particularly cancer with EGFR mutation or cancer with FLT3 or a mutation thereof.

The invention claimed is:
1. A compound represented by Formula 1:

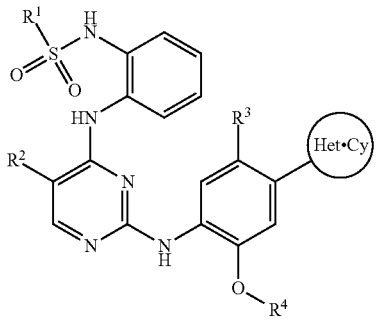
(1)

in which,
R¹ is CH₃ or NH₂,
R² is hydrogen, halogen, methoxy, or methyl unsubstituted or substituted with one or more halogens;
R³ is hydrogen, halogen, or straight or branched $C_{1-6}$alkyl;
R⁴ is straight or branched $C_{1-6}$alkyl; and

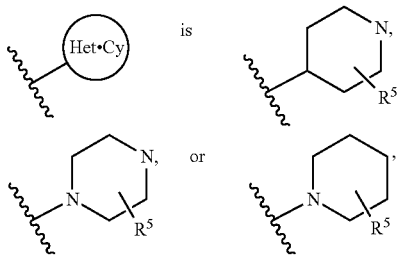

wherein the R⁵ is independently selected from hydrogen, straight or branched $C_{1-3}$alkyl, straight or branched hydroxy$C_{1-3}$alkyl, acetyl, —NR$^a$R$^b$, morpholinyl, pyrrolidinyl, and unsubstituted or substituted piperidinyl or piperazinyl, wherein R$^a$ and R$^b$ are independently hydrogen, straight or branched $C_{1-3}$alkyl, acetyl, straight or branched hydroxy$C_{1-3}$alkyl, straight or branched $C_{1-3}$alkoxy$C_{1-2}$alkyl, or straight or branched di$C_{1-3}$alkylamino$C_{1-2}$alkyl, and the substituted piperidinyl or piperazinyl may be substituted with one or more substituents selected from the group consisting of straight or branched $C_{1-3}$alkyl, straight or branched hydroxy$C_{1-3}$alkyl, acetyl, and straight or branched $C_{1-5}$alkoxycarbonyl, an optical isomer thereof or a pharmaceutically acceptable salt thereof.

2. The compound, optical isomer thereof, or pharmaceutically acceptable salt thereof according to claim 1, characterized in that R¹ is CH₃.

3. The compound, optical isomer thereof, or pharmaceutically acceptable salt thereof according to claim 1, characterized in that R¹ is NH₂.

4. The compound, optical isomer thereof, or pharmaceutically acceptable salt thereof according to claim 1, characterized in that
R² is hydrogen, F, Cl, Br, methoxy, or methyl unsubstituted or substituted with one or more fluoro;
R³ is hydrogen, F, Cl, or straight or branched $C_{1-3}$alkyl; and
R⁴ is straight or branched $C_{1-3}$alkyl.

5. The compound, optical isomer thereof, or pharmaceutically acceptable salt thereof according to claim 1, characterized in that
R² is hydrogen, Cl, Br, methyl, CF₃, or methoxy;
R³ is hydrogen or methyl; and
R⁴ is methyl.

6. The compound, optical isomer thereof, or pharmaceutically acceptable salt thereof according to claim 1, characterized in that
R⁵ is independently selected from the group consisting of hydrogen, methyl, hydroxyethyl, acetyl, —NR$^a$R$^b$, morpholinyl, pyrrolidinyl, and unsubstituted or substituted piperidinyl or piperazinyl, wherein R$^a$ and R$^b$ are independently hydrogen, straight or branched $C_{1-3}$alkyl, acetyl, straight or branched hydroxy$C_{1-3}$alkyl, straight or branched $C_{1-3}$alkoxy$C_{1-2}$alkyl, or straight or branched di$C_{1-3}$alkylamino$C_{1-2}$alkyl, and the substituted piperidinyl or piperazinyl may be substituted with one or more substituents selected from the group consisting of methyl, ethyl, hydroxymethyl, hydroxyethyl, acetyl, and tert-butoxycarbonyl.

7. The compound, optical isomer thereof, or pharmaceutically acceptable salt thereof according to claim 1, characterized in that
R⁵ is independently selected from the group consisting of hydrogen, methyl, hydroxyethyl, acetyl, —NR$^a$R$^b$, morpholinyl, pyrrolidinyl, and unsubstituted or substituted piperidinyl or piperazinyl, wherein R$^a$ and R$^b$ are independently hydrogen, methyl, acetyl, hydroxyethyl, —(CH₂)₂OCH₃, or —(CH₂)₂N(CH₃)₂, and the substituted piperidinyl or piperazinyl may be substituted with one or more substituents selected from the group consisting of methyl, hydroxyethyl, acetyl, and tert-butoxycarbonyl.

8. The compound, optical isomer thereof, or pharmaceutically acceptable salt thereof according to claim 1, characterized in that
R⁵ is independently hydrogen, methyl, hydroxyethyl, acetyl, —NR$^a$R$^b$, morpholinyl, pyrrolidinyl,

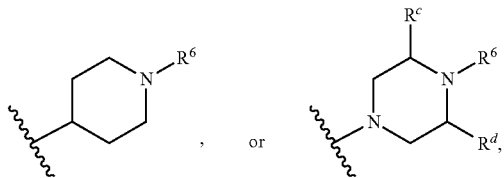

wherein R$^a$ and R$^b$ are independently hydrogen, methyl, acetyl, hydroxyethyl, —(CH₂)₂OCH₃, or —(CH₂)₂N(CH₃)₂, and R$^c$ and R$^d$ are independently hydrogen, methyl, or ethyl, and R⁶ is independently hydrogen, methyl, hydroxyethyl, acetyl, or tert-butoxycarbonyl.

9. The compound, optical isomer thereof, or pharmaceutically acceptable salt thereof according to claim 1, characterized in that
R⁵ is independently hydrogen, methyl, hydroxyethyl, acetyl, —NH₂, —NH(CH₃), —NH(C=O)CH₃, —NH(CH₂)₂OH, —NH(CH₂)₂OCH₃, —NH(CH₂)₂N(CH₃)₂, —N(CH₃)₂, morpholinyl, pyrrolidinyl,

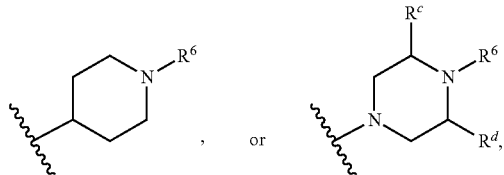

wherein $R^c$ and $R^d$ are independently hydrogen or methyl, and $R^6$ is independently hydrogen, methyl, hydroxyethyl, acetyl, or tert-butoxycarbonyl.

10. The compound, optical isomer thereof, or pharmaceutically acceptable salt thereof according to claim 1, characterized in that

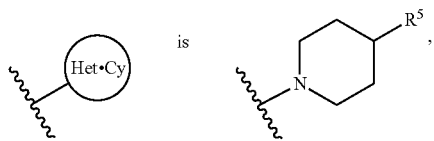

wherein $R^5$ is independently —NH(CH$_3$) or

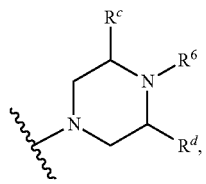

wherein $R^c$ and $R^d$ are independently hydrogen, and $R^6$ is methyl.

11. The compound, optical isomer thereof, or pharmaceutically acceptable salt thereof according to claim 1, characterized in that the compound represented by Formula 1 is any one selected from the group consisting of the following compounds:

<1> N-(2-((5-chloro-2-((2-methoxy-4-(piperidin-4-yl)phenyl)amino)pyrimidin-4-yl)amino)phenyl)methanesulfonamide;
<2> N-(2-((5-chloro-2-((2-methoxy-5-methyl-4-(piperidin-4-yl)phenyl)amino)pyrimidin-4-yl)amino)phenyl)methanesulfonamide;
<3> N-(2-((5-bromo-2-((2-methoxy-4-(piperidin-4-yl)phenyl)amino)pyrimidin-4-yl)amino)phenyl)methanesulfonamide;
<4> N-(2-((5-methoxy-2-((2-methoxy-4-(piperidin-4-yl)phenyl)amino)pyrimidin-4-yl)amino)phenyl)methanesulfonamide;
<5> N-(2-((2-((2-methoxy-4-(piperazin-1-yl)phenyl)amino)-5-(trifluoromethyl)pyrimidin-4-yl)amino)phenyl)methanesulfonamide;
<6> 4-(4-((5-chloro-4-((2-(sulfamoylamino)phenyl)amino)pyrimidin-2-yl)amino)-3-methoxyphenyl)piperidine;
<7> 4-(4-((5-bromo-4-((2-(sulfamoylamino)phenyl)amino)pyrimidin-2-yl)amino)-3-methoxyphenyl)piperidine;
<8> N-(2-((2-((2-methoxy-4-(piperidin-4-yl)phenyl)amino))-5-methylpyrimidin-4-ylamino)phenyl)methanesulfonamide;
<9> N-(2-((2-((2-methoxy-4-(piperidin-4-yl)phenyl)amino)pyrimidin-4-yl)amino)phenyl)methanesulfonamide;
<10> N-(2-((5-chloro-2-((2-methoxy-4-(4-(4-methylpiperazin-1-yl)piperidin-1-yl)phenyl)amino)pyrimidin-4-yl)amino)phenyl)methanesulfonamide;
<11> N-(2-((5-chloro-2-((4-(4-(dimethylamino)piperidin-1-yl)-2-methoxyphenyl)amino)pyrimidin-4-yl)amino)phenyl)methanesulfonamide;
<12> N-(2-((5-chloro-2-((2-methoxy-4-(1-methylpiperidin-4-yl)phenyl)amino)pyrimidin-4-yl)amino)phenyl)methanesulfonamide;
<13> N-(2-((5-chloro-2-((4-(1-(2-hydroxyethyl)piperidin-4-yl)-2-methoxyphenyl)amino)pyrimidin-4-yl)amino)phenyl)methanesulfonamide;
<14> N-(2-((5-chloro-2-((4-(1'-(2-hydroxyethyl)-[1,4'-bipiperidin]-4-yl)-2-methoxyphenyl)amino)pyrimidin-4-yl)amino)phenyl)methanesulfonamide;
<15> N-(2-((2-((4-(1-acetylpiperidin-4-yl)-2-methoxyphenyl)amino)-5-chloropyrimidin-4-yl)amino)phenyl)methanesulfonamide;
<16> N-(2-((2-((4-([1,4'-bipiperidin]-4-yl)-2-methoxyphenyl)amino)-5-chloropyrimidin-4-yl)amino)phenyl)methanesulfonamide;
<17> N-(2-((5-chloro-2-((2-methoxy-4-(1'-methyl-[1,4'-bipiperidin]-4-yl)phenyl)amino)pyrimidin-4-yl)amino)phenyl)methanesulfonamide;
<18> N-(2-((2-((4-(1'-acetyl-[1,4'-bipiperidin]-4-yl)-2-methoxyphenyl)amino)-5-chloropyrimidin-4-yl)amino)phenyl)methanesulfonamide;
<19> N-(2-((2-((4-(4-(4-acetylpiperazin-1-yl)piperidin-1-yl)-2-methoxyphenyl)amino)-5-chloropyrimidin-4-yl)amino)phenyl)methanesulfonamide;
<20> tert-butyl 4-(1-(4-((5-chloro-4-((2-(methylsulfonamido)phenyl)amino)pyrimidin-2-yl)amino)-3-methoxyphenyl)piperidin-4-yl)piperazine-1-carboxylate;
<21> N-(2-((5-chloro-2-((2-methoxy-4-(4-(piperazin-1-yl)piperidin-1-yl)phenyl)amino)pyrimidin-4-yl)amino)phenyl)methanesulfonamide;
<22> N-(2-((5-chloro-2-((4-(4-(4-(2-hydroxyethyl)piperazin-1-yl)piperidin-1-yl)-2-methoxyphenyl)amino)pyrimidin-4-yl)amino)phenyl)methanesulfonamide;
<23> N-(2-((5-chloro-2-((2-methoxy-4-(piperazin-1-yl)phenyl)amino)pyrimidin-4-yl)amino)phenyl)methanesulfonamide;
<24> N-(2-((2-((4-(4-(1-acetylpiperidin-4-yl)piperazin-1-yl)-2-methoxyphenyl)amino)-5-chloropyrimidin-4-yl)amino)phenyl)methanesulfonamide;
<25> N-(2-((5-chloro-2-((2-methoxy-4-(4-(1-methylpiperidin-4-yl)piperazin-1-yl)phenyl)amino)pyrimidin-4-yl)amino)phenyl)methanesulfonamide;
<26> tert-butyl 4-(4-(4-((5-chloro-4-((2-(methylsulfonamido)phenyl)amino)pyrimidin-2-yl)amino)-3-methoxyphenyl)piperazin-1-yl)piperidine-1-carboxylate;
<27> N-(2-((5-chloro-2-((2-methoxy-4-(piperidin-4-ylpiperazin-1-yl)phenyl)amino)pyrimidin-4-yl)amino)phenyl)methanesulfonamide;
<28> N-(2-((5-chloro-2-((2-methoxy-4-(4-methylpiperazin-1-yl)phenyl)amino)pyrimidin-4-yl)amino)phenyl)methanesulfonamide;
<29> 4-(4-((5-chloro-4-((2-(sulfamoylamino)phenyl)amino)pyrimidin-2-yl)amino)-3-methoxyphenyl)piperazine;

<30> 4-(4-((5-bromo-4-((2-(sulfamoylamino)phenyl)amino)pyrimidin-2-yl)amino)-3-methoxyphenyl)piperazine;

<31> N-(2-((2-((2-methoxy-4-(piperazin-4-yl)phenyl)amino)-5-(trifluoromethyl)pyrimidin-4-yl)amino)phenyl)methanesulfonamide;

<33> N-(2-((5-chloro-2-((4-(4-((3R,5S)-3,5-dimethylpiperazin-1-yl)piperidin-1-yl)-2-methoxyphenyl)amino)pyrimidin-4-yl)amino)phenyl)methanesulfonamide;

<34> N-(2-((5-chloro-2-((2-methoxy-4-(4-morpholinopiperidin-1-yl)phenyl)amino)pyrimidin-4-yl)amino)phenyl)methanesulfonamide;

<35> N-(2-((5-chloro-2-((2-methoxy-4-(4-(pyrrolidin-1-yl)piperidin-1-yl)phenyl)amino)pyrimidin-4-yl)amino)phenyl)methanesulfonamide;

<36> (N-(2-((5-chloro-2-((4-(4-(dimethylamino)piperidin-1-yl)-2-methoxyphenyl)amino)pyrimidin-4-yl)amino)phenyl)sulfamoyl)carbamate;

<37> (N-(2-((5-chloro-2-((2-methoxy-4-(4-(4-methylpiperazin-1-yl)piperidin-1-yl)phenyl)amino)pyrimidin-4-yl)amino)phenyl)sulfamoyl)carbamate;

<38> N-(2-((2-((4-(4-aminopiperidin-1-yl)-2-methoxyphenyl)amino)-5-chloropyrimidin-4-yl)amino)phenyl)methanesulfonamide;

<39> N-(1-(4-((5-chloro-4-((2-(methylsulfonamido)phenyl)amino)pyrimidin-2-yl)amino)-3-methoxyphenyl)piperidin-4-yl)acetamide;

<40> N-(2-((5-chloro-2-((2-methoxy-4-(4-(methylamino)piperidin-1-yl)phenyl)amino)pyrimidin-4-yl)amino)phenyl)methanesulfonamide;

<41> N-(2-((5-chloro-2-((4-(4-((2-hydroxyethyl)amino)piperidin-1-yl)-2-methoxyphenyl)amino)pyrimidin-4-yl)amino)phenyl)methanesulfonamide;

<42> N-(2-((5-chloro-2-((2-methoxy-4-(4-((2-methoxyethyl)amino)piperidin-1-yl)phenyl)amino)pyrimidin-4-yl)amino)phenyl)methanesulfonamide; and <43> N-(2-((5-chloro-2-((4-(4-((2-(dimethylamino)ethyl)amino)piperidin-1-yl)-2-methoxyphenyl)amino)pyrimidin-4-yl)amino)phenyl)methanesulfonamide.

12. A method for preparing the compound represented by Formula 1 of claim 1, comprising a step of reacting a compound represented by Formula 2 and a compound represented by Formula 3 to prepare the compound represented by Formula 1, as indicated in Reaction Scheme 1:

[Reaction Scheme 1]

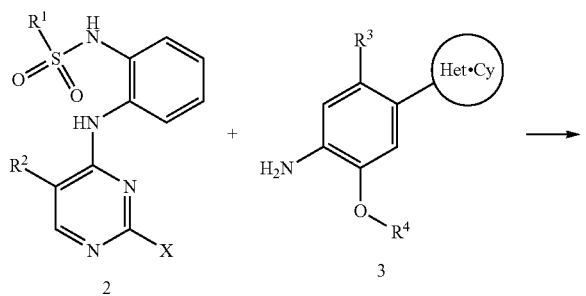

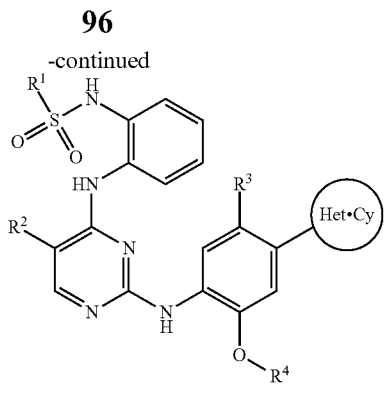

in which, $R^1$, $R^2$, $R^3$, $R^4$, and

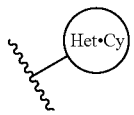

are as defined in Formula 1 of claim 1; and
X is halogen.

13. A pharmaceutical composition for the prevention or treatment of cancer, comprising the compound represented by Formula 1, optical isomer thereof, or pharmaceutically acceptable salt thereof according to claim 1 as an active ingredient.

14. The pharmaceutical composition according to claim 13, characterized in that the compound inhibits one or more selected from the group consisting of an EGFR (epidermal growth factor receptor) mutation, FLT3 (fms-like tyrosine kinase 3), and FLT3 mutation.

15. The pharmaceutical composition according to claim 14, characterized in that the EGFR mutation is one or more selected from the group consisting of EGFR del19, EGFR del19/T790M, EGFR del19/T790M/C797S, EGFR L858R, EGFR L858R/T790MS, and EGFR L858R/T790M/C797S.

16. The pharmaceutical composition according to claim 14, characterized in that the FLT3 mutation is one or more selected from the group consisting of FLT3(D835H), FLT3(D835V), FLT3(D835Y), FLT3(ITD), FLT3(ITD,D835V), FLT3(ITD,F691L), FLT3(K663Q), FLT3(N841I), and FLT3(R834Q).

17. The pharmaceutical composition according to claim 13, characterized in that the cancer has a mutation expressed on one or more selected from the group consisting of epidermal growth factor receptor (EGFR), anaplastic lymphoma kinase (ALK), focal adhesion kinase (FAK), fms-like tyrosine kinase 3 (FLT3), Janus kinase 3 (JAK3), tyrosine-protein kinase KIT (KIT), and polo-like kinase 4 (PLK4).

18. The pharmaceutical composition according to claim 13, characterized in that the cancer is one or more selected from the group consisting of pseudomyxoma, intrahepatic cholangiocarcinoma, hepatoblastoma, liver cancer, thyroid cancer, colon cancer, testis cancer, myelodysplastic syndrome, glioblastoma, oral cancer, lip cancer, mycosis fungoides, acute myeloid leukemia, acute lymphocytic leukemia, basal cell carcinoma, epithelial ovarian cancer, ovarian seminoma, male breast cancer, brain cancer, pituitary adenoma, multiple myeloma, gallbladder cancer, cholangiocarcinoma, colorectal cancer, chronic myeloid leukemia, chronic lymphocytic leukemia, retinoblastoma, choroidal melanoma, ampullar of vater cancer, bladder cancer, peritoneal cancer, parathyroid cancer, adrenal cancer, nasal and paranasal cavity cancer, non-small cell lung cancer, tongue cancer, astrocytoma, small cell lung cancer, pediatric brain cancer, pediatric lymphoma, pediatric leukemia, small intestine cancer, meningioma, esophageal cancer, glioma, renal pelvis cancer, renal cancer, heart cancer, duodenal cancer, malignant soft tissue cancer, malignant bone cancer, malignant lymphoma, malignant mesothelioma, malignant melanoma, eye cancer, vulvar cancer, ureteral cancer, urethral cancer, cancer of unknown primary site, gastric lymphoma, gastric cancer, gastric carcinoid, gastrointestinal stromal tumor, Wilms' tumor, breast cancer, sarcoma, penile cancer, pharyngeal cancer, gestational choriocarcinoma, cervical cancer, endometrial cancer, uterine sarcoma, prostate cancer, metastatic bone cancer, metastatic brain cancer, mediastinal cancer, rectal cancer, rectal carcinoid, vaginal cancer, spinal cancer, vestibular schwannoma, pancreatic cancer, salivary gland cancer, Kaposi's sarcoma, Paget's disease, tonsillar cancer, squamous cell cancer, adenocarcinoma of lung, lung cancer, squamous cell lung cancer, skin cancer, anal cancer, rhabdomyosarcoma, laryngeal cancer, pleura cancer, hematologic malignancy, and thymic cancer.

19. The pharmaceutical composition according to claim 13, characterized in that the pharmaceutical composition enhances an anticancer effect by the combination administration with an anticancer agent.

20. A health functional food for the prevention or amelioration of cancer, containing the compound represented by Formula 1, optical isomer thereof, or pharmaceutically acceptable salt thereof according to claim 1 as an active ingredient.

\* \* \* \* \*

UNITED STATES PATENT AND TRADEMARK OFFICE
CERTIFICATE OF CORRECTION

PATENT NO. : 11,253,516 B2
APPLICATION NO. : 16/622057
DATED : February 22, 2022
INVENTOR(S) : Kwangho Lee et al.

It is certified that error appears in the above-identified patent and that said Letters Patent is hereby corrected as shown below:

In the Specification

At Column 9, Line number 65-67, please replace:
"<5> N-(2-((2-((2-methoxy-4-(piperazin-1 -yl)phenyl)amino)-5-(trifluoromethyl)pyrimidin-4-yl)amino)phenyl) methanesulfonamide;"
With:
--<5> N-(2-((2-((2-methoxy-4-(piperidin-4-yl)phenyl)amino)-5-(trifluoromethyl)pyrimidin-4-yl)amino)phenyl)methanesulfonamide;--.

At Column 11, Line numbers 22-24, please replace:
"<36> (N-(2-((5-chloro-2-((4-(4-(dimethylamino)piperidin-1-yl)-2-methoxy phenyl)amino)pyrimidin-4-yl)amino) phenyl)sulfamoyl)carbamate;"
With:
--<36> N-(2-((5-chloro-2-((4-(4-(dimethylamino)piperidin-1-yl)-2 methoxyphenyl)amino)pyrimidin-4-yl)amino)phenyl)sulfamide;--.

At Column 11, Line numbers 25-27, please replace:
"<37> (N-(2-((5-chloro-2-((2-methoxy-4-(4-(4-methylpiper-azin-1 -yl)piperidin- 1-yl)phenyl)amino)pyrimidin-4 yl)amino)phenyl)sulfamoyl)carbamate;"
With:
--<37> N-(2-((5-chloro-2-((2-methoxy-4-(4-(4-methylpiperazin-1-yl)piperidin-1-yl)phenyl)amino)pyrimidin-4-yl)amino)phenyl)sulfamide;--.

At Column 26, Line numbers 1-3, please replace:
"<Example 5> Preparation of N-(2-((2-((2-methoxy-4-(piperazin-1 -yl)phenyl)amino)-5-(trifluoromethyl)pyrimidin-4-yl)amino)phenyl) methanesulfonamide"
With:
--<Example 5> Preparation of N-(2-((2-((2-methoxy-4-(piperidin-4-yl)phenyl)amino)-5-(trifluoromethyl)pyrimidin-4-yl)amino)phenyl)methanesulfonamide--.

Signed and Sealed this
Fourteenth Day of February, 2023

Katherine Kelly Vidal
*Director of the United States Patent and Trademark Office*

CERTIFICATE OF CORRECTION (continued)
U.S. Pat. No. 11,253,516 B2

At Column 57, Line numbers 37-40, please replace:
"<Example 36> Preparation of (N-(2-((5-chloro-2-((4-(4-(dimethylamino)piperidin-1-yl)-2-methoxy phenyl)amino)pyrimidin-4-yl)amino) phenyl)sulfamoyl)carbamate"
With:
--<Example 36> N-(2-((5-chloro-2-((4-(4-(dimethylamino)piperidin-1-yl)-2 methoxyphenyl)amino)pyrimidin-4-yl)amino)phenyl)sulfamide--.

At Column 58, Line numbers 26-29, please replace:
"Step 4: Preparation of (N-(2-((5-chloro-2-((4-(4-(dimethylamino)piperidin-1-yl)-2-methoxy phenyl)amino)pyrimidin-4-yl)amino) phenyl)sulfamoyl)carbamate"
With:
--Step 4: Preparation of N-(2-((5-chloro-2-((4-(4-(dimethylamino)piperidin-1-yl)-2 methoxyphenyl)amino)pyrimidin-4-yl)amino)phenyl)sulfamide--.

At Column 58, Line numbers 31-34, please replace:
"The same manner as in Step 4 of Example 6 above was performed to obtain (N-(2-((5-chloro-2-((4-(4-(dimethylamino)piperidin-1-yl)-2-methoxy phenyl)amino)pyrimidin-4-yl)amino) phenyl)sulfamoyl)carbamate"
With:
--The same manner as in Step 4 of Example 6 above was performed to obtain N-(2-((5-chloro-2-((4-(4-(dimethylamino)piperidin-1-yl)-2 methoxyphenyl)amino)pyrimidin-4-yl)amino)phenyl)sulfamide--.

At Column 59, Line numbers 35-38, please replace:
"<Example 37> Preparation of (N-(2-((5-chloro-2-((2-methoxy-4-(4-(4-methylpiper-azin-1 -yl)piperidin- 1-yl)phenyl)amino)pyrimidin-4 yl)amino)phenyl)sulfamoyl)carbamate"
With:
--<Example 37> Preparation of N-(2-((5-chloro-2-((2-methoxy-4-(4-(4-methylpiperazin-1-yl)piperidin-1-yl)phenyl)amino)pyrimidin-4-yl)amino)phenyl)sulfamide--.

At Column 60, Line numbers 21-24, please replace:
"Step 4: Preparation of (N-(2-((5-chloro-2-((2-methoxy-4-(4-(4-methylpiper-azin-1 -yl)piperidin- 1-yl)phenyl)amino)pyrimidin-4 yl)amino)phenyl)sulfamoyl)carbamate"
With:
--Step 4: Preparation of N-(2-((5-chloro-2-((2-methoxy-4-(4-(4-methylpiperazin-1-yl)piperidin-1-yl)phenyl)amino)pyrimidin-4-yl)amino)phenyl)sulfamide--.

At Column 60, Line numbers 26-29, please replace:
"The same manner as Step 4 of Example 6 above was performed to obtain (N-(2-((5-chloro-2-((2-methoxy-4-(4-(4-methylpiper-azin-1 -yl)piperidin- 1-yl)phenyl)amino)pyrimidin-4 yl)amino)phenyl)sulfamoyl)carbamate"
With:
--The same manner as Step 4 of Example 6 above was performed to obtain N-(2-((5-chloro-2-((2-methoxy-4-(4-(4-methylpiperazin-1-yl)piperidin-1-yl)phenyl)amino)pyrimidin-4-yl)amino)phenyl)sulfamide--.

CERTIFICATE OF CORRECTION (continued)
U.S. Pat. No. 11,253,516 B2

In the Claims

At Column 93, Claim 11, Line number 56-58, please replace:
"<5> N-(2-((2-((2-methoxy-4-(piperazin-1 -yl)phenyl)amino)-5-(trifluoromethyl)pyrimidin-4-yl)amino)phenyl) methanesulfonamide;"
With:
--<5> N-(2-((2-((2-methoxy-4-(piperidin-4-yl)phenyl)amino)-5-(trifluoromethyl)pyrimidin-4-yl)amino)phenyl)methanesulfonamide;--.

At Column 95, Claim 11, Line number 19-21, please replace:
"<36> (N-(2-((5-chloro-2-((4-(4-(dimethylamino)piperidin-1-yl)-2-methoxy phenyl)amino)pyrimidin-4-yl)amino) phenyl)sulfamoyl)carbamate;"
With:
--<36> N-(2-((5-chloro-2-((4-(4-(dimethylamino)piperidin-1-yl)-2 methoxyphenyl)amino)pyrimidin-4-yl)amino)phenyl)sulfamide;--.

At Column 95, Claim 11, Line number 22-24, please replace:
"<37> (N-(2-((5-chloro-2-((2-methoxy-4-(4-methylpiper-azin-1 -yl)piperidin- 1-yl)phenyl)amino)pyrimidin-4 yl)amino)phenyl)sulfamoyl)carbamate;"
With:
--<37> N-(2-((5-chloro-2-((2-methoxy-4-(4-methylpiperazin-1-yl)piperidin-1-yl)phenyl)amino)pyrimidin-4-yl)amino)phenyl)sulfamide;--.